US011911441B2

(12) United States Patent
Liu et al.

(10) Patent No.: US 11,911,441 B2
(45) Date of Patent: Feb. 27, 2024

(54) METHODS OF USE OF CD24 FOR THE PREVENTION AND TREATMENT OF LEUKEMIA RELAPSE

(71) Applicants: ONCOIMMUNE, INC., Rockville, MD (US); UNIVERSITY OF MARYLAND, BALTIMORE, Baltimore, MD (US)

(72) Inventors: Yang Liu, Baltimore, MD (US); Pan Zheng, Baltimore, MD (US); Martin Devenport, Gaithersburg, MD (US)

(73) Assignees: ONCOIMMUNE, INC., Rockville, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/734,957

(22) PCT Filed: Jun. 3, 2019

(86) PCT No.: PCT/US2019/035205
§ 371 (c)(1),
(2) Date: Dec. 3, 2020

(87) PCT Pub. No.: WO2019/236474
PCT Pub. Date: Dec. 12, 2019

(65) Prior Publication Data
US 2021/0268061 A1 Sep. 2, 2021

Related U.S. Application Data

(60) Provisional application No. 62/739,742, filed on Oct. 1, 2018, provisional application No. 62/739,719, filed on Oct. 1, 2018, provisional application No. 62/680,218, filed on Jun. 4, 2018.

(51) Int. Cl.
A61K 39/00 (2006.01)
A61K 38/00 (2006.01)
A61P 35/02 (2006.01)
A61K 38/16 (2006.01)
A61K 38/17 (2006.01)
A61P 37/06 (2006.01)
A61P 1/04 (2006.01)
C07K 14/705 (2006.01)
C07K 16/42 (2006.01)
A61K 35/02 (2015.01)

(52) U.S. Cl.
CPC .......... A61K 38/177 (2013.01); A61K 35/02 (2013.01); A61K 39/001129 (2018.08); A61P 1/04 (2018.01); A61P 37/06 (2018.01); C07K 14/70596 (2013.01); C07K 16/4241 (2013.01); A61K 2039/545 (2013.01); C07K 2317/41 (2013.01); C07K 2317/524 (2013.01); C07K 2317/526 (2013.01); C07K 2317/528 (2013.01); C07K 2317/53 (2013.01); C07K 2319/30 (2013.01)

(58) Field of Classification Search
None
See application file for complete search history.

(56) References Cited

U.S. PATENT DOCUMENTS

2011/0123522 A1   5/2011   Arber

FOREIGN PATENT DOCUMENTS

WO   2016073704 A1   5/2016
WO   2017136492 A1   8/2017

OTHER PUBLICATIONS

Cambridge English Dictionary, available online at https://dictionary.cambridge.org/us/dictionary/english/prevention, 9 page (accessed on Dec. 23, 2022) (Year: 2022).*
Magenau et al., Abstracts/Biol. Blood Marrow Transplant 26:S52-S53, Abstract No. 70 (2020) (Year: 2020).*
Fayed, "Can You Prevent Leukemia?", verywell health, available online at https://www.verywellhealth.com/leukemia-prevention-514159, 14 pages (2022) (Year: 2022).*
Antar et al., Frontiers Oncol. 10:12 pages (2020) (Year: 2020).*
UniProt Accession No. P25063, 9 pages (2018) (Year: 2018).*
Clinical Trial No. NCT02663622, 5 pages (Sep. 6, 2016) (Year: 2016).*
Kim et al., Appl. Microbiol. Biotechnol. 93:917-930 (2012) (Year: 2012).*
Zheng et al., "CD24 as a Potential Therapeutic Target in Prostate Cancer," Apr. 2009.
International Search Report and Written Opinion dated Sep. 3, 2019 for corresponding International Application No. PCT/US2019/035205.
Yang et al., "Identification of CD24 as a Cancer Stem Cell Marker in Human Nasopharyngeal Carcinoma," PLoS One, Jun. 23, 2014, vol. 9, No. 6, pp. 1-14.
Han et al., "Cancer Stem Cells: Therapeutic Implications and Perspectives in Cancer Therapy," Acta Pharmaceutica Sinica B; Apr. 2013, vol. 3, No. 2, pp. 65-75.

(Continued)

Primary Examiner — Thea D'Ambrosio
(74) Attorney, Agent, or Firm — Nevrivy Patent Law Group P.L.L.C.

(57) ABSTRACT

The present invention relates to the use of a CD24 protein for preventing or treating relapse of a cancer in a subject. The present invention also relates to the use of a CD24 protein for reducing cancer stem cell activity.

16 Claims, 30 Drawing Sheets
Specification includes a Sequence Listing.

(56) References Cited

OTHER PUBLICATIONS

Bretz et al., "CD24 promotes tumor cell invasion by suppressing tissue factor pathway inhibitor-2 (TFPI-2) in a c-Src-dependent fashion," Clin Exp Metastatis (2012) 29, pp. 27-38.
Toubai et al., "Siglec-G-CD24 axis controls the severity of graft-versus-host disease in mice," Blood, May 29, 2014, vol. 123, No. 22, pp. 3512-3523.
Communication pursuant to Rules 70(2) and 70a(2) EPC, EP 19815874.3, Mar. 9, 2022, 11 pages.

\* cited by examiner

FIG. 1A

<u>MGRAMVARLGLGLLLLALLLPTQIYS</u>**SETTTGTSSNSSQSTSNSGLAP
NPTNATTK**PKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 1B

<u>MGRAMVARLGLGLLLLALLLPTQIYS</u>**SETTTGTSSNSSQSTSNSGLAP
NPTNATTK<u>V</u>**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 1C

<u>MGRAMVARLGLGLLLLALLLPTQIYS</u>**SETTTGTSSNSSQSTSNSGLAP
NPTNATTK<u>A</u>**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 2

```
Mouse CD24 NQTSVAPFPGN--QNISAS----PNPTNATTRG
           _*  _      *   * * *    ********__
Human CD24 SETTTGTSS-NSSQSTSNS-GLAPNPTNATTKA(V)
```

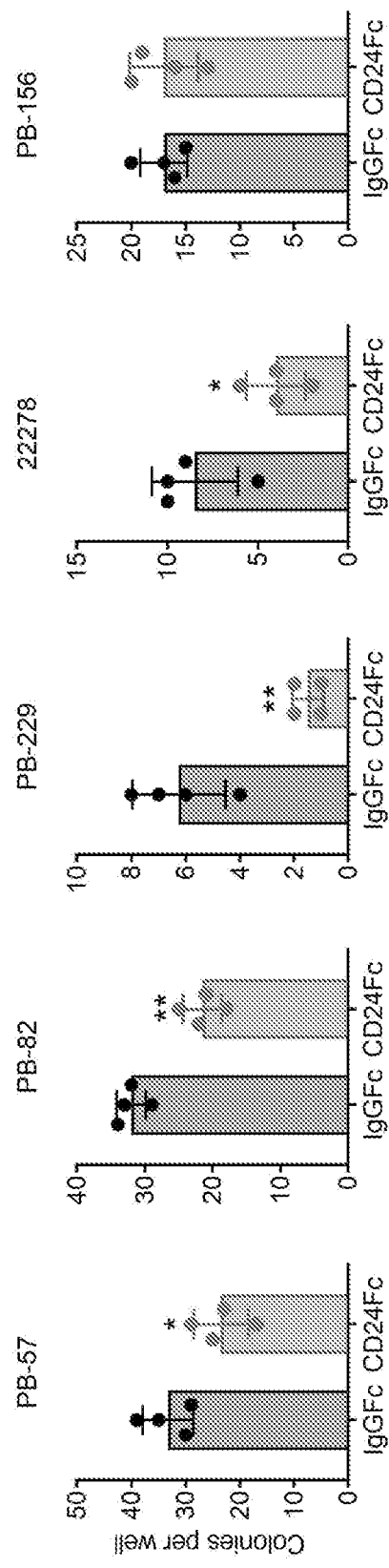
FIG. 27A AML samples
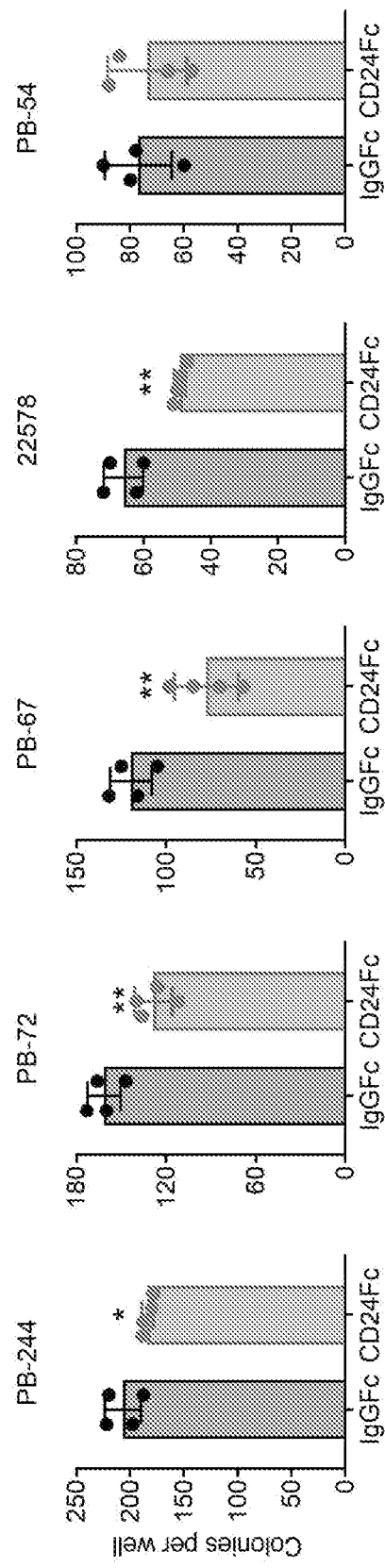
FIG. 27B CML samples

SEQUENCE LISTING

```
<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: VARIANT
<222> LOCATION: (31)...(31)
<223> OTHER INFORMATION: Valine or Alanine

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 2
<211> LENGTH: 30
<212> TYPE: PRT
<213> ORGANISM: Homo sapiens

<400> SEQUENCE: 2
```

```
Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
```

```
                180                 185                 190
Pro Ser Arg Asp Glu Leu Thr Lys Asn Gln Val Ser Leu Thr Cys Leu
            195                 200                 205

Val Lys Gly Phe Tyr Pro Ser Asp Ile Ala Val Glu Trp Glu Ser Asn
210                 215                 220

Gly Gln Pro Glu Asn Asn Tyr Lys Thr Thr Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
```

260

<210> SEQ ID NO 7
<211> LENGTH: 231
<212> TYPE: PRT
<213> ORGANISM: Homo sapiens

<400> SEQUENCE: 7

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 8
<211> LENGTH: 288
<212> TYPE: PRT
<213> ORGANISM: Artificial
<220> FEATURE:
<223> OTHER INFORMATION: Fusion protein

<400> SEQUENCE: 8

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Val Pro Lys Ser Cys Asp Lys Thr
    50                  55                  60

His Thr Cys Pro Pro Cys Pro Ala Pro Glu Leu Leu Gly Gly Pro Ser
65                  70                  75                  80
```

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 9
<211> LENGTH: 288
<212> TYPE: PRT
<213> ORGANISM: Artificial
<220> FEATURE:
<223> OTHER INFORMATION: Fusion protein

<400> SEQUENCE: 9

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Pro Lys Ser Cys Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

```
Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 10
<211> LENGTH: 29
<212> TYPE: PRT
<213> ORGANISM: Macaca fascicularis

<400> SEQUENCE: 10

Thr Val Thr Thr Ser Ala Pro Leu Ser Ser Asn Ser Pro Gln Asn Thr
1               5                   10                  15

Ser Thr Thr Pro Asn Pro Ala Asn Thr Thr Lys Ala
            20                  25

<210> SEQ ID NO 11
<211> LENGTH: 262
<212> TYPE: PRT
<213> ORGANISM: Artificial
<220> FEATURE:
<223> OTHER INFORMATION: Fusion protein

<400> SEQUENCE: 11

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Val Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160
```

```
Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240
```

```
Ser Val Met His Glu Ala Leu His Asn His Tyr Thr Gln Lys Ser Leu
                245                 250                 255
Ser Leu Ser Pro Gly Lys
            260
```

METHODS OF USE OF CD24 FOR THE PREVENTION AND TREATMENT OF LEUKEMIA RELAPSE

STATEMENT REGARDING FEDERALLY SPONSORED RESEARCH OR DEVELOPMENT

This invention was made in part with Government support under NIH/NCI SBIR Grant Number R44CA221513. The Government has certain rights in this invention.

FIELD OF THE INVENTION

The present invention relates to compositions and methods for preventing and treating leukemia relapse.

BACKGROUND OF THE INVENTION

Graft vs host disease (GVHD) is a life threatening complication that occurs when the immune competent cells in a tissue graft mount an immune attack against the host. GVHD is most commonly associated with hematopoietic cell transplantation (HCT) for the treatment of hematologic malignancies. Activated donor T cells damage host epithelial cells following an inflammatory cascade that begins with the preparative regimen. The exact risk is dependent on the stem cell source, age of the patient, conditioning, and GVHD prophylaxis used. The incidence is directly related to the degree of human leukocyte antigens (HLA) disparity. The median onset of acute GVHD is typically 21 to 25 days after transplantation. The incidence ranges from 30-65% in recipients of fully histocompatible related donor transplants to 60% to 80% in recipients of mismatched hematopoietic cells or hematopoietic cells from an unrelated donor. Umbilical cord-blood transplantation has been associated with slower neutrophil recovery with lower incidence and later onset of acute GVHD. Factors that increase the incidence include use of peripheral blood rather than bone marrow as the source of hematopoietic cells and older recipient age. The median time of diagnosis of chronic GVHD is 4.5 months after HLA-identical sibling transplantation and 4 months after unrelated donor transplantation. De novo chronic GVHD almost never occurs after 2 years following allogeneic HCT.

For over 20 years, the combination of a calcineurin inhibitor (e.g. cyclosporine and tacrolimus) with methotrexate has remained the standard of care for the prevention of GVHD. Despite routine administration of immune prophylaxis, clinically significant GVHD (Grade II-IV) occurs in approximately 30 to 65% of patients undergoing HLA matched related HCT and 60 to 80% of patients receiving unrelated donor HCT. Acute GVHD is an early event after HCT, with a median time to onset of approximately 25 to 30 days. In patients with very severe GVHD, mortality rates exceed 90%. One explanation for this is that, once established, ineffective responses occur to front-line therapy with high dose corticosteroids in greater than 50% of patients. Survival is significantly diminished for patients who demonstrate steroid refractoriness or who require prolonged treatment. Even when successful, high doses of corticosteroids are a major source of morbidity due to increased infections and deconditioning that places patients at significant risk for TRM.

Host tissue injuries caused by the HCT conditioning regimens, including high-dose chemotherapy and/or total body irradiation (TBI), are considered to be the first step in the development of acute GVHD. Host tissue injuries caused by the conditioning regimen lead to the release of proinflammatory cytokines (such as TNF-α, IL-1β and IL-6), and also the release of damage-associated molecular patterns (DAMPs) and pathogen-associated molecular patterns (PAMPs). Both DAMPs and PAMPs can activate antigen-presenting cells (APCs), such as dendritic cells (DCs), by binding to pattern recognition receptors (PRRs). The host APCs subsequently activate donor T cells and an immunologic cascade that results in the release of pro-inflammatory cytokines and expansion of the antigen specific allo-reactive T cells that target host tissues, resulting in GVHD. It is therefore of great interest to explore whether GVHD can be attenuated by targeting host response to tissue injuries and preventing activation of APCs, the key processes in the initiation of GVHD.

To date, treatment and prevention of GVHD has predominantly focused on either pharmacologic inhibition or depletion of T cells through in vivo or ex vivo approaches to limit expansion of alloreactive T cells that mediate tissue injury. While non-selective T-cell depleting strategies (e.g. antithymocyte globulin) are efficacious in preventing GVHD, they do not improve survival due to offsetting risks for relapse, infection and graft rejection. Conversely, more selective inhibition by targeting single pro-inflammatory cytokines has not demonstrated clinical benefit in treating GVHD. As a result, apart from antibodies that deplete T cells, no biologics have been approved for GVHD and the combination of tacrolimus with methotrexate has remained the standard of care for the prevention of GVHD. The significant unmet medical needs call for more selective biological products for both prophylaxis and treatment of GVHD and relapse of leukemia.

SUMMARY OF THE INVENTION

Provided herein is a method of preventing or treating relapse of a cancer in a subject in need thereof, which may comprise administering a CD24 protein to the subject. Further provided herein is use of a CD24 protein in the manufacture of a medicament for preventing or treating relapse of a cancer in a subject. Also provided herein is a method of reducing cancer stem cell activity in a subject in need thereof, which may comprise administering a CD24 protein to the subject. Further provided herein is use of a CD24 protein in the manufacture of a medicament for reducing cancer stem cell activity in a subject. Reducing cancer stem cell activity may prevent or treat at least one of relapse and metastasis of a cancer of the subject.

The cancer stem cell may be a leukemia cancer stem cell. The subject may undergo or may have undergone a hematopoietic stem cell transplantation (HCT). The subject may have cancer. The cancer or cancer stem cell may be Acute Myeloid Leukemia (AML), Acute Lymphoblastic Leukemia (ALL), Chronic Myelogenous Leukemia (CML), Myelodysplastic syndrome (MDS), or Chronic Myelomonocytic Leukemia (CMML).

The CD24 protein may be administered at a dose of 240 mg or 480 mg. The CD24 protein may be administered before or after the HCT, and may be administered one day before the HCT. The CD24 protein may be administered more than once, and may be administered in biweekly doses. The doses may comprise a dose on the day before the HCT, a dose on day 14 after the HTC, and a dose on day 28 after the HCT, and the doses may be, respectively, 480 mg, 240 mg, and 240 mg.

The CD24 protein may comprise a mature human CD24 polypeptide fused at its N-terminus or C-terminus to a Fc region of a mammalian immunoglobulin (Ig) protein. The mature human CD24 polypeptide may comprise the sequence set forth in SEQ ID NO: 1 or 2. The Ig protein may be human. The Fc region may comprise a hinge region and CH2 and CH3 domains of IgG1, IgG2, IgG3, IgG4, or IgA. The Fc region may comprise a hinge region and CH2, CH3 and CH4 domains of IgM. The CD24 protein may comprise the sequence set forth in SEQ ID NO: 6, 11, or 12. The amino acid sequence of the CD24 protein may consist of the sequence set forth in SEQ ID NO: 6, 11, or 12. The CD24 protein may be soluble, and may be glycosylated. The CD24 protein may be prepared using a eukaryotic expression system, which may comprise expression from a vector in mammalian cells. The cells may be Chinese Hamster Ovary cells.

BRIEF DESCRIPTION OF THE DRAWINGS

FIG. 1A shows the amino acid composition of the full length CD24 fusion protein, CD24Fc (also referred to herein as CD24Ig) (SEQ ID NO: 5). The underlined 26 amino acids are the signal peptide of CD24 (SEQ ID NO: 4), which are cleaved off during secretion from a cell expressing the protein and thus missing from the processed version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 7). FIG. 1B shows the sequence of $CD24^VFc$ (SEQ ID NO: 8), in which the mature human CD24 protein (bold) is the valine polymorphic variant of SEQ ID NO: 1. FIG. 1C shows the sequence of $CD24^AFc$ (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

FIG. 2 shows amino acid sequence variations between mature CD24 proteins from mouse (SEQ ID NO: 3) and human (SEQ ID NO: 2). The potential O-glycosylation sites are bolded, and the N-glycosylation sites are underlined.

FIG. 3A. i.v. injection of 1 mg CD24IgG1. FIG. 3B. s.c. injection of 1 mg CD24IgG1 (CD24Fc). FIG. 3C. Comparison of the total amounts of antibody in the blood as measured by areas under curve (AUC), half-life and maximal blood concentration. Note that overall, the AUC and Cmax of the s.c. injection is about 80% of i.v. injection, although the difference is not statistically significant.

FIG. 4A. Host response to PAMP was unaffected by CD24-Siglec G(10) interaction. FIG. 4B. CD24-Siglec G (10) interaction represses host response to DAMP, possibly through the Siglec G/10-associated SHP-1.

FIG. 5A. Affinity measurement of the CD24Fc-Siglec 10 interaction. FIG. 5B. CD24Fc specifically interacts with HMGB-1 in a cation-dependent manner. CD24Fc was incubated with HMGB1 in 0.1 mM of $CaCl_2$ and $MgCl_2$, in the presence or absence of the cation chelator EDTA. CD24Fc is pulled down with protein G-beads, and the amounts of HMGB1, CD24Fc or control Fc is determined by Western blot. FIG. 5C. CD24Fc activates mouse Siglec G by inducing Tyrosine phosphorylation (middle panel) and association with SHP-1 (upper panel). The amounts of Siglec G are shown in the lower panel. $CD24^{-/-}$ spleen cells were stimulated with 1 µg/ml of CD24Fc, control Fc or vehicle (PBS) control for 30 minutes. Siglec G was then immunoprecipitated and probed with anti-phospho-tyrosine or anti-SHP-1.

FIG. 7A. ShRNA silencing of CD24 leads to spontaneous production of TNF-α, IL-1β, and IL-6. THP1 cells were transduced with lentiviral vectors encoding either scrambled or two independent CD24 shRNA molecules. The transduced cells were differentiated into macrophages by culturing for 4 days with PMA (15 ng/ml). After washing away PMA and non-adherent cells, the cells were cultured for another 24 hours for measurement of inflammatory cytokines, by cytokine beads array. FIG. 7B. As in FIG. 7A, except that the given concentration of CD24Fc or control IgG Fc was added to macrophages in the last 24 hours. Data shown in FIG. 7A are means and S.D. from three independent experiments, while those in FIG. 7B are representative of at least 3 independent experiments.

FIG. 22A Plot of Mean (±Standard Deviation) Plasma CD24Fc Concentration (ng/mL) Versus Time on a Linear Scale. FIG. 22B. Plot of Mean (±Standard Deviation) Plasma CD24Fc Concentration (ng/mL) Versus Time on a Semi-Logarithmic Scale.

FIG. 23A Plot of Mean (±Standard Deviation) Plasma CD24Fc Concentration (ng/mL) Versus Time on a Linear Scale. FIG. 23B. Plot of Mean (±Standard Deviation) Plasma CD24Fc Concentration (ng/mL) Versus Time on a Semi-Logarithmic Scale.

FIG. 25A, quantification of colony formation in THP-1 cells treated with CD24Fc or IgG Fc control. FIG. 25B. Representative images of colony formation assay in the 4th round replating of THP-1 cells treated with CD24Fc or IgG Fc. The scale bar represents 1 mm. Data represent mean±SEM.

FIGS. 27A-B, show the effects of CD24Fc as compared to control (IgGFc) on leukemia cells from primary AML (FIG. 278A) and CML (FIG. 27B). Colony formation assays were carried out by plating 500-1000 cells of different cell lines in methylcellulose medium with CD24Fc or IgG (100 μg/ml). The colony numbers were scored 7-14 days later. Data represented are means±SEM.

DETAILED DESCRIPTION

Figure 3:
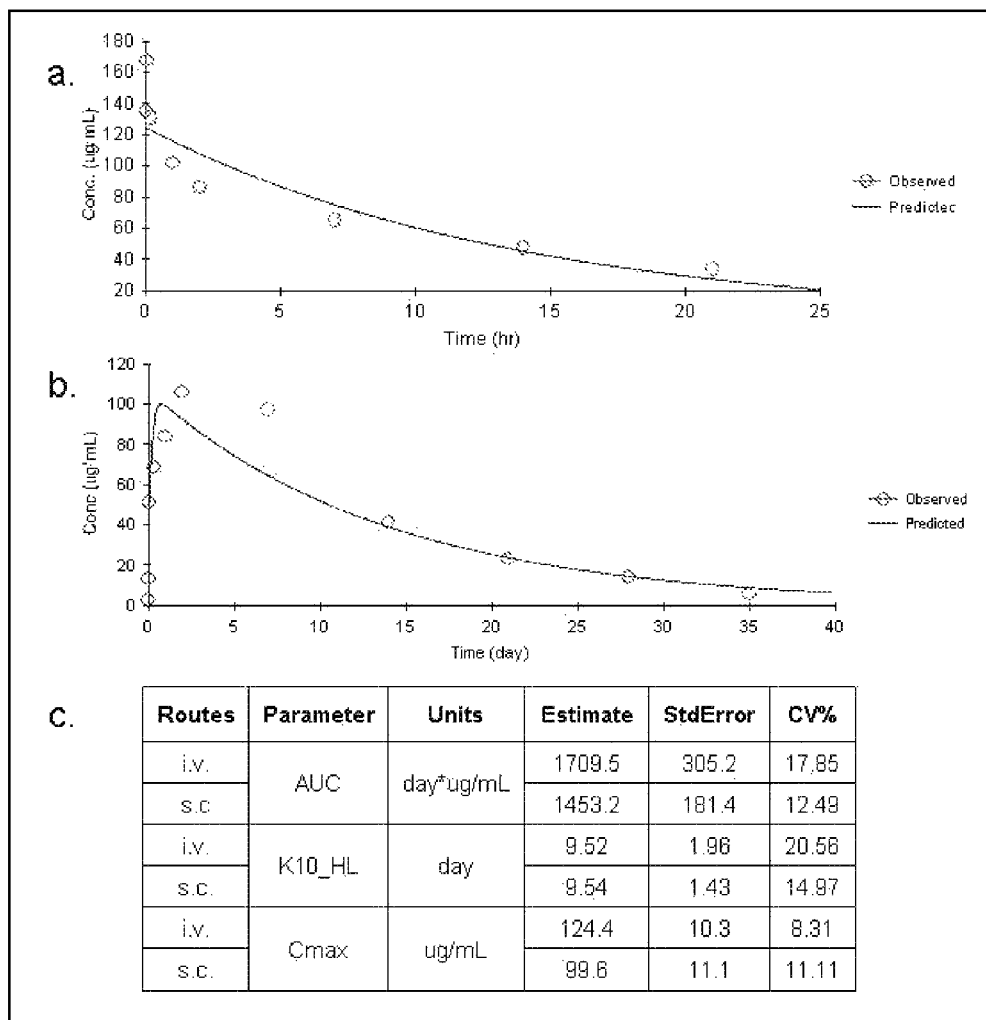
FIGS. 3A-C. WinNonlin compartmental modeling analysis of pharmacokenitics of CD24IgG1 (CD24Fc). The opened circles represent the average of 3 mice, and the line is the predicted pharmacokinetic curve.

Tissue damage can lead to the release of proinflammatory cytokines (such as TNF-α, IL-1β and IL-6), and also the release of damage-associated molecular patterns (DAMPs) and pathogen-associated molecular patterns (PAMPs). Both DAMPs and PAMPs can activate antigen-presenting cells (APCs), such as dendritic cells (DCs), by binding to pattern recognition receptors (PRRs). The host APCs subsequently activate donor T cells and an immunologic cascade that results in the release of pro-inflammatory cytokines and expansion of the antigen specific allo-reactive T cells that target host tissues. It is these events that lead to the development of GVHD and exacerbate the effects of mucositis. For example, RIOM starts as an acute inflammation of oral mucosa, tongue and pharynx following radiotherapy, which coincides with recruitment of various inflammatory cells and release of inflammatory cytokines, chemotactic mediators, and growth factors.

The involvement of tissue damage in mucositis and GVHD raised the prospect that negatively regulating host response to DAMPs by CD24Fc can be explored for GVHD therapy. The inventors' preclinical studies have demonstrated that CD24Fc specifically targets DAMP-mediated inflammation and prevents GVHD in mouse models, including a humanized mouse model. Importantly, the drug has advantages over conventional immunosuppressant as it does not cause general immune suppression and use of high doses of CD24Fc does not block antibody response in non-human primates. The data also demonstrate that CD24Fc prevents GVHD but preserves the graft versus leukemia (GVL) effect, making it an ideal drug for prophylaxis of GVHD in leukemia patients. Finally, the inventors' studies in non-human primate demonstrate that CD24Fc does not suppress antigen-specific immune response, which suggest that CD24Fc will not likely increase risk of infection.

The inventors have discovered that a soluble form of CD24 is highly effective for preventing Graft versus Host Disease (GVHD) and associated conditions such as mucositis, as well as for preventing leukemia relapse following HCT. The inventors have also discovered that CD24Fc produced a dose-dependent reduction in severe mucositis (grade ≥3) among patients receiving HCT therapy. These effects may be mediated through DAMPs. Pattern recognition is involved in inflammatory response triggered by both PAMPs and DAMPs. The inventors have realized that recent studies have demonstrated that an exacerbated host response to DAMPs may play a part in the pathogenesis of inflammatory and autoimmune disease. DAMPs were found to promote the production of inflammatory cytokines and autoimmune diseases and in animal models, and inhibitors of DAMPs such as HMGB1 and HSP90 were consequently found to ameliorate rheumatoid arthritis (RA). TLRs, RAGE-R, DNGR (encoded by Clec9A), and Mincle have been shown to be receptors responsible for mediating inflammation initiated by a variety of DAMPs.

The inventors' recent work demonstrated that CD24-Siglec G interactions discriminate innate immunity to DAMPs from PAMPs. Siglec proteins are membrane-associated immunoglobulin (Ig) superfamily members that recognize a variety of sialic acid-containing structures. Most Siglecs have an intra-cellular immune-tyrosine inhibitory motif (ITIM) that associates with SHP-1, -2 and Cbl-b to control key regulators of inflammatory responses. The inventors have reported CD24 as the first natural ligand for a Siglec, Siglec G in mouse and Siglec 10 in human. Siglec G interacts with sialylated CD24 to suppress the TLR-mediated host response to DAMPs, such as HMGB1, via a SHP-1/2 signaling mechanism.

Human CD24 is a small GPI-anchored molecule encoded by an open-reading frame of 240 base pairs in the CD24 gene. Of the 80 amino acids, the first 26 constitute the signal peptide, while the last 23 serve as a signal for cleavage to allow for the attachment of the GPI tail. As a result, the mature human CD24 molecule has only 31 amino acids. One of the 31 amino acids is polymorphic among the human population. A C to T transition at nucleotide 170 of the open-reading frame results in the substitution of Alanine (A) with Valine (V) at residue 31 of the mature protein. Since this residue is immediately N-terminal to the cleavage site, and since the replacement is nonconservative, these two alleles may be expressed at different efficiencies on the cell surface. Indeed, transfection studies with cDNA demonstrated that the $CD24^v$ allele is more efficiently expressed on the cell surface. Consistent with this, $CD24^{v/v}$ PBL expressed higher levels of CD24, especially on T cells.

The inventors have demonstrated that CD24 negatively regulates host response to cellular DAMPs that are released as a result of tissue or organ damage, and at least two overlapping mechanisms may explain this activity. First, CD24 binds to several DAMPs, including HSP70, HSP90, HMGB1 and nucleolin and represses host response to these DAMPs. To do this, it is presumed that CD24 may trap the inflammatory stimuli to prevent interaction with their receptors, TLR or RAGE. Second, using an acetaminophen-induced mouse model of liver necrosis and ensuring inflammation, the inventors demonstrated that through interaction with its receptor, Siglec G, CD24 provides a powerful negative regulation for host response to tissue injuries. To achieve this activity, CD24 may bind and stimulate signaling by Siglec G wherein Siglec G-associated SHP1 triggers the negative regulation. Both mechanisms may act in concert as mice with targeted mutation of either gene mounted much stronger inflammatory response. In fact, DC cultured from bone marrow from either $CD24^{-/-}$ or Siglec $G^{-/-}$ mice produced higher levels of inflammatory cytokines when stimulated with either HMGB1, HSP70, or HSP90. To the inventors' knowledge, CD24 is the only inhibitory DAMP receptor capable of shutting down inflammation triggered by DAMPs and no drug is currently available that specifically targets host inflammatory response to tissue injuries. Furthermore, the inventors have demonstrated the ability of exogenous soluble CD24 protein to alleviate DAMP-mediated autoimmune disease using mouse models of RA, MS and GvHD.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554, 101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise a mature CD24 or a variant thereof. Mature CD24 corresponds to the extracellular domain (ECD) of CD24. The mature CD24 may be from a human or another mammal. As described above, mature human CD24 protein is 31 amino acids long and has a variable alanine (A) or valine (V) residue at its C-terminal end. The mature CD24 protein may comprise the following sequence:

SETTTGTSSNSSQSTSNSGLAPNPTNATTK(V/A) (SEQ ID NO: 1)

The C-terminal valine or alanine may be immunogenic and may be omitted from the CD24 protein, which may reduce its immunogenicity. Therefore, the CD24 protein may comprise the amino acid sequence of mature human CD24 lacking the C-terminal amino acid:

SETTTGTSSNSSQSTSNSGLAPNPTNATTK (SEQ ID NO: 2)

Despite considerable sequence variations in the amino acid sequence of the mature CD24 proteins from mouse and human, they are functionally equivalent, as human CD24Fc has been shown to be active in the mouse. The amino acid sequence of the human CD24 ECD shows some sequence conservation with the mouse protein (39% identity; Genbank accession number NP_033976). However, it is not that surprising that the percent identity is not higher as the CD24 ECD is only 27-31 amino acids in length, depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63% (FIG. 2). As a result of sequence conservation between mouse and human CD24 primarily in the C-terminus and in the abundance of glycosylation sites, significant variations in the mature CD24 proteins may be tolerated in using the CD24 protein, especially if those variations do not affect the conserved residues in the C-terminus or do not affect the glycosylation sites from either mouse or human CD24. Therefore, the CD24 protein may comprise the amino acid sequence of mature murine CD24:

NQTSVAPFPGNQNISASPNPTNATTRG (SEQ ID NO: 3).

The amino acid sequence of the human CD24 ECD shows more sequence conservation with the cynomolgus monkey protein (52% identity; UniProt accession number UniProtKB—I7GKK1) than with mouse. Again, this is not surprising given that the percent identity is not higher as the ECD is only 29-31 amino acids in length in these species, and the role of sugar residues in binding to its receptor(s). The amino acid sequence of cynomolgous Siglec-10 receptor has not been determined but the amino acid sequence identity between the human and rhesus monkey Siglec-10 (GenBank accession number XP_001116352) proteins is 89%. Therefore, the CD24 protein may also comprise the amino acid sequence of mature cynomolgous (or rhesus) monkey CD24:

TVTTSAPLSSNSPQNTSTTPNPANTTTKA (SEQ ID NO: 10)

The CD24 protein may be soluble. The CD24 protein may further comprise an N-terminal signal peptide, which may allow secretion of the protein from a cell expressing the protein. The signal peptide sequence may comprise the amino acid sequence MGRAMVARLGLGLLL-LALLLPTQIYS (SEQ ID NO: 4). Alternatively, the signal sequence may comprise any of those that are found on other transmembrane or secreted proteins, or those modified from the existing signal peptides known in the art.

a. Fusion

The CD24 protein may be fused at its N- or C-terminal end to a protein tag, which may comprise a portion of a mammalian Ig protein, which may be human or mouse or from another species. The portion may comprise an Fc region of the Ig protein. The Fc region may comprise at least one of the hinge region, CH2, CH3, and CH4 domains of the Ig protein. The Ig protein may be human IgG1, IgG2, IgG3, IgG4, or IgA, and the Fc region may comprise the hinge region, and CH2 and CH3 domains of the Ig. The Fc region may comprise the human immunoglobulin G1 (IgG1) isotype SEQ ID NO: 7. The Ig protein may also be IgM, and the Fc region may comprise the hinge region and CH2, CH3, and CH4 domains of IgM. The protein tag may be an affinity tag that aids in the purification of the protein, and/or a solubility-enhancing tag that enhances the solubility and recovery of functional proteins. The protein tag may also increase the valency of the CD24 protein. The protein tag may also comprise GST, His, FLAG, Myc, MBP, NusA, thioredoxin (TRX), small ubiquitin-like modifier (SUMO), ubiquitin (Ub), albumin, or a Camelid Ig. Methods for making fusion proteins and purifying fusion proteins are well known in the art.

Based on preclinical research, for the construction of the fusion protein CD24Fc identified in the examples, the truncated form of native CD24 molecule of 30 amino acids, which lacks the final polymorphic amino acid before the GPI signal cleavage site (that is, a mature CD24 protein having SEQ ID NO: 2), has been used. The mature human CD24 sequence is fused to a human IgG1 Fc domain (SEQ ID NO: 7). The sequence of the full length CD24Fc fusion protein is provided in SEQ ID NO: 5 (FIG. 1A), and the sequence of the processed version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise the amino acid sequence set forth in SEQ ID NO: 11 or 12.

b. Production

The CD24 protein may be heavily glycosylated, and may be involved in functions of CD24 such as costimulation of immune cells and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™.

c. Pharmaceutical Composition

The CD24 protein may be contained in a pharmaceutical composition, which may comprise a pharmaceutically acceptable amount of the CD24 protein. The pharmaceutical composition may comprise a pharmaceutically acceptable carrier. The pharmaceutical composition may comprise a solvent, which may keep the CD24 protein stable over an extended period. The solvent may be PBS, which may keep the CD24 protein stable for at least 66 months at −20° C.

(−15~−25° C.). The solvent may be capable of accommodating the CD24 protein in combination with another drug.

The pharmaceutical composition may be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The pharmaceutical composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example). A formulation for subcutaneous injection may be particularly relevant for an indication like lupus and its associated manifestations and complications.

3. Methods of Treatment a. GVHD

Provided herein is a method of preventing, mitigating or treating Graft versus Host Disease (GVHD) in a subject in need thereof by administering the CD24 protein to the subject. The subject may have or be at risk of developing GVHD. The subject may undergo or may be undergoing hematopoietic stem cell transplantation (HCT). The CD24 protein may be used prophylactically to prevent GVHD in a subject undergoing HCT. The GVHD may be acute GVHD. The CD24 protein may reduce the subject's risk of grade III-IV acute GVHD.

The subject may have a cancer. The cancer may be Acute Myeloid Leukemia (AML), Acute Lymphoblastic Leukemia (ALL), Chronic Myelogenous Leukemia (CML), Myelodysplastic syndrome (MDS), or Chronic Myelomonocytic Leukemia (CMML).

b. Relapse of Cancer

Further provided herein is a method of reducing the risk of or preventing relapse of a cancer in a subject who will undergo or has undergone HCT, by administering the CD24 protein to the subject. The cancer may be a leukemia described herein.

The HCT may be an allogeneic myeloablative HCT. The subject may be a mammal. The mammal may be a monkey or an ape. The subject may be a human.

c. Reducing Cancer Stem Cell Activity

Provided herein is a method of reducing or suppressing cancer stem cell activity, which may be in vivo. The method may comprise contacting cancer stem cells with the CD24 protein. The method may also comprise administering the CD24 protein to a subject in need thereof disclosed herein. The cancer stem cell may be from a cancer described herein, and in particular may be a leukemia cancer stem cell. Suppression or reduction of cancer stem cell activity may reduce the subject's risk of, or prevent, relapse of a cancer described herein. The suppression or reduction of cancer stem cell activity may also reduce the subject's risk of, or prevent, metastasis of the cancer.

d. Medicaments

Also provided are uses of the CD24 protein in the manufacture of a medicament for uses as described herein.

e. Dose Regimen

The dose of the CD24 protein administered may be 0.01 mg/kg to 1000 mg/kg, and may be 1 to 500 mg/kg, depending on the desired effect on GVHD and the route of administration. The CD24 protein may be administered by intravenous (IV) infusion or by subcutaneous, intramural (that is, within the wall of a cavity or organ), or intraperitoneal injection. The dose may be 10-1000 mg, 10-500 mg, 240 mg, or 480 mg, which in particular may be suitable where the subject is a human.

The CD24 protein may be administered before or after the stem cell transplant. The CD24 protein may be administered 1-4 days, particularly 1 day, before the stem cell transplant. The CD24 protein may also be administered in multiple doses before or after stem cell transplant. The CD24 protein may be administered in 2, 3, 4, 5 or 6 bi-weekly doses. Each dose of the CD24 protein may be 240 mg or 480 mg. A first dose may be administered on day −4 to day 0 relative to the day of stem cell transplant (day 0), and may be administered on day −1 in particular. Each subsequent dose may be administered every 9-19 or 11-17 days thereafter. A second dose may be administered on day +9 to +19 or day +11 to +17, particularly day +14, relative to the day of stem cell transplant. A third dose may be administered on day +18 to +38, day +23 to +33, or day +22 to +34, particularly day +28, relative to the day of stem cell transplant. In particular, the CD24 protein may be administered in three biweekly administrations of 480 mg, 240 mg, and 240 mg, respectively on day −1, day +14 and day +28 relative to the day of stem cell transplant. The CD24 protein may in particular be CD24Fc.

f. Combination Treatment

The CD24 protein may be administered to the subject in combination with standard of care GVHD prophylaxis. The standard of care GVHD prophylaxis may comprise administration of methotrexate plus calcineurin inhibitor, such as tacrolimus (Prograf, FK506) or cyclosporine (Sandimmune, Neoral). Tacrolimus may be administered on day −3 relative to the day of stem cell transplant, and may be administered by IV or PO (orally). For IV dosing as a continuous infusion the starting dose may be 0.03 mg/kg/day based on adjusted body weight. For oral dosing the starting dose may be 0.045 mg/kg/dose twice daily. If the subject cannot tolerate tacrolimus, then cyclosporine may be administered to the subject by IV at a dose of 100× the IV tacrolimus dose (e.g., 3 mg/kg/day starting dose). The cyclosporine may also be administered orally at a dose of 3× the IV dose. When Neoral brand is used, because of greater bioavailability, the cyclosporine may be administered orally at 2× the IV dose.

In the absence of GVHD, tacrolimus levels may be monitored for therapeutic dosing only during the first 100 days post-transplant. The therapeutic target trough level for tacrolimus may be 5-15 ng/mL. Tacrolimus levels may be monitored at a minimum of three times (e.g. every 48-72 hours) for the first week post CD24 protein infusion (day 0 to day 7). In the absence of GVHD or relapse, tacrolimus tapering may begin on day +100 post-transplant. In the presence of GVHD, tacrolimus may be continued at the therapeutic dosing.

Methotrexate may be used in combination with tacrolimus for standard GVHD prophylaxis. Methotrexate may be administered intravenously at a dose of 15 mg/m$^2$/dose once daily on Day 1 after HCT, and at a dose of 10 mg/m$^2$/dose on days 3, 6, and 11 after HCT.

Example 1

CD24 Pharmacokinetics in Mice 1 mg of CD24Fc (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Fc was detected using a sandwich ELISA using purified anti-human CD24 (3.3 µg/ml) as the capturing antibody and peroxidase conjugated goat anti-human IgG Fc (5 µg/ml) as the detecting antibodies. As shown in FIG. 3a. The decay curve of CD24Fc revealed a typical biphase decay of the protein. The first biodistribution phase had a half-life of 12.4 hours. The second phase follows a model of first-order elimination from the central compartment. The half-life for the second phase was 9.54 days, which is similar to that of antibodies in vivo. These data suggest that the fusion protein is very stable in the blood stream. In another study in which the fusion protein was injected subcutaneously, an almost identical half-life of 9.52 days was observed (FIG. 3b). More importantly, while it took approximately 48 hours for the CD24Fc to reach peak levels in the blood, the total amount of the fusion protein in the blood, as measured by AUC, was substantially the same by either route of injection. Thus, from a therapeutic point of view, using a different route of injection should not affect the therapeutic effect of the drug. This observation greatly simplified the experimental design for primate toxicity and clinical trials.

Example 2

CD24-Siglec 10 Interaction in Host Response to Tissue Injuries

Nearly two decades ago, Matzinger proposed what was popularly called danger theory. In essence, she argued that the immune system is turned on when it senses the dangers in the host. Although the nature of danger was not well defined at the time, it has been determined that necrosis is associated with the release of intracellular components such as HMGB1 and Heat-shock proteins, which were called DAMP, for danger-associated molecular patterns. DAMP were found to promote production of inflammatory cytokines and autoimmune diseases. In animal models, inhibitors of HMGB1 and HSP90 were found to ameliorate RA. The involvement of DAMP raised the prospect that negative regulation for host response to DAMP can be explored for RA therapy.

Figure 4:
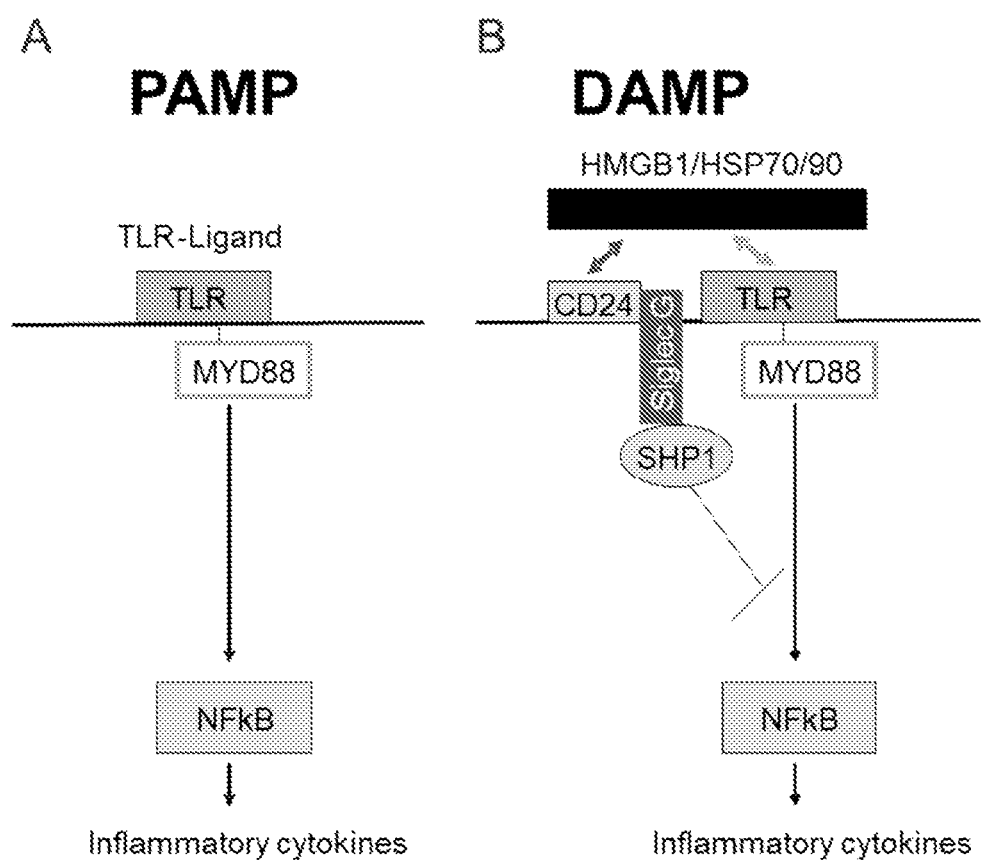
FIGS. 4A-B. CD24-Siglec G (10) interaction discriminates between PAMP and DAMP.

Using acetaminophen-induced liver necrosis and ensuring inflammation, it was observed that through interaction Siglec G, CD24 provides a powerful negative regulation for host response to tissue injuries. CD24 is a GPI anchored molecules that is broadly expressed in hematopoietic cells and other tissue stem cells. Genetic analysis of a variety of autoimmune disease in human, including multiple sclerosis, systemic lupus erythromatosus, RA, and giant cell arthritis, showed significant association between CD24 polymorphism and risk of autoimmune diseases. Siglec G is a member of I-lectin family, defined by their ability to recognize sialic acid containing structure. Siglec G recognized sialic acid containing structure on CD24 and negatively regulates production of inflammatory cytokines by dendritic cells. In terms of its ability to interact with CD24, human Siglec 10 and mouse Siglec G are functionally equivalent. However, it is unclear if there is a one-to-one correlation between mouse and human homologues. Although the mechanism remains to be fully elucidated, it is plausible that SiglecG-associated SHP1 may be involved in the negative regulation. These data lead to a new model in which CD24-Siglec G/10 interaction may play a critical in discrimination pathogen-associated molecular pattern (PAMP) from DAMP (FIG. 4).

At least two overlapping mechanisms may explain the function of CD24. First, by binding to a variety of DAMP, CD24 may trap the inflammatory stimuli to prevent their interaction with TLR or RAGE. This notion is supported by observations that CD24 is associated with several DAMP molecules, including HSP70, 90, HMGB1 and nucleolin. Second, perhaps after associated with DAMP, CD24 may stimulate signaling by Siglec G. Both mechanisms may act in concert as mice with targeted mutation of either gene mounted much stronger inflammatory response. In fact, DC cultured from bone marrow from either CD24−/− or Siglec G−/− mice produced much higher inflammatory cytokines when stimulated with either HMGB1, HSP70, or HSP90. In contrast, no effect were found in their response to PAMP, such as LPS and PolyI:C. These data not only provided a mechanism for the innate immune system to distinguish pathogen from tissue injury, but also suggest that CD24 and Siglec G as potential therapeutic targets for diseases associated with tissue injuries.

Example 3

CD24Fc Interacts with HMGB1, Siglec 10 and Induces Association Between Siglec G and SHP-1

Figure 5:
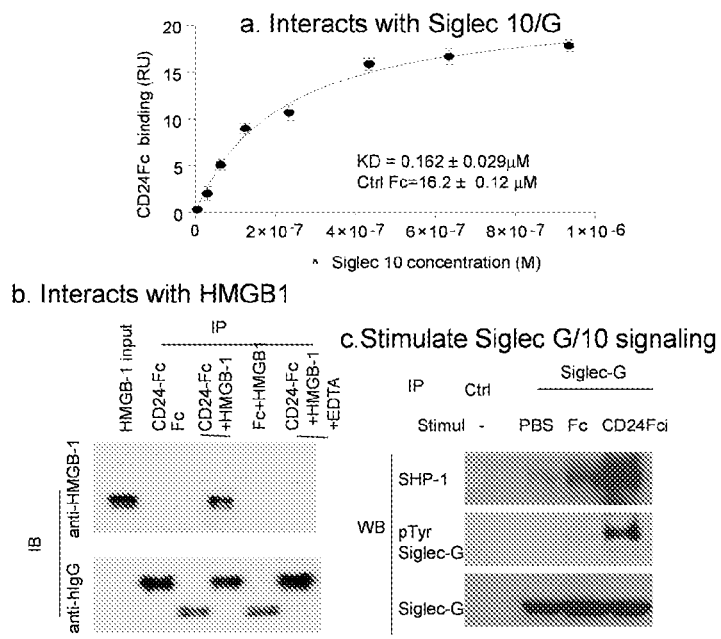
FIGS. 5A-C. CD24 Fc binds to Siglec 10 and HMGB1 and activates Siglec G, the mouse homologue of human Siglec 10.

To measure the interaction between CD24Fc and Siglec 10, we immobilized CD24Fc onto a CHIP and used Biacore to measure the binding of different concentrations of Siglec-10Fc. As shown in FIG. 5a, CD24Fc binds with Siglec 10 with a Kd of $1.6 \times 10^{-7}$M. This is 100-fold higher affinity than the control Fc. The interaction between CD24Fc and HMGB1 was confirmed by pull down experiments using CD24Fc-bound protein G beads followed by Western blot with either anti-IgG or anti-HMGB1. These data demonstrate that CD24Fc, but not Fc, binds to HMGB1 and that this binding is cation-dependent (FIG. 5b). To determine whether CD24Fc is an agonist of Siglec G, the mouse counterpart of human Siglec 10, we stimulated CD24−/− spleen cells with CD24Fc, control Fc or vehicle (PBS) control for 30 minutes. Siglec G was then immunoprecipitated and probed with anti-phospho-tyrosine or anti-SHP-1. As shown in FIG. 5c, CD24Fc induced substantial phosphorylation of Siglec G and association of SHP-1, a well-known inhibitor for both adaptive and innate immunity.

In vitro efficacy studies of CD24Fc.

Figure 6:
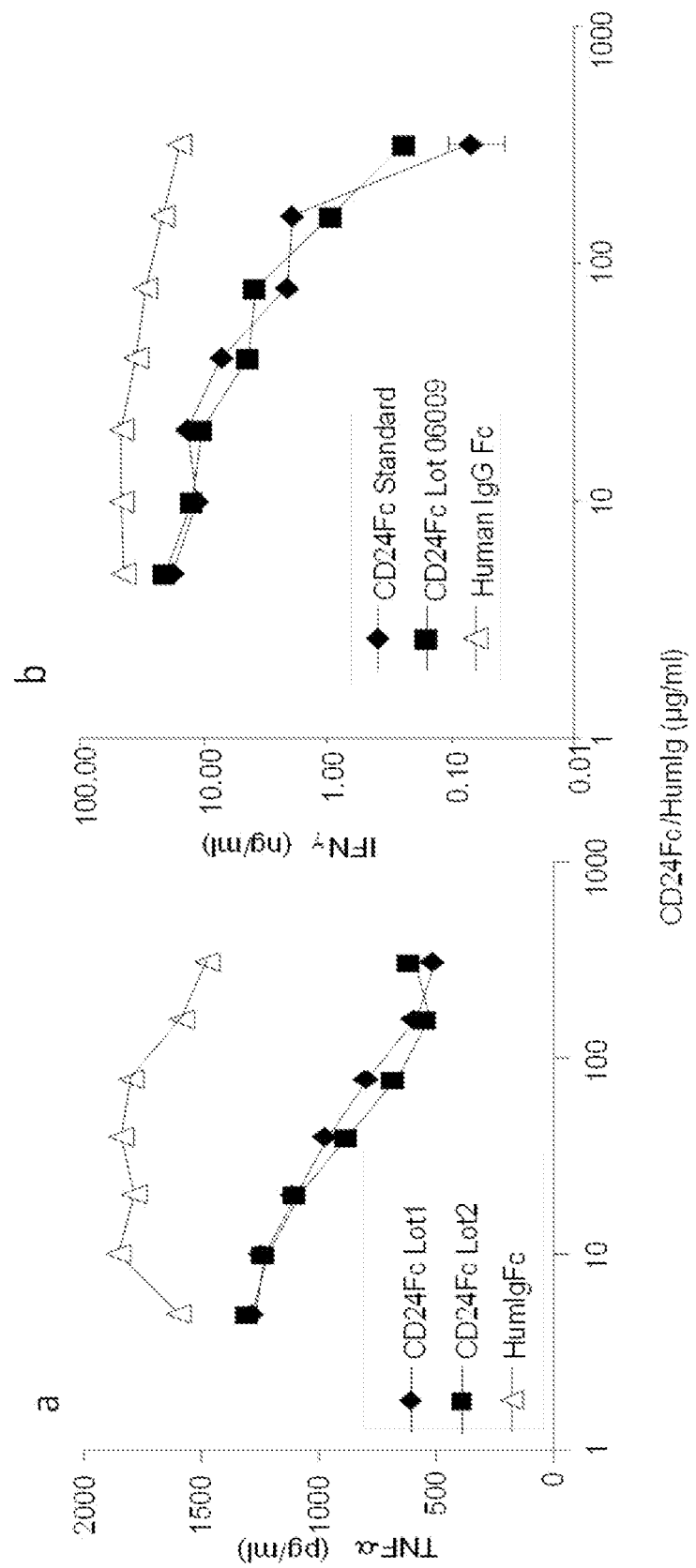
FIGS. 6A-B. CD24Fc inhibits production of TNF-α and IFN-γ by anti-CD3 activated human T cells. The human PBML were stimulated with anti-CD3 for 4 days in the presence or absence of CD24Fc and the amounts of IFN-γ and TNF-α released in the supernatant of cell culture were measured by ELISA. Data shown are means of triplicate. Error bar, SEM.

To study the impact of CD24Fc on the production of inflammatory cytokines by human T cells, the mature T cells in human PBML were activated by anti-CD3 antibody (OKT3), a commonly used agonist of the T cell receptor in the presence of different concentrations of CD24Fc or human IgG1 Fc. Four days later, the supernatants were collected and the production of IFN-γ and TNF-α were measured by Enzyme-linked immunosorbent assay (ELISA) to confirm activation. The results in FIG. 6 demonstrated that CD24Fc from two different manufacturing lots significantly reduced IFN-γ and TNF-α production from the activated human PBML compared with control IgG Fc control. In addition, when CD24Fc was added, cytokine production was inhibited in a dose-dependent manner. Therefore, CD24Fc can inhibit anti-CD3 induced human PBML activation in vitro. This study not only indicated the mechanism of action of CD24Fc might be through the inhibition of T cell activation, but also established a reliable bioassay for drug potency and stability testing.

Figure 7:
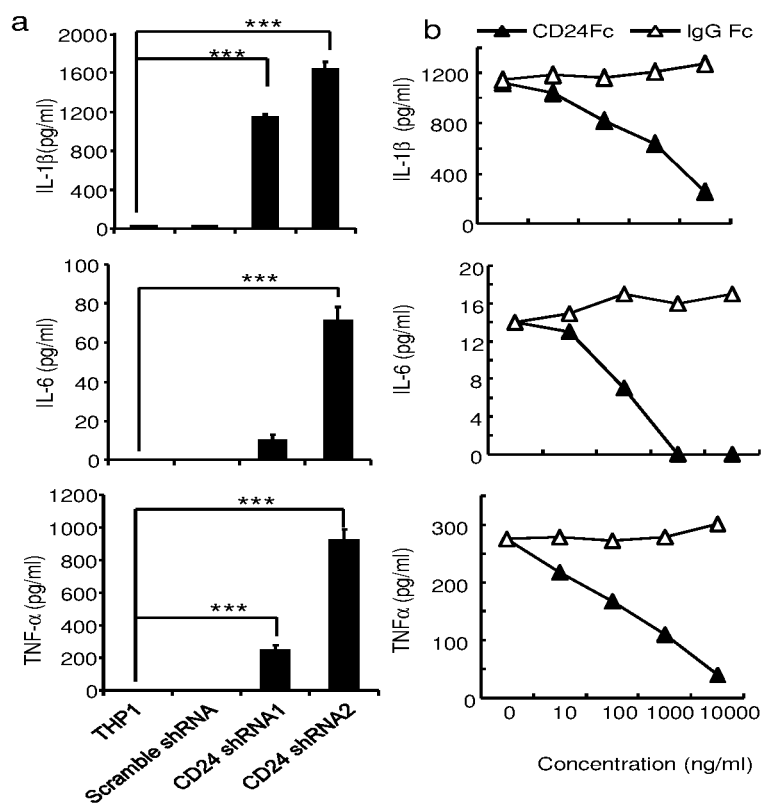
FIGS. 7A-B. CD24 inhibits inflammatory cytokine production by human macrophages.

To determine whether CD24Fc regulates production of inflammatory cytokines in a human cell line, we first silenced CD24 in the human acute monocytic leukemia THP1 cell line using RNAi, and then induced differentiation into macrophages by treating them with PMA. As shown in FIG. 7a, CD24 silencing substantially increased the production of TNFα, IL-1β and IL-6. These data demonstrate an essential role for endogenous human CD24 in limiting the production of inflammatory cytokines. Importantly, CD24Fc restored inhibition of TNFα in the CD24-silenced cell line (FIG. 7b), as well as IL-1β and IL-6. These data not only demonstrate the relevance of CD24 in inflammatory response of human cells, but also provides a simple assay to assess biological activity of CD24Fc.

Taken together, these data demonstrate that CD24Fc is capable of inhibiting cytokine production triggered by adaptive and innate stimuli. However, since the drug is much more effective in reducing cytokine production by innate effectors, we consider that the primary mechanism for its prophylactic function is to prevent inflammation triggered by tissue injuries at the early phase of transplantation.

Example 4

CD24 Pharmacokinetics in Humans

This example shows an analysis of the pharmacokinetics of a CD24 protein in humans. This was derived from a Phase I, randomized, double-blind, placebo-controlled, single ascending dose study to assess the safety, tolerability, and PK of CD24Fc in healthy male and female adult subjects. A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg. Succeeding cohorts received 30 mg, 60 mg, 120 mg, and 240 mg of CD24Fc or matching placebo and were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period:

The Screening Visit (Visit 1) occurred up to 21 days prior to the beginning of the active treatment period. After providing informed consent, subjects underwent screening procedures for eligibility.

Treatment Period:

Subjects were admitted to the Clinical Pharmacology Unit (CPU) on Day −1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-Up:

All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment: The total study duration for each subject was up to 63 days. Single-dose administration occurred on Day 1.

Number of Subjects:

Planned: 40 subjects

Screened: 224 subjects

Randomized: 40 subjects

Completed: 39 subjects

Discontinued: 1 subject

Diagnosis and Main Criteria for Inclusion: The population for this study was healthy males and females between the ages of 18 and 55 years, inclusive, with a body mass index between 18 kg/m$^2$ and 30 kg/m$^2$, inclusive.

Investigational Product and Comparator Information:

CD24Fc: single dose of 10 mg, 30 mg, 60 mg, 120 mg, or 240 mg administered via IV infusion; lot number: 09MM-036. CD24Fc was a fully humanized fusion protein consisting of the mature sequence of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL 0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Clinical laboratory evaluations (chemistry, hematology, and urinalysis) were summarized by treatment and visit. Change from baseline was also summarized. Vital signs (blood pressure, heart rate, respiratory rate, and temperature) were summarized by treatment and time point. Change from baseline was also summarized. All physical examination data were listed. Electrocardiogram parameters and the change from baseline were summarized. Overall interpretations were listed.

Plasma CD24Fc Concentration

Figure 8:
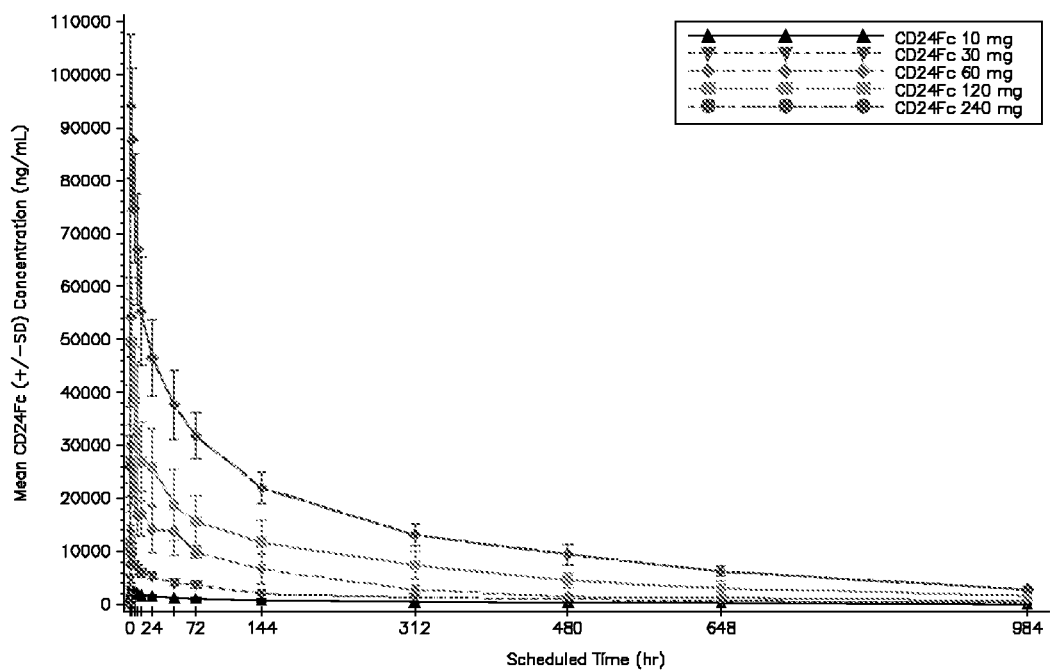
FIG. 8 shows a plot of mean plasma CD24Fc concentration (±SD) by treatment for a PK Evaluable Population in human subjects. PK=pharmacokinetic; SD=standard deviation.

As shown in FIG. 8, the mean plasma concentration of CD24Fc increased proportionally to the dose of CD24Fc administered. For all dose groups except 120 mg, the maximum mean plasma concentration of CD24Fc was reached at 1 hour post-dose. The maximum mean plasma concentration of CD24Fc for the 120 mg group was reached at 2 hours post-dose. By Day 42 (984 hours), the mean plasma concentration of CD24Fc for all groups had decreased to between 2% and 4% of the maximum mean plasma concentration.

Table 1 summarizes the plasma CD24Fc PK parameters by treatment for the PK Evaluable Population.

TABLE 1

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $C_{max}$ (ng/mL) | | | | | |
| n | 6 | 6 | 6 | 6 | 6 |
| Mean (SD) | 2495 (576) | 9735 (1715) | 30 083 (7179) | 52 435 (9910) | 95 865 (10 734) |
| CV % | 23.1 | 17.6 | 23.9 | 18.9 | 11.2 |
| Median | 2371 | 9218 | 29 026 | 50 401 | 93 206 |
| Min, Max | 1,967, 3,390 | 8,583, 13,086 | 22,557, 42,628 | 40,434, 65,704 | 81,296, 110,110 |
| Geometric mean | 2,442 | 9,625 | 29,424 | 51,666 | 95,365 |
| Geometric CV % | 22.8 | 16.1 | 23.0 | 19.0 | 11.2 |
| $AUC_{0-42d}$ (ng * hr/mL) | | | | | |
| n | 6 | 6 | 6 | 6 | 6 |
| Mean (SD) | 423,061 (99,615) | 1,282,430 (88,798) | 3,226,255 (702,862) | 6,541,501 (2,190,944) | 12,704,705 (1,918,596) |
| CV % | 23.5 | 6.9 | 21.8 | 33.5 | 15.1 |
| Median | 434,043 | 1,302,719 | 3,124,933 | 5,785,142 | 12,563,426 |
| Min, Max | 291,020, 528,079 | 1,175,733, 1,403,024 | 2,487,550, 4,139,748 | 4,485,193, 9,415,266 | 10,466,635, 15,693,606 |
| Geometric mean | 412,795 | 1,279,851 | 3,163,252 | 6,249,552 | 12,586,731 |
| Geometric CV % | 25.0 | 7.0 | 22.0 | 33.8 | 15.0 |
| $AUC_{0-inf}$ (ng * hr/mL) | | | | | |
| n | 6 | 6 | 6 | 6 | 6 |
| Mean (SD) | 462,260 (116,040) | 1,434,464 (131,316) | 3,497,196 (705,653) | 7,198,196 (2,458,320) | 13,861,796 (1,962,780) |
| CV % | 25.1 | 9.2 | 20.2 | 34.2 | 14.2 |
| Median | 470,426 | 1,422,205 | 3,519,732 | 6,463,665 | 13,713,034 |
| Min, Max | 310,956, 596,599 | 1,281,715, 1,650,503 | 2,703,655, 4,309,023 | 4,910,640, 10,479,940 | 11,822,988, 17,175,236 |
| Geometric mean | 449,583 | 1,429,578 | 3,437,036 | 6,862,129 | 13,750,972 |
| Geometric CV % | 26.7 | 9.0 | 20.7 | 34.6 | 13.8 |
| $T_{max}$ (hr) | | | | | |
| n | 6 | 6 | 6 | 6 | 6 |
| Mean (SD) | 1.15 (0.42) | 1.17 (0.41) | 1.01 (0.01) | 1.34 (0.51) | 1.33 (0.52) |
| CV % | 36.1 | 35.0 | 1.2 | 38.0 | 38.7 |
| Median | 1.00 | 1.00 | 1.00 | 1.03 | 1.00 |
| Min, Max | 0.92, 2.00 | 1.00, 2.00 | 1.00, 1.03 | 1.00, 2.00 | 1.00, 2.00 |
| $t_{1/2}$ (hr) | | | | | |
| n | 6 | 6 | 6 | 6 | 6 |
| Mean (SD) | 280.83 (22.37) | 327.10 (41.32) | 279.82 (65.59) | 286.45 (23.38) | 285.33 (24.33) |
| CV % | 8.0 | 12.6 | 23.4 | 8.2 | 8.5 |
| Median | 279.61 | 317.23 | 264.69 | 290.76 | 287.74 |
| Min, Max | 258.87, 321.26 | 289.82, 394.24 | 210.18, 362.46 | 243.89, 309.26 | 249.24, 322.26 |
| AUCextr (%) | | | | | |
| n | 6 | 6 | 6 | 6 | 6 |
| Mean (SD) | 7.61 (2.14) | 10.44 (2.94) | 7.88 (4.26) | 8.92 (1.94) | 8.46 (1.99) |
| CV % | 28.1 | 28.2 | 54.0 | 21.8 | 23.5 |
| Median | 7.16 | 10.01 | 6.35 | 9.27 | 8.45 |
| Min, Max | 5.46, 11.47 | 7.10, 15.05 | 3.92, 14.48 | 5.49, 10.99 | 5.56, 11.50 |
| CL (L/hr) | | | | | |
| n | 6 | 6 | 6 | 6 | 6 |
| Mean (SD) | 0.0229 (0.0061) | 0.0211 (0.0019) | 0.0178 (0.0036) | 0.0183 (0.0058) | 0.0176 (0.0023) |
| CV % | 26.7 | 8.8 | 20.5 | 31.7 | 13.3 |
| Median | 0.0216 | 0.0211 | 0.0173 | 0.0191 | 0.0175 |
| Min, Max | 0.0168, 0.0322 | 0.0182, 0.0234 | 0.0139, 0.0222 | 0.0115, 0.0244 | 0.0140, 0.0203 |
| Vd (L) | | | | | |
| n | 6 | 6 | 6 | 6 | 6 |
| Mean (SD) | 9.153 (1.943) | 9.867 (0.804) | 7.289 (2.592) | 7.491 (2.202) | 7.276 (1.426) |
| CV % | 21.2 | 8.1 | 35.6 | 29.4 | 19.6 |

TABLE 1-continued

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| Median | 8.507 | 10.007 | 7.486 | 7.691 | 7.151 |
| Min, Max | 7.326, 12.010 | 8.771, 10.958 | 4.222, 11.139 | 4.933, 9.974 | 5.814, 9.438 |

$AUC_{0-42d}$ = area under the concentration-time curve from time 0 to 42 days;
$AUC_{0-inf}$ = area under the concentration-time curve extrapolated from time 0 to infinity;
$AUC_{extr}$ = percentage of AUCo-inf that was due to extrapolation from the time of the last measurable concentration, per subject, to infinity;
CL = total body clearance;
$C_{max}$ = maximum observed plasma drug concentration;
CV % = coefficient of variation;
Min = minimum;
Max = maximum;
SD = standard deviation;
$t_{1/2}$ = terminal elimination half-life;
$T_{max}$ = time of maximum observed plasma drug concentration;
$V_d$ = volume of distribution.

Plasma CD24Fc Dose Proportionality Analysis

Figure 9:
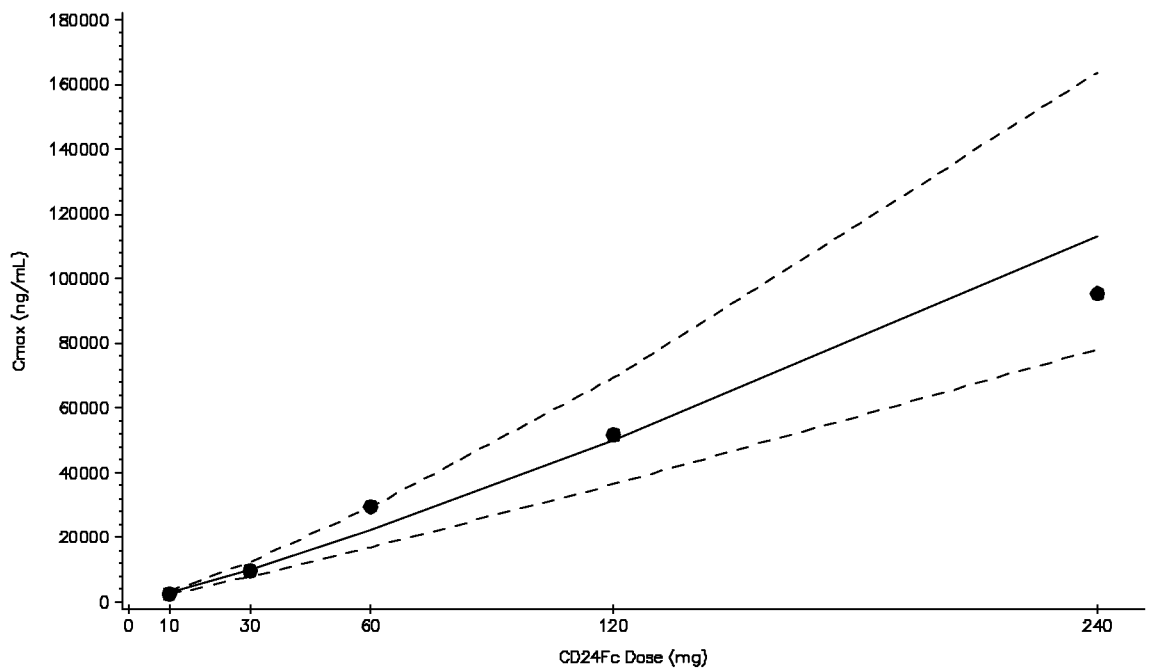
FIG. 9 shows a dose proportionality plot of CD24Fc $C_{max}$ versus dose for a PK Evaluable Population.
Figure 10:
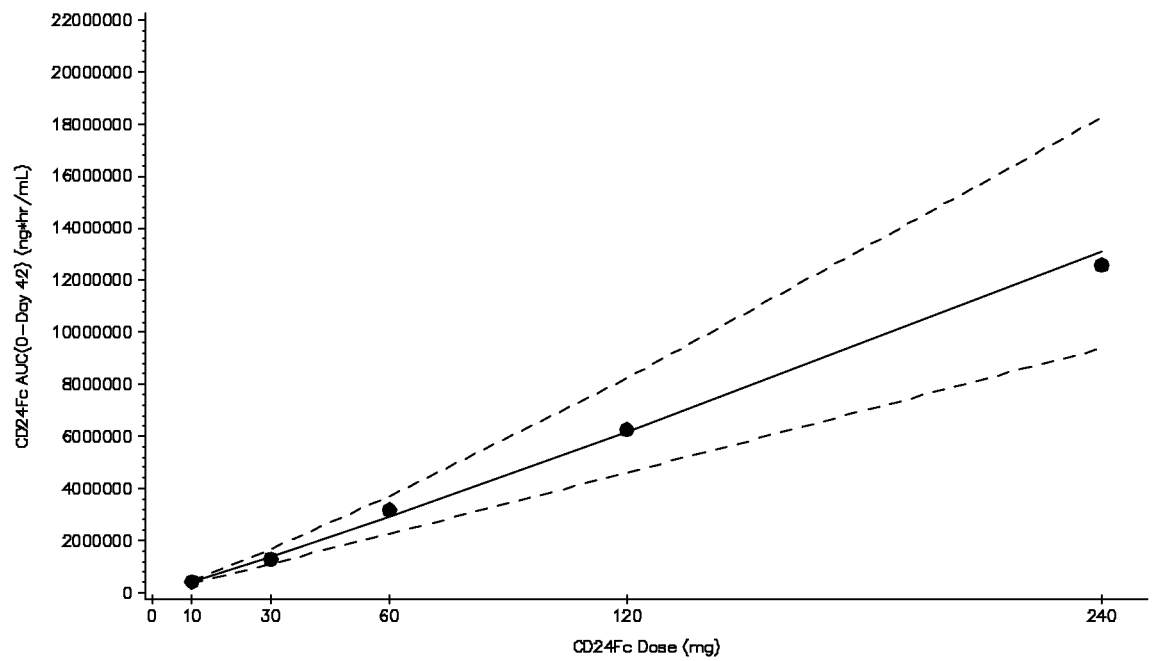
FIG. 10 shows a dose proportionality plot of CD24Fc $AUC_{0-42d}$ versus dose for a PK Evaluable Population.
Figure 11:
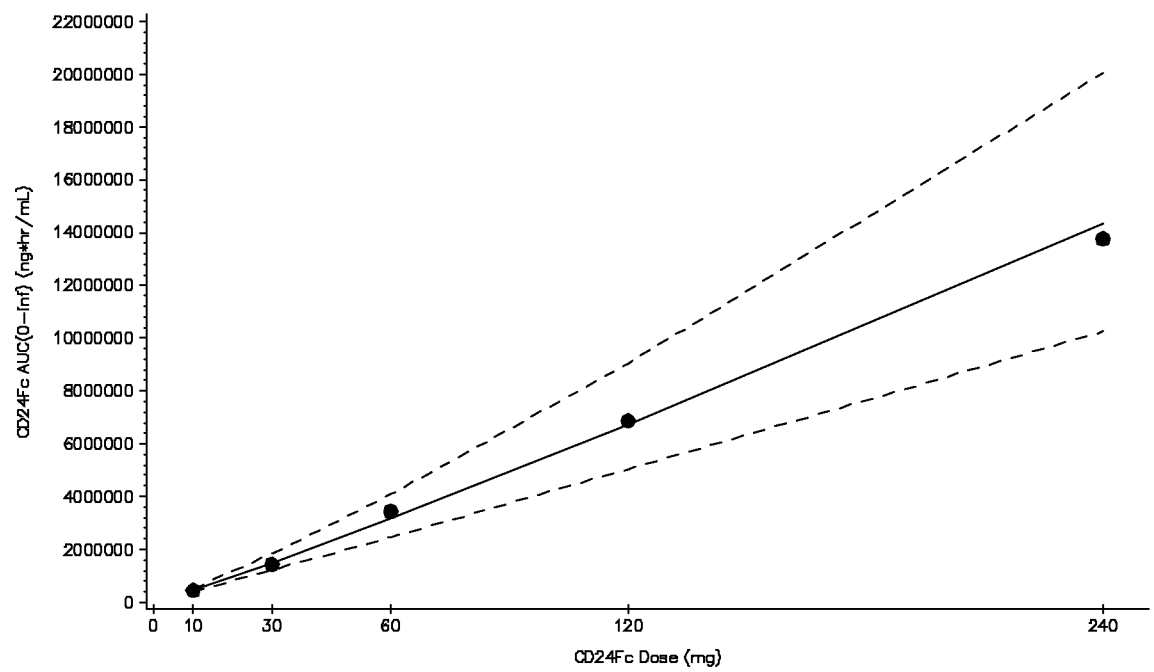
FIG. 11 shows a dose proportionality plot of CD24Fc $AUC_{0-inf}$ versus dose for a PK Evaluable Population.

FIG. 9 shows a dose proportionality plot of CD24Fc $C_{max}$ versus dose for the PK Evaluable Population. FIG. 10 shows a dose proportionality plot of CD24Fc $AUC_{0-42d}$ versus dose for the PK Evaluable Population. FIG. 11 shows a dose proportionality plot of CD24Fc $AUC_{0-inf}$ versus dose for the PK Evaluable Population. Table 2 shows a power analysis of dose proportionality.

TABLE 2

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality | | |
|---|---|---|---|---|---|---|---|---|
| | | | | | | Slope Estimate | Standard Error | 90% CI |
| $C_{max}$ (ng/mL) | | | | | | 1.172 | 0.040 | (1.105, 1.240) |
| Geometric mean | 2,441.8 | 9,624.9 | 29,424.4 | 51,666.4 | 95,364.9 | | | |
| Geometric CV % | 22.8 | 16.1 | 23.0 | 19.0 | 11.2 | | | |
| $AUC_{0-42d}$ (ng*hr/mL) | | | | | | 1.088 | 0.036 | (1.027, 1.148) |
| Geometric mean | 412,794.8 | 1,279,850.8 | 3,163,251.7 | 6,249,551.9 | 12,586,731.3 | | | |
| Geometric CV % | 25.0 | 7.0 | 22.0 | 33.8 | 15.0 | | | |
| $AUC_{0-inf}$ (ng*hr/mL) | | | | | | 1.087 | 0.036 | (1.026, 1.148) |
| Geometric mean | 449,583.5 | 1,429,577.5 | 3,437,035.6 | 6,862,128.7 | 13,750,972.4 | | | |
| Geometric CV % | 26.7 | 9.0 | 20.7 | 34.6 | 13.8 | | | |

Geometric CV % = 100*sqrt(exp($SD^2$) − 1), where SD was the standard deviation of the log-transformed data. The power model was fitted by restricted maximum likelihood, regressing the log-transformed PK parameter on log transformed dose. Both the intercept and slope were fitted as fixed effects. Dose proportionality was not rejected if the 90% CI lies within (0.8, 1.25).
$AUC_{0-42d}$ = area under the concentration-time curve from time 0 to 42 days; $AUC_{0-inf}$ = area under the concentration-time curve extrapolated from time 0 to infinity; CI = confidence interval; $C_{max}$ = maximum observed plasma drug concentration; CV % = coefficient of variation; PK = pharmacokinetic; SD = standard deviation.

The $C_{max}$ slope estimate was 1.172 with a 90% CI of 1.105 to 1.240. The $AUC_{0-42d}$ slope estimate was 1.088 with a 90% CI of 1.027 to 1.148. The $AUC_{0-inf}$ slope estimate was 1.087 with a 90% CI of 1.026 to 1.1.

Pharmacokinetic Conclusions

The $C_{max}$ and AUCs of plasma CD24Fc increased proportionally to the doses administered in mouse, monkey and human. The plasma CD24Fc reached $T_{max}$ between 1.01 and 1.34 hours. The $t_{1/2}$ of plasma CD24Fc ranged between 280.83 and 327.10 hours.

Example 5

CD24 can be Used to Treat Graft Versus Host Disease in Human Subjects

Figure 12:
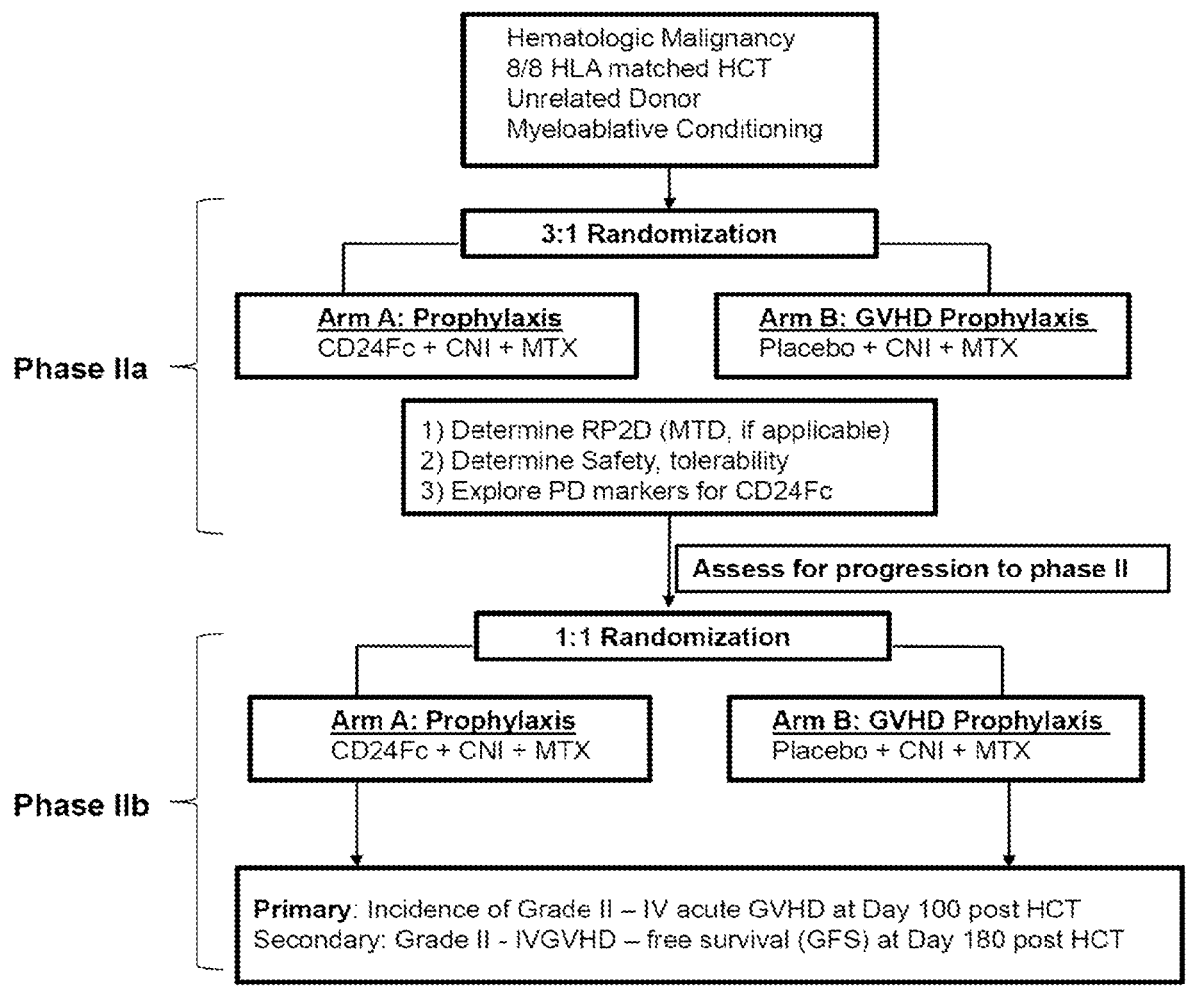
FIG. 12 shows the trial design for the randomized, placebo-controlled Phase IIa dose escalation trial was performed to evaluate the addition of CD24Fc to standard of care acute GVHD prophylaxis in cancer patients undergoing allogeneic myeloablative hematopoietic stem cell transplantation (HCT).

A multicenter, prospective, double-blind, randomized, placebo-controlled Phase IIa dose escalation trial was performed to evaluate the addition of a CD24 protein, CD24Fc, to standard of care acute GVHD prophylaxis in cancer patients undergoing allogeneic myeloablative hematopoietic stem cell transplantation (HCT). The trial design is shown in FIG. 12.

The primary objectives of the phase IIa study include assessing the safety and tolerability of CD24Fc in combination with methotrexate and tacrolimus prophylaxis in patients undergoing matched unrelated donor HCT following myeloablative conditioning, and to define the recommended phase 2 dose (RP2D) or maximum tolerated dose (MTD). In addition, secondary efficacy objectives in the phase IIa study include:
    determining if the addition of CD24Fc to standard GVHD
        prophylaxis methotrexate and tacrolimus reduces the
        cumulative incidence of grade II-IV aGVHD at day 100
        after HCT estimating grade II-IV aGVHD free survival (GFS) at day 180 after HCT, describing the incidence of cGVHD (cGVHD) at 1 year describing the incidence of relapse one year following HCT describing the incidence of transplant-related mortality (TRM) one year following HCT describing infection rates at day 100 following HCT evaluating overall survival (OS), absence of grade III-IV GVHD, and relapse-free survival one year following HCT evaluating conditioning toxicity including oral mucositis and organ failure Other objectives include assessing the pharmacokinetic (PK) profile of CD24Fc, examining the immune cell profile and functional responses of APCs and T cells after HCT in the CD24Fc and placebo groups, and assessing pharmacodynamics (PD) biomarkers such as the plasma concentrations of pro-inflammatory cytokines, DAMPs, lipids, and GVHD biomarkers in the CD24Fc and placebo groups.

The trial enrolled patients receiving transplants from matched unrelated donors undergoing allogeneic HCT according to institutional practice. Patients between the ages of 18-70 years old undergoing matched unrelated donor allogeneic HCT for a malignant hematologic condition with a Karnofsky performance score ≥70% were eligible for the study. An 8/8 HLA allelic match between the unrelated donor and the recipient at HLA-A, HLA-B, HLA-C, and HLA-DRB1 was required. Restricting the study to patients receiving HCT from unrelated donors is expected to limit heterogeneity and facilitate statistical estimates of aGVHD incidence for subsequent efficacy assessments, given the greater incidence of grade II-IV aGVHD (60-80%) and grade III-IV aGVHD (20-35%) in this population.

This trial exclusively utilized myeloablative conditioning regimens and standard of care (SOC) prophylaxis comprising tacrolimus and methotrexate since these patients experience the most severe tissue injury and drug will likely have the strongest biological effect in this setting. All patients received myeloablative conditioning and standard of care GVHD prophylaxis with methotrexate and tacrolimus per the phase IIa protocol. Patients received a myeloablative conditioning regimen consisting of either fludarabine and busulfan (Flu/Bu 4) or cyclophosphamide and total body irradiation (Cy/TBI), as decided by the treating physician, followed by an infusion of stem cells on day 0. GVHD prophylaxis was administered to all patients and consisted of tacrolimus (initiated Day −3 before transplant) and methotrexate (initiated Day +1 after transplant) in combination with CD24Fc in the treatment arm or saline in the placebo arm. In the absence of GVHD, tacrolimus tapering started on day +100. The source of donor stem cells was either peripheral blood stem cells (PBSC) or bone marrow (BM).

Figure 13:
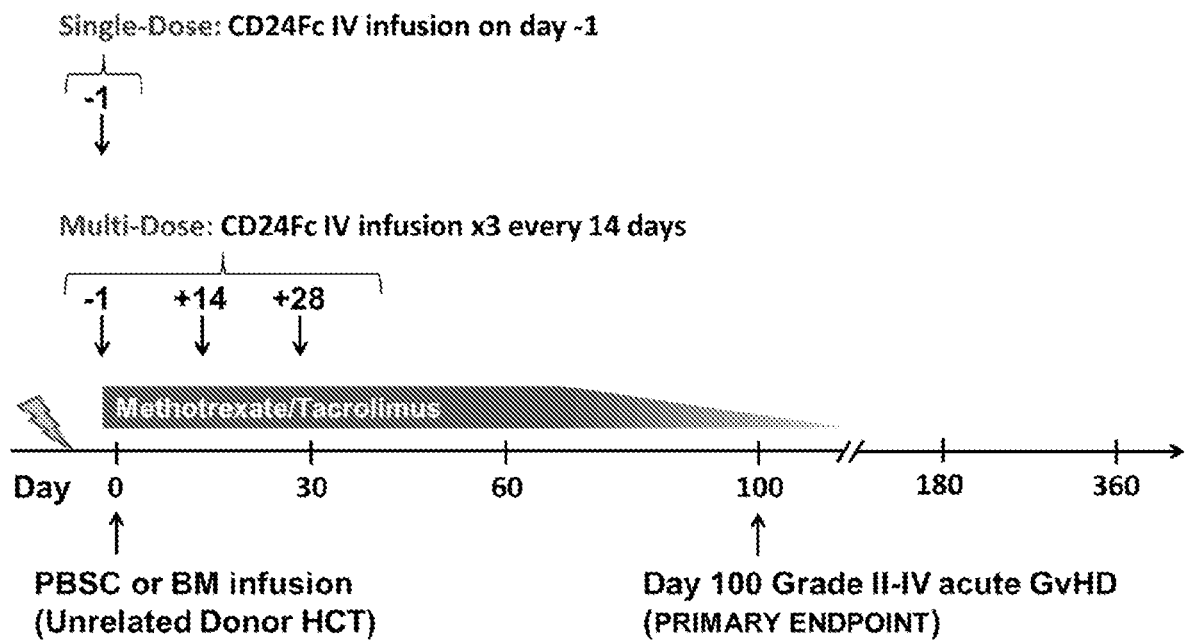
FIG. 13 shows the dosing scheme for the single dose and multi-dose cohorts in the Phase IIa trial.

The Phase IIa trial comprised two single ascending dose cohorts (240 mg and 480 mg) and a single multi-dose cohort of CD24Fc in addition to SOC GVHD prophylaxis as outlined in Table 3 below. As shown in FIG. 13, in the single dose cohort, the study agent, CD24Fc, was administered intravenously on day −1 relative to the day of stem cell transplant. In the multi-dosing cohort, patients received 3 biweekly administrations of CD24Fc at 480 mg (day −1), 240 mg (day +14) and 240 mg (day +28). Based upon PK data for CD24Fc this biweekly dosing period will allow for passage of greater than two half-lives. Dosing is based on a fixed amount and not based on weight or BSA. Each dosing cohort enrolled 8 subjects using a randomized 3:1 ratio (6 CD24Fc subjects and 2 placebo) design for a total enrollment of 24 patients.

TABLE 3

Phase 2a Dose Escalation Plan

| Level | Dose | Schedule | CD24Fc (No.) | Placebo (No.) |
|---|---|---|---|---|
| −1 | 120 mg | day −1 | 6 | 2 |
| 0 | 240 mg | day −1 | 6 | 2 |
| 1 | 480 mg | day −1 | 6 | 2 |
| 2 | 960 mg (multi-dose) | 480 mg (day −1)* 240 mg (day 14) 240 mg (day 28) | 6 | 2 |

Table 4 lists demography information and clinical characteristics for patients in the CD24Fc and placebo cohorts, which were relatively balanced across risk factors such as age, malignancy, and comorbidity. The most common malignancy in both the CD24Fc and placebo cohorts was AML/MDS (66.7% and 83.3%). 72% of the patients in the CD24Fc cohort and 50% in the placebo group had a comorbidity index of intermediate or high. PBSCs were more frequently used as the graft source as compared to bone marrow in both cohorts, and Flu/Bu 4 was the most common conditioning regimen across both cohorts. Four patients, all in the CD24Fc cohorts, underwent Cy/TBI conditioning.

TABLE 4

Phase 2a Patient Characteristics

| | | CD24Fc + TAC/MTX (N = 18) | Placebo + TAC/MTX (N = 6) |
|---|---|---|---|
| Age (years) | Median (range) | 62 (23-68) | 57 (36-66) |
| Gender (N, %) | Female | 7 (38.8) | 2 (33.3) |
| | Male | 11 (61.1) | 4 (66.7) |
| Graft Source (N, %) | PBSC | 15 (83.3) | 4 (66.7) |
| | BM | 3 (16.7) | 2 (33.3) |
| Malignancy (N, %) | AML/MDS | 12 (66.7) | 5 (83.3) |
| | CML | 2 (11.1) | 0 (0) |
| | CMML | 1 (5.6) | 1 (16.7) |
| | ALL | 3 (16.7) | 0 (0) |
| Comorbidity index (score) | Low (0) | 5 | 3 |
| | Intermediate (1-2) | 9 | 2 |
| | High (3-4) | 4 | 1 |
| Cytomegalovirus status | D+, R+ | 5 | 1 |
| | D+, R− | 1 | 0 |
| | D−, R+ | 3 | 1 |
| | D−, R− | 8 | 4 |

TABLE 4-continued

Phase 2a Patient Characteristics

|  |  | CD24Fc + TAC/MTX (N = 18) | Placebo + TAC/MTX (N = 6) |
|---|---|---|---|
| Conditioning regimen (N) | Flu/Bu 4 | 14 (77.8) | 6 (100) |
|  | Cy/TBI | 4 (22.2) | 0 (0) |
| Engraftment Day (Day) | Neutrophil | 13.0 | 15.5 |
|  | (min, max) | (12, 23) | (12, 18) |
|  | Platelets | 13.0 | 15.0 |
|  | (min, max) | (9, 23) | (11, >48) |

BM = Bone marrow;
Cy/TBI = cyclophosphamide/total body irradiation;
D = donor;
Flu/Bu 4 = fludarabine/busulfan;
R = recipient The primary objectives of the study are: to evaluate the safety and tolerability of CD24Fc in subjects undergoing myeloablative allogeneic hematopoietic cell transplantation (HCT); and to determine the recommended Phase II dose (RP2D) or maximum tolerable dose (MTD) of CD24Fc in patients undergoing HCT.

All patients enrolled in the study have completed the Treatment period, which is the first day of treatment with CD24Fc until 30 days after HCT for the single-dosing cohorts or 60 days after HCT for the multi-dosing cohort (the exact days may vary depending on the last day of administration of study drug without constituting a deviation) and is the assessment and reporting period for adverse events (AE) including dose limiting toxicities potentially related to the study drug. Table 5 provides a summary of toxicities observed in the Phase 2a trial. Overall this study demonstrated that IV administration of CD24Fc up to 480 mg is generally well tolerated in the intent-to-treat (ITT) population. No infusion toxicities, dose-limiting toxicities (DLTs) or SAEs attributable or likely attributable to the study drug have been observed and no patients have been removed from the study.

Figure 14:
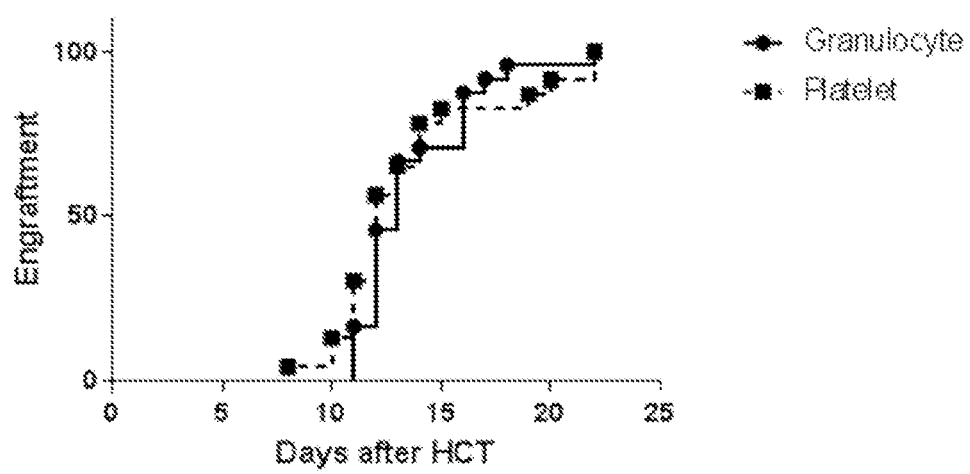
FIG. 14 shows the median time to engraftment for patients enrolled in the trial.
Figure 15:
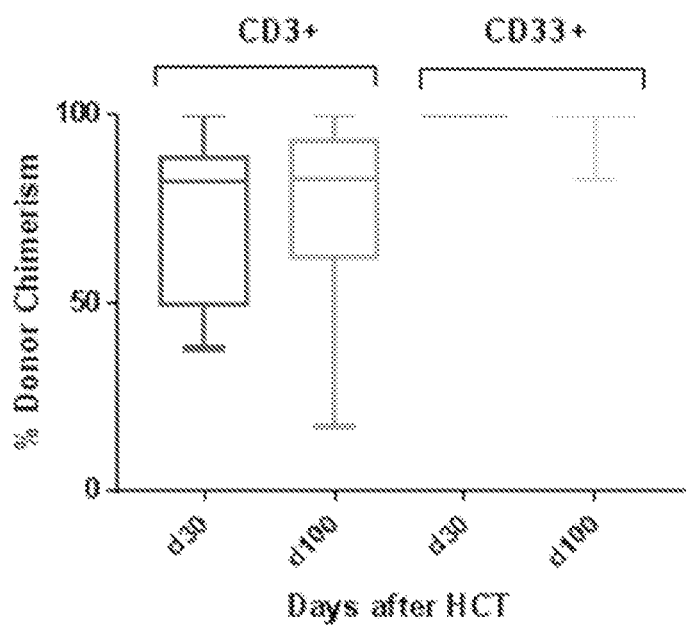
FIG. 15 shows the myeloid donor chimerism for patients enrolled in the trial.

All 24 subjects enrolled engrafted following transplant as shown in FIG. 14. Neutrophils engrafted a median of 13.0 and 15.5 days after HCT in CD24Fc exposed and placebo patients, respectively. Platelets engrafted a median of 13.0 and 15.0 days after HCT in CD24Fc exposed and placebo patients, respectively, with the exception of one patient in the placebo group in whom platelets did not engraft and who died on Day 49. There were no cases of graft failure. The median CD3 chimerism at day +30 was 82.5% (range 38-100%) in the CD24Fc exposed patients and 82.0% (range, 62%-91%) in the placebo group (FIG. 15). The median donor CD3 chimerism increased to 86% (range, 42%-100%) at day 100 in the CD24Fc exposed patients and 84% (range, 17%-100%) in the placebo group. Donor CD33 chimerism at day 30 and 100 was 100% in both the CD24Fc and placebo groups.

TABLE 5

Summary of Toxicities

| Cohort | Treatment | # of Pts | Infusion Rxn | SAE | DLT |
|---|---|---|---|---|---|
| Single 240 mg | CD24Fc | 6 | 0 | 1 | 0 |
|  | Placebo | 2 | 0 | 2 | 0 |
| Single 480 mg | CD24Fc | 6 | 0 | 0 | 0 |
|  | Placebo | 2 | 0 | 1 | 0 |
| Multidose | CD24Fc | 6 | 0 | 4 | 0 |
|  | Placebo | 2 | 0 | 2 | 1 |

Efficacy analyses for the Phase 2a study are considered secondary and include the following: to describe grade III-IV acute GVHD free survival (GFS) at day 180 following HCT; to describe the cumulative incidence of grade II-IV acute GVHD at day 100 after HCT; to describe grade III-IV GVHD, Relapse Free Survival at day 180 after HCT; to describe grade II-IV acute GFS at day 180 following HCT; to describe incidence of chronic GVHD at one year following HCT; to describe incidence of relapse at one year following HCT; to describe incidence of transplant-related mortality (TRM) at one year following HCT; to describe rates of infection at day 100 following HCT; to evaluate overall survival (OS) and disease free survival (DFS) at one year following HCT.

In addition to inclusion of the placebo arm in the phase IIa study, data on contemporary controls (N=92) were collected from the same institutions undergoing matched unrelated donor HCT following the same myeloablative conditioning and GVHD prophylaxis regimens (minus the experimental therapy CD24Fc) from the period of January 2012 to November 2017. A contemporary control cohort was included given the small number of patients in the placebo control arm. The demography data of the 92 adult patients in the contemporary control cohort is summarized in Table 6.

TABLE 6

Characteristics of Patients Enrolled in the Contemporary Control Cohort

|  |  | TAC/MTX (N = 92) |
|---|---|---|
| Age (years) | Median (range) | 49 (21-69) |
| Gender (N, %) | Female | 41 (44.5) |
|  | Male | 51 (55.5) |
| Malignancy (N, %) | AML/MDS | 63 (68.5) |
|  | CML | 3 (3) |
|  | CMML | 2 (2) |
|  | ALL | 24 (26.5) |

Tables 7 and 8 provide an overview of the clinical outcomes of the Ph 2a study. Acute GVHD was graded according to consensus guidelines utilized by the international CIBMTR registry and Blood and Marrow Transplant Clinical Trials Network and recorded weekly. Patients were evaluated for aGVHD following receipt of HCT on day 0 until day 100 after HCT.

TABLE 7

Overview of Clinical Outcomes, including the cumulative incidence of grade II-IV and grade III-IV aGVHD.

| Cohort | aGVHD (Day 180) | Relapse (Day 180) | Death (Day 180) |
|---|---|---|---|
| 1) Single Dose: 240 mg (N = 6) | Gr II: 2 (skin)<br>Gr III: 0<br>Gr IV: 0<br>Gr II-IV: 33.3%<br>(95% CI, 3.2, 70.4)<br>Gr III-IV: 0% | 0 | 0 |
| 2) Single Dose: 480 mg (N = 6) | Gr II: 2 (Skin and Upper GI)<br>Gr III: 1 (Lower GI)<br>Gr IV: 0<br>Gr II-IV: 50.0%<br>(95% CI, 7.7, 82.9)<br>Gr III-IV: 16.7% | 1<br>CMML<br>(d161) | 0 |
| 3) Multi-Dose: (N = 6) | Gr II: 2 (Skin and Upper GI)<br>Gr III: 0<br>Gr IV: 0<br>Gr II-IV: 33.3%<br>(95% CI, 3.2, 70.4)<br>Gr III-IV: 0% | 1<br>ALL<br>(d103) | 0 |
| CD24Fc Total: | Gr II: 6<br>Gr III: 1<br>Gr IV: 0<br>Gr II-IV: 38.9%<br>(95% CI, 16.8, 60.7)<br>Gr III-IV: 5.6% | 2/18<br>(11.1%) | 0/18* |
| Placebo (N = 6) | Gr II: 0<br>Gr III: 1 (Lower GI)<br>Gr IV: 0<br>Gr II - IV: 16.7%<br>(95% CI, 0.5, 54.9)<br>Gr III-IV: 16.7% | 2/6<br>(33.3%) | 1/6<br>(16.7%) |
| Contemporary Control (N = 92) | Gr II: 22<br>Gr III: 16<br>Gr IV: 3<br>Gr II-IV: 50% (death as competing factor) (95% CI, 39.8, 60.2)<br>Gr III-IV: 24% (death as competing factor) (95% CI, 17, 31) | 19/92<br>(23.1%)<br>(Death as competing factor) | 22/92<br>(23.9%) |

*Deaths (n = 2) after day 180: Cohort 1 Pneumonitis 2/2 infections (d 210) and Cohort 2 relapse of CMML (d 196)

TABLE 8

Summary of Clinical Outcomes

| | CD24Fc | Placebo | Statistical Significance |
|---|---|---|---|
| Number | 18 | 6 | |
| aGVHD III-IV | | | |
| D100 | 6% | 17% | |
| D180 | 6% | 17% | |
| 1 yr Relapse | 11% | 33% | |
| 1 yr NRM | 6% | 17% | |
| 1.5 yr RFS | 83% | 50% | |
| 1.5 yr OS | 89% | 50% | P = 0.046 |
| D180 Gr III-IV, Relapse Free Survival | 83% | 33% | P = 0.01 |

Incidence of Grade II to IV Acute Graft-Versus-Host Disease by Day 100

Table 9 summarizes the cumulative incidence of Grade II to IV acute GVHD by Day 100 for the mITT Population. In total, 7 (38.9%) patients who received CD24Fc (2 [33.3%] patients in the 240 mg CD24Fc single dose cohort, 3 [50.0%] patients in the 480 mg CD24Fc single dose cohort, and 2 [33.3%] patients in the 960 mg CD24Fc multiple dose cohort) and 1 (16.7%) patient who received placebo had Grade II to IV acute GVHD by Day 100. Additionally, 1 (16.7%) patient who received placebo died without Grade II to IV acute GVHD by Day 100. Patients who were alive with no occurrence of Grade II to IV acute GVHD through Day 100 were censored at their last assessment for acute GVHD on or prior to Day 100. At least 50.0% of patients in each treatment group were censored.

TABLE 9

Cumulative Incidence of Grade II to IV Acute Graft-Versus-Host Disease by Day 100 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with Grade II-IV acute GVHD by Day 100 (n, %) | 1 (16.7) | 2 (33.3) | 3 (50.0) | 2 (33.3) | 7 (38.9) |
| No. of patients who died without Grade II-IV acute GVHD by Day 100 (n, %) | 1 (16.7) | 0 (0.0) | 0 (0.0) | 0 (0.0) | 0 (0.0) |

TABLE 9-continued

Cumulative Incidence of Grade II to IV Acute Graft-Versus-Host Disease by
Day 100 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients censored (n, %) | 4 (66.7) | 4 (66.7) | 3 (50.0) | 4 (66.7) | 11 (61.1) |
| Cumulative incidence (%) of Grade II-IV acute GVHD by Day 100 [1] | 16.7 | 33.3 | 50.0 | 33.3 | 38.9 |
| 95% CI | | (0.5, 54.9) | (3.2, 70.4) | (7.7, 82.9) | (3.2, 70.4) | (16.8, 60.7) |
| Treatment comparison: CD24Fc versus placebo [2] | | | | | |
| Hazard ratio (90% CI) | | | | | 2.6 (0.5, 14.7) |

Note:
Day 100 = Day 100 (+7 days) post-transplant (ie, Study Day 108).
Percentage was calculated using the number of patients in the column heading as the denominator.
1. Grades were based on the CIBMTR grading scale. The cumulative incidence (%) of acute GVHD by Day 100 and the 95% CI were estimated using the cumulative incidence function with death without Grade II to IV acute GVHD as a competing risk.
2. Hazard ratio and 90% CI were based on a Fine and Gray model with treatment as a covariate and death without Grade II to IV acute GVHD as a competing risk.
CI = confidence interval;
CIBMTR = Center for International Blood and Marrow Transplant Research;
GVHD = graft-versus-host disease;
No. = number.

Overall, the cumulative incidence of Grade II to IV acute GVHD by Day 100 (with 95% CI) was 38.9% (16.8%, 60.7%) for the CD24Fc treatment group and 16.7% (0.5%, 54.9%) for the placebo group. The hazard ratio (with 90% CI) for CD24Fc versus placebo was 2.6 (0.5, 14.7). The cumulative incidence of grade II-IV aGVHD was 50% in the contemporary control. In the CD24Fc treated group, four cases of grade II aGVHD involved skin only and two cases involved skin and the upper gastrointestinal (GI) tract. There were no cases grade II aGVHD in the placebo group.

Grade II-IV Acute Graft-Versus-Host Disease-Free Survival Through Day 180

Table 10 summarizes Grade II to IV acute GFS through Day 180 for the mITT Population. The median Grade II to IV acute GFS Kaplan-Meier estimate was not reached in any treatment group. Overall, the Grade II to IV acute GFS rate at Day 180 (with 95% CI) was 61.1% (35.3%, 79.2%) for the CD24Fc treatment group and 50.0% (11.1%, 80.4%) for the placebo group. The hazard ratio (with 90% CI) for CD24Fc versus placebo was 0.8 (0.3, 2.5). Patients who were alive and had no documented occurrence of Grade II to IV acute GVHD at the data cutoff date were censored at the last date of acute GVHD assessment on or prior to Day 180. In addition to the small sample size, at least 50.0% of patients in each treatment group were censored.

TABLE 10

Grade II to IV Acute Graft-Versus-Host Disease-Free Survival Through Day 180 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with events (n, %) | 3 (50.0) | 2 (33.3) | 3 (50.0) | 2 (33.3) | 7 (38.9) |
| Earliest contributing event | | | | | |
| Acute GVHD (Grade II-IV) | 2 (33.3) | 2 (33.3) | 3 (50.0) | 2 (33.3) | 7 (38.9) |
| Death | 1 (16.7) | 0 (0.0) | 0 (0.0) | 0 (0.0) | 0 (0.0) |
| No. of patients censored (n, %) | 3 (50.0) | 4 (66.7) | 3 (50.0) | 4 (66.7) | 11 (61.1) |
| Acute GVHD (Grade (II-IV)-free survival (days) | | | | | |
| Kaplan-Meier estimate [1] | | | | | |
| Median (95% CI) | NE | NE | NE | NE | NE |
| Mean (SD) [2] | 144.2 (74.98) | 145.7 (77.01) | 116.2 (86.69) | 150.5 (68.96) | 137.4 (74.81) |

TABLE 10-continued

Grade II to IV Acute Graft-Versus-Host Disease-Free Survival Through Day 180 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Median [2] | 190.0 | 195.0 | 121.0 | 195.0 | 195.0 |
| Min, max [2] | 46, 195+ | 32, 195+ | 24, 195+ | 59, 195+ | 24, 195+ |
| Treatment comparison: CD24Fc versus placebo [3] | | | | | |
| Hazard ratio (90% CI) | | | | | 0.8 (0.3, 2.5) |
| Rate (%) of being alive without acute GVHD (Grade II-IV) at Day 180 (95% CI) [4] | 50.0 (11.1, 80.4) | 66.7 (19.5, 90.4) | 50.0 (11.1, 80.4) | 66.7 (19.5, 90.4) | 61.1 (35.3, 79.2) |

Note:
Day 180 = Day 180 (+14 days) post-transplant (ie, Study Day 195).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate.
CI = confidence interval;
GVHD = graft-versus-host disease;
log = logarithm;
max = maximum;
min = minimum;
NE = not estimable;
No. = number;
SD = standard deviation.

Grade III to IV Acute GFS Through Day 180 for the mITT Population

Figure 30B:
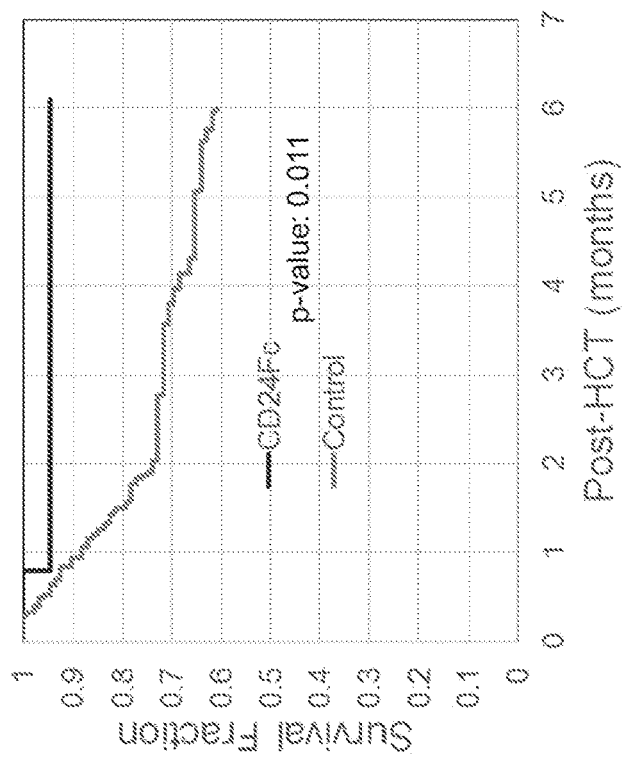
FIGS. 30A-B show the 180 Day Grade III-IV GVHD Free Survival in the CD24Fc group compared to the placebo control group (FIG. 30A) and the contemporary control group (FIG. 30B).
Figure 30A:
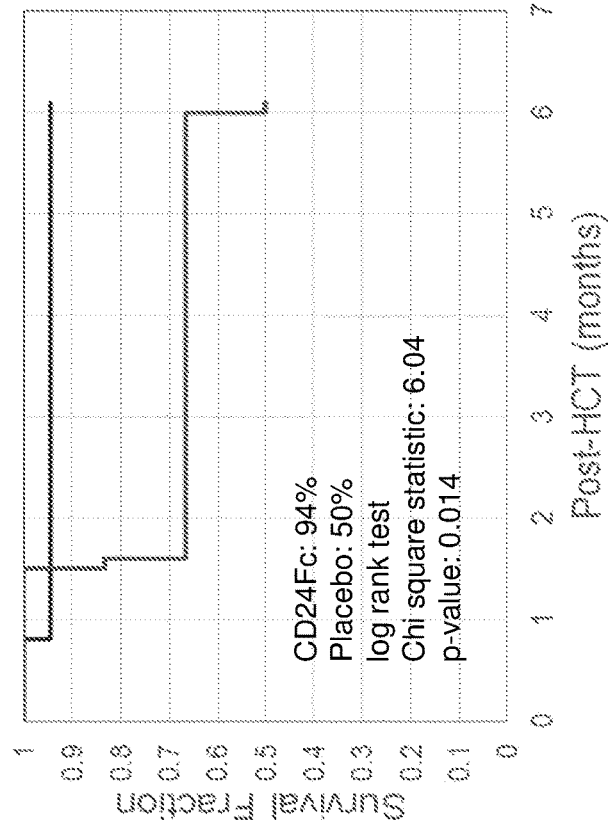
Figure 31A:
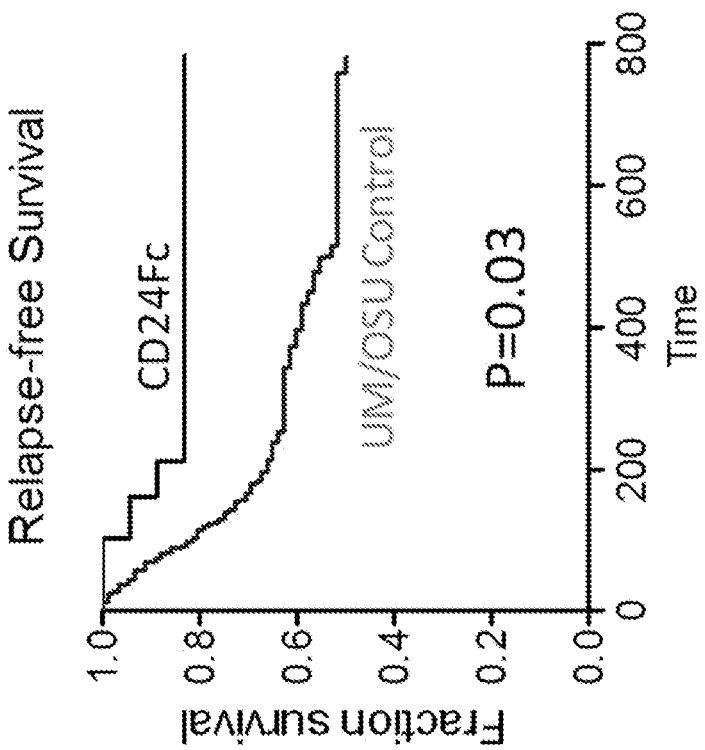
FIGS. 31A-B show the Relapse Free Survival in the CD24Fc group compared to the placebo control group (FIG. 31A) and the contemporary control group (FIG. 31B).
Figure 31B:
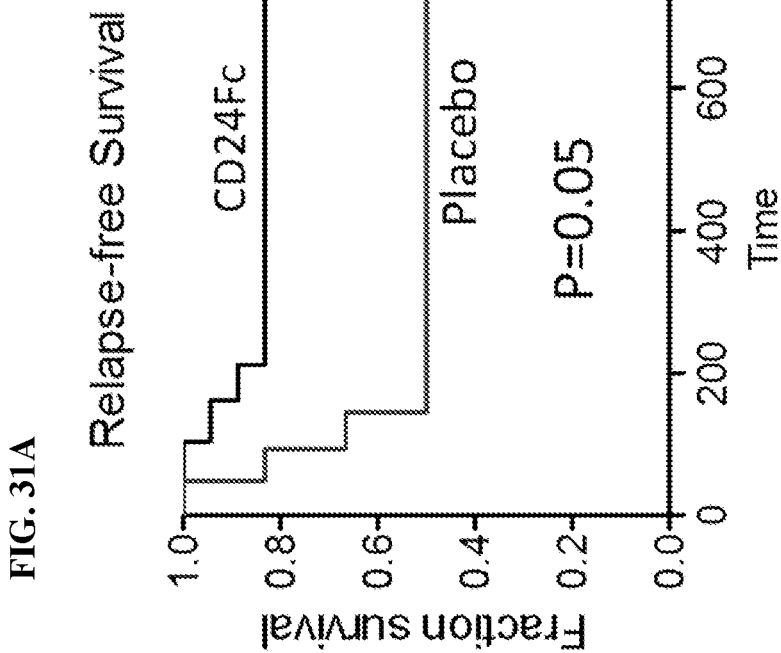

As shown in Table 11, in total, 1 (5.6%) patient who received CD24Fc (1 [16.7%] patient in the 480 mg CD24Fc single dose cohort) and 2 (33.3%) patients who received placebo had Grade III to IV acute GVHD by Day 180. Overall, the Grade III to IV acute GFS rate at Day 180 (with 95% CI) was 94.4% (66.6%, 99.2%) for the CD24Fc treatment group and 50.0% (11.1%, 80.4%) for the placebo group. The hazard ratio (with 90% CI) for CD24Fc versus placebo was 0.1 (0.0, 0.7). Patients who were alive and had no documented occurrence of Grade III to IV acute GVHD at the data cutoff date were censored at the last date of acute GVHD assessment on or prior to Day 180. At least 50.0% of patients in each treatment group were censored. Grade III to IV acute GFS rate at Day 180 was 24% in the contemporary control cohort. FIG. 30 shows the 180 Day Grade III-IV GVHD Free Survival in the CD24Fc group compared to the placebo control group (FIG. 31A) and the contemporary control group (FIG. 31B).

TABLE 11

Grade III to IV Acute Graft-Versus-Host Disease-Free Survival Through Day 180 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with events (n, %) | 3 (50.0) | 0 (0.0) | 1 (16.7) | 0 (0.0) | 1 (5.6) |
| Earliest contributing event | | | | | |
| Acute GVHD (Grade III-IV) | 2 (33.3) | 0 (0.0) | 1 (16.7) | 0 (0.0) | 1 (5.6) |
| Death | 1 (16.7) | 0 (0.0) | 0 (0.0) | 0 (0.0) | 0 (0.0) |
| No. of patients censored (n, %) | 3 (50.0) | 6 (100.0) | 5 (83.3) | 6 (100.0) | 17 (94.4) |
| Acute GVHD (Grade (III-IV)-free survival (days) | | | | | |
| Kaplan-Meier estimate [1] | | | | | |
| Median (95% CI) | NE | NE | NE | NE | NE |
| Mean (SD) [2] | 144.2 (74.98) | 195.0 (0.00) | 166.5 (69.81) | 195.0 (0.00) | 185.5 (40.31) |

TABLE 11-continued

Grade III to IV Acute Graft-Versus-Host Disease-Free Survival Through Day 180 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Median [2] | 190.0 | 195.0 | 195.0 | 195.0 | 195.0 |
| Min, max [2] | 46,195+ | 195+, 195+ | 24, 195+ | 195+, 195+ | 24, 195+ |
| Treatment comparison: CD24Fc versus placebo [3] | | | | | |
| Hazard ratio (90% CI) | | | | | 0.1 (0.0, 0.7) |
| Rate (%) of being alive without acute GVHD (Grade III-IV) at Day 180 (95% CI) [4] | 50.0 (11.1, 80.4) | 100.0 (NE) | 83.3 (27.3, 97.5) | 100.0 (NE) | 94.4 (66.6, 99.2) |

Note:
Day 180 = Day 180 (+14 days) post-transplant (ie, Study Day 195).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate.
CI = confidence interval;
GVHD = graft-versus-host disease;
log = logarithm;
max = maximum;
min = minimum;
NE = not estimable;
No. = number;
SD = standard deviation.

All patients who developed aGVHD in the study at the time of the data cutoff have responded to steroid treatment, as compared to the 50% response rate observed in the contemporary cohort control. After the first one hundred days post HCT, patients were evaluated quarterly for late onset aGVHD (defined as acute GVHD onset after day 100) or cGVHD until one year after HCT. No additional aGVHD events were observed in the CD24Fc cohorts after Day 100 post-transplant.

Figure 16:
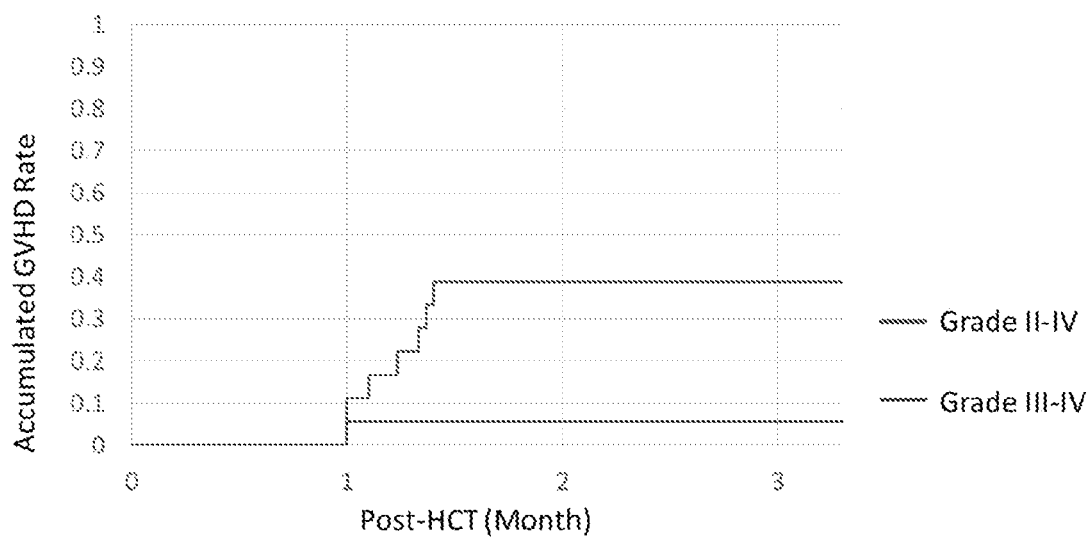
FIG. 16 shows the incidence of Grade II-IV and Grade III-IV acute GVHD in the treatment (CD24Fc) cohort.
Figure 17:
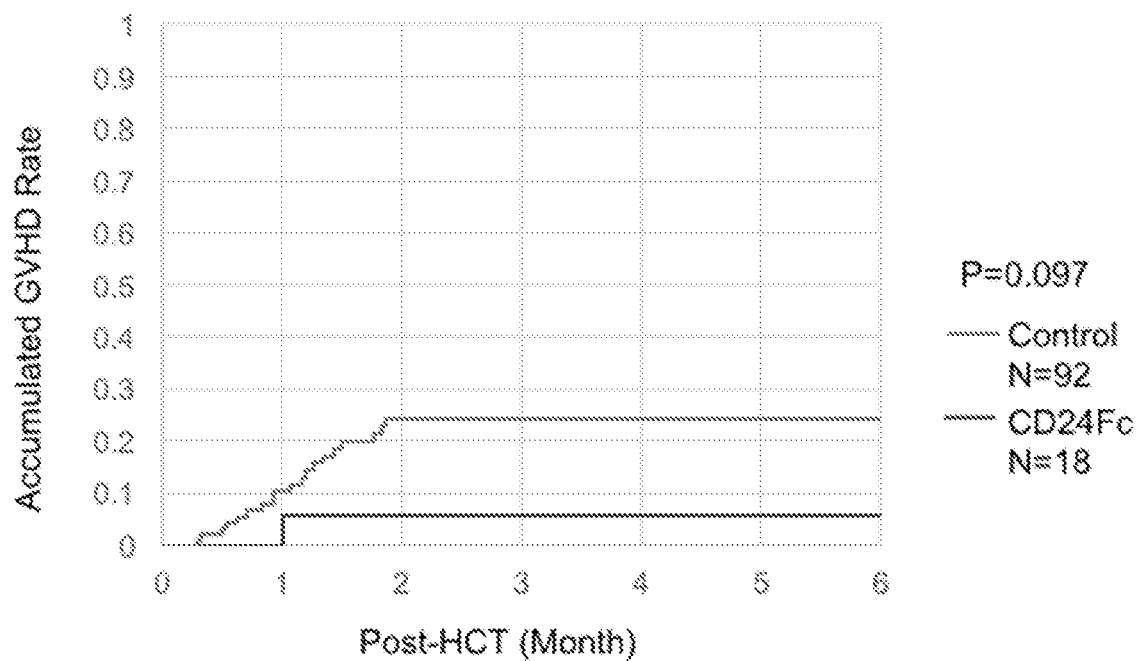
FIG. 17 shows the cumulative incidence of grade III-IV aGVHD 180 days post HCT in patients receiving methotrexate/tacrolimus+CD24Fc as compared to contemporary control patients receiving methotrexate/tacrolimus.

FIG. 16 shows the cumulative incidence of Grade II-IV and Grade III-IV acute GVHD in the treatment (CD24Fc) cohort. In particular, only one patient had Grade III GVHD that involved the lower GI and no liver GVHD was observed. The cumulative incidence of grade III-IV aGVHD at Day 180 after HCT in the CD24Fc cohorts trended lower than the grade III-IV aGVHD at Day 180 in the contemporary control (P=0.097). There was an additional case of Grade III aGVHD at Day 182, which resulted in death at day 184, in a patient in the placebo group. This patient had a leukemia relapse at Day 145. These results suggest that CD24Fc in addition to methotrexate and tacrolimus prophylaxis reduces the risk of developing more serious grade III and IV aGVHD in patients undergoing HCT after receiving myeloablative conditioning.

Disease-Free Survival 1 Year Following Hematopoietic Stem Cell Transplantation

Table 12 summarizes disease-free survival (DFS) 1 year post-HCT for the mITT Population. The median DFS Kaplan-Meier estimate was not reached for any treatment group. Overall, the DFS rate at 1 year post-HCT (with 95% CI) was 83.3% (56.8%, 94.3%) for the CD24Fc treatment group and 50.0% (11.1%, 80.4%) for the placebo group. The hazard ratio (with 90% CI) for CD24Fc versus placebo was 0.2 (0.1, 0.9). Patients who were alive and did not experience disease relapse at the end of the follow-up period were censored at the last date of evaluation. At least 50.0% of patients in each treatment group were censored. FIG. 31 shows the Relapse Free Survival in the CD24Fc group compared to the placebo control group (FIG. 31A) and the contemporary control group (FIG. 31B).

TABLE 12

Disease-Free Survival 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with events (n, %) | 3 (50.0) | 1 (16.7) | 1 (16.7) | 1 (16.7) | 3 (16.7) |
| Earliest contributing event | | | | | |
| Relapse | 2 (33.3) | 0 (0.0) | 1 (16.7) | 1 (16.7) | 2 (11.1) |
| Death | 1 (16.7) | 1 (16.7) | 0 (0.0) | 0 (0.0) | 1 (5.6) |
| No. of patients censored (n, %) | 3 (50.0) | 5 (83.3) | 5 (83.3) | 5 (83.3) | 15 (83.3) |

TABLE 12-continued

Disease-Free Survival 1 Year Following Hematopoietic Stem Cell
Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Disease-free survival (days) Kaplan-Meier estimate [1] | | | | | |
| Median (95% CI) | NE | NE | NE | NE | NE |
| Mean (SD) [2] | 232.7 (152.48) | 342.5 (64.11) | 335.2 (92.82) | 324.2 (109.89) | 333.9 (85.76) |
| Median [2] | 256.0 | 366.0 | 370.5 | 366.0 | 366.0 |
| Min, max [2] | 49, 371+ | 212, 378+ | 146, 380+ | 100, 376+ | 100, 380+ |
| Treatment comparison: CD24Fc versus placebo [3] | | | | | |
| Hazard ratio (90% CI) | | | | | 0.2 (0.1, 0.9) |
| Rate (%) of being alive without relapse at 1 year post-HCT (95% CI) [4] | 50.0 (11.1, 80.4) | 83.3 (27.3, 97.5) | 83.3 (27.3, 97.5) | 83.3 (27.3, 97.5) | 83.3 (56.8, 94.3) |

Note:
One year = Day 365 (+14 days) post-transplant (ie, Study Day 380).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate. For Day 365, if the maximum observed time was <Study Day 380, the Kaplan-Meier estimate at the maximum observed time is presented for a treatment group.
CI = confidence interval;
HCT = hematopoietic stem cell transplantation;
log = logarithm;
max = maximum;
min = minimum;
NE = not estimable;
No. = number,
SD = standard deviation.

Overall Survival 1 Year Following Hematopoietic Stem Cell Transplantation

Table 13 summarizes overall survival (OS) 1 year post-HCT for the mITT Population. The median OS time Kaplan-Meier estimate was not reached for any treatment group. Overall, the OS rate at 1 year (with 95% CI) was 83.3% (56.8%, 94.3%) for the CD24Fc treatment group and 50.0% (11.1%, 80.4%) for the placebo group. The hazard ratio (with 90% CI) for CD24Fc versus placebo was 0.2 (0.1, 1.0). Patients who were alive at the end of the follow-up period were censored at the last date that they were known to be alive. At least 50.0% of patients in each treatment group were censored.

TABLE 13

Disease-Free Survival 1 Year Following Hematopoietic Stem Cell
Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients who died (n, %) | 3 (50.0) | 1 (16.7) | 1 (16.7) | 1 (16.7) | 3 (16.7) |
| No. of patients censored (n, %) | 3 (50.0) | 5 (83.3) | 5 (83.3) | 5 (83.3) | 15 (83.3) |
| Overall survival (days) Kaplan-Meier estimate [1] | | | | | |
| Median (95% CI) | NE | NE | NE | NE | NE |
| Mean (SD) [2] | 276.3 (132.25) | 343.0 (64.34) | 343.5 (72.45) | 367.2 (6.01) | 351.2 (53.91) |
| Median [2] | 341.5 | 366.5 | 370.5 | 366.0 | 366.5 |
| Min, max [2] | 49, 371+ | 212, 378+ | 196, 380+ | 358+, 376+ | 196, 380+ |

TABLE 13-continued

Disease-Free Survival 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Treatment comparison: CD24Fc versus placebo [3] | | | | | |
| Hazard ratio (90% CI) | | | | | 0.2 (0.1, 1.0) |
| Rate (%) of being alive at 1 year post-HCT (95% CI) [4] | 50.0 (11.1, 80.4) | 83.3 (27.3, 97.5) | 83.3 (27.3, 97.5) | 83.3 (27.3, 97.5) | 83.3 (56.8, 94.3) |

Note:
One year = Day 365 (+14 days) post-transplant (ie, Study Day 380).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate. For Day 365, if the maximum observed time was <Study Day 380, the Kaplan-Meier estimate at the maximum observed time is presented for a treatment group.
CI = confidence interval;
HCT = hematopoietic stem cell transplantation;
log = logarithm;
max = maximum;
min = minimum;
NE = not estimable;
No. = number,
SD = standard deviation.

Figure 20:
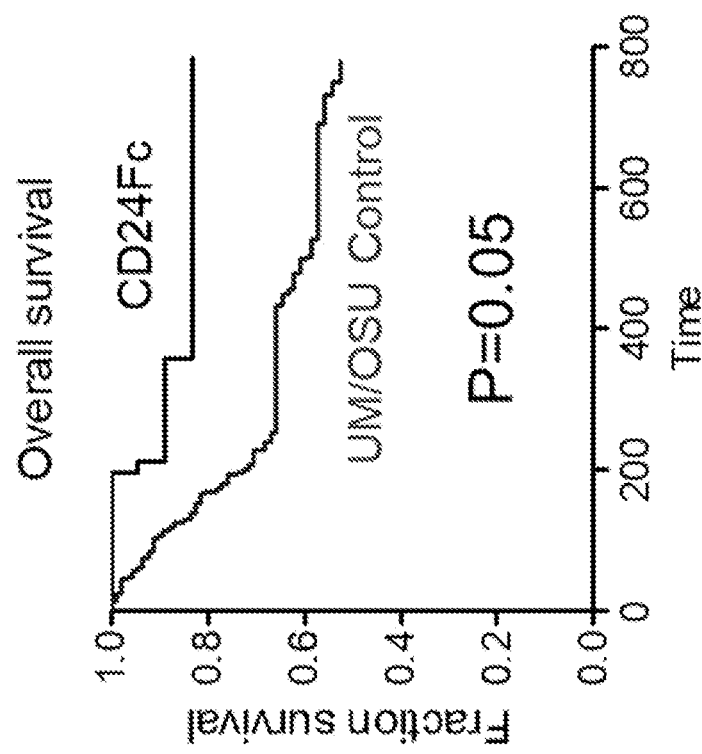
FIG. 20 shows the Kaplan-Meier survival analysis comparing 1.5 year overall survival of patients receiving either CD24Fc or placebo control.
Figure 21:
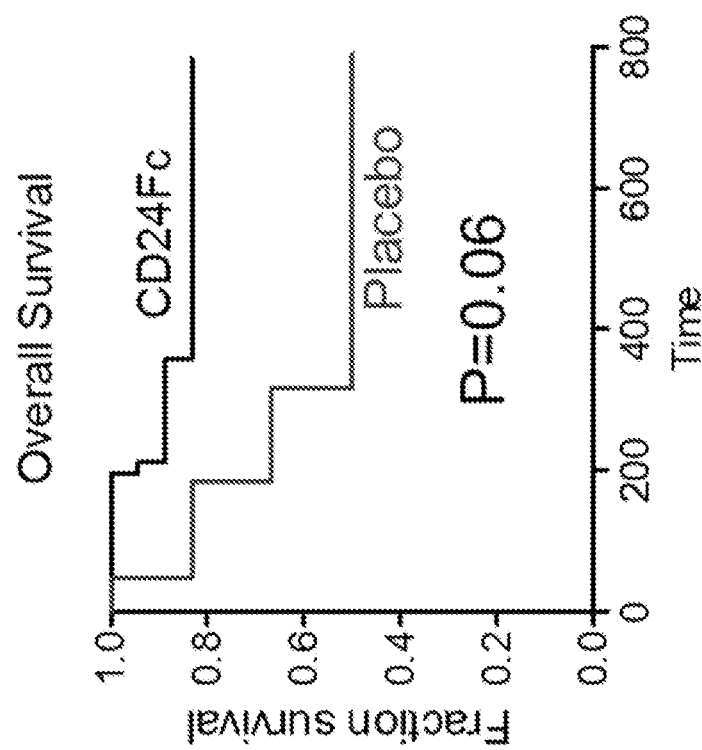
FIG. 21 shows the Kaplan-Meier survival analysis comparing 1.5 year overall survival of patients receiving CD24Fc to contemporary control.

Estimates of overall survival (OS) at about 800 days post HCT for patients in the phase IIa study are also encouraging. Overall survival (OS) was about 80% for patients in the CD24Fc cohorts, 50% for patients in the placebo cohort (p=0.06) (FIG. 20), and 50% for patients in the contemporary control (p=0.05) (FIG. 21). The improved OS in the CD24Fc exposed patients as compared to the placebo and contemporary control patients supports the other findings described above which show that administration of CD24Fc in combination with methotrexate and tacrolimus may yield a substantial improvement on the outcome in patients undergoing HCT following myeloablative conditioning.

Acute Graft-Versus-Host Disease-Free Survival and Relapse Free Survival (aGRFS) Through Day 180

Therapeutic strategies designed to prevent GVHD may result in an increase in leukemia relapse due to a reduction in the Graft Versus Leukemia (GVL) effect. As shown in Table 7, the incidence of leukemia relapse in patients exposed to CD24Fc at Day 180 post HCT (11%) is lower as compared to patients in the placebo group (33%) and the contemporary control (23%). One subject in the 480 mg CD24Fc cohort experienced relapse of CMML on Day 146 and one subject in the multi-dose 960 mg CD24Fc cohort experienced relapse of ALL on Day 100 post HCT. The patient with CMML passed away on Day 196 due to leukemia. The patient with ALL relapse was treated with blinatumomab, achieved complete remission, and was alive as of the data cutoff of Aug. 8, 2018. In the placebo cohort, one patient experienced relapse of CMML on Day 94 and one patient with MDS relapsed on Day 146 (the patient with CMML passed away on Day 316 and the patient with MDS passed away on Day 184). These results suggest CD24Fc does not interfere with the beneficial graft-versus-tumor (GVT) process, and may even reduce the risk of leukemia relapse.

Figure 18:
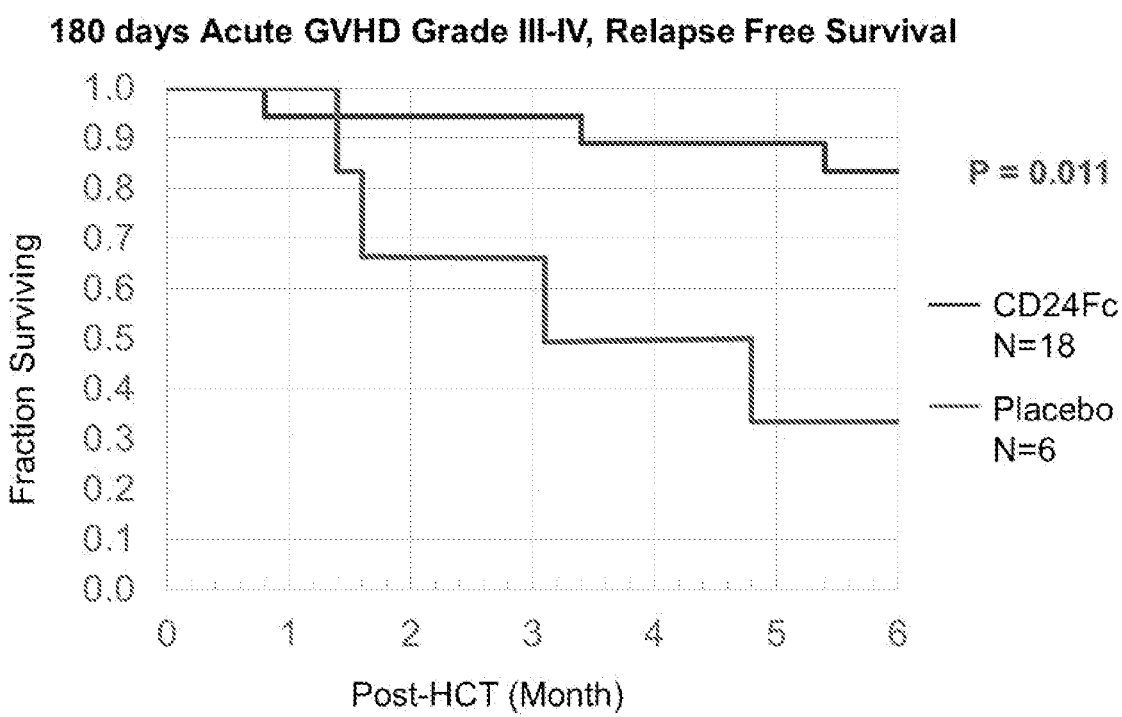
FIG. 18 shows the Kaplan-Meier survival analysis comparing 180 days Grade III-IV aGVHD, relapse-free survival in patients receiving either CD24Fc or placebo control.
Figure 19:
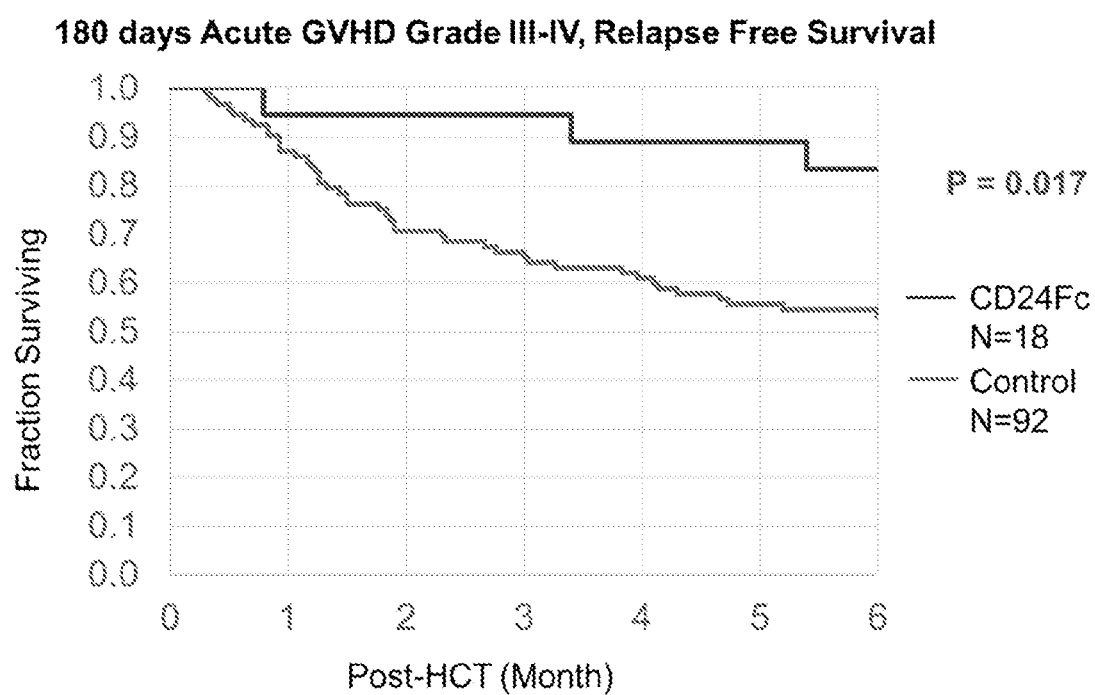
FIG. 19 shows the Kaplan-Meier survival analysis comparing 180 days Grade III-IV aGVHD, relapse-free survival in patients receiving CD24Fc with contemporary control.

The number of deaths in the CD24Fc cohorts at Day 180 post transplant is lower than in the placebo and contemporary control cohorts (Table 7). At Day 180 post HCT, there were no deaths in any of the CD24Fc cohorts, one death due to pneumonia in the placebo cohort (16.7%), and 22 deaths in the contemporary control (23.9%). Statistically significant improvements in the composite endpoint of aGVHD grade relapse-free survival (RFS) are observed in the CD24Fc cohorts (83%) as compared to the placebo group (33%) at Day 180 post HCT (P=0.011, see FIG. 18) and the contemporary control (53%) at Day 180 post HCT (P=0.017, see FIG. 19). This sort of endpoint has become increasingly popular because it in theory encapsulates the effect of an intervention not only on GVHD suppression but potential impact toxicity, infection and relapse. In support of the observations above, improvements in grade III-IV aGVHD, RFS show that administering CD24Fc in combination with a standard or care methotrexate and tacrolimus following a myeloablative conditioning regimen is beneficial to patients in preventing the occurrence of aGVHD while not affecting the GVL effects of the graft.

The aGRFS through Day 180 post-HCT is a post hoc composite endpoint in which events included Grade III to IV acute GVHD, relapse, or death from any cause. Table 14 summarizes the Grade III to IV acute GRFS through Day 180 for the mITT Population.

The Kaplan-Meier estimate of the median Grade III to IV acute GRFS was not reached for the CD24Fc treatment groups. For the placebo group, the Kaplan-Meier estimate of the median Grade III to IV acute GRFS (with 95% CI) was 120.0 (46.0, not estimable). Overall, the Grade III to IV acute GRFS rate at Day 180 (with 95% CI) was 83.3% (56.8%, 94.3%) for the CD24Fc treatment group and 33.3% (4.6%, 67.6%) for the placebo group. The hazard ratio (with 90% CI) for CD24Fc versus placebo was 0.2 (0.0, 0.6). Patients who were alive and had no documented occurrence of Grade III to IV acute GVHD, chronic GVHD requiring systemic immunosuppressive therapy, or relapse at the data cutoff date were censored at the last assessment date.

TABLE 14

Grade III to IV Acute Graft-Versus-Host Disease-Free Survival and Relapse
Free Survival Through Day 180 - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with events (n, %) | 4 (66.7) | 0 (0.0) | 2 (33.3) | 1 (16.7) | 3 (16.7) |
| Earliest contributing event | | | | | |
| Acute GVHD (Grade III-IV) | 1 (16.7) | 0 (0.0) | 1 (16.7) | 0 (0.0) | 1 (5.6) |
| Relapse | 2 (33.3) | 0 (0.0) | 1 (16.7) | 1 (16.7) | 2 (11.1) |
| Death | 1 (16.7) | 0 (0.0) | 0 (0.0) | 0 (0.0) | 0 (0.0) |
| No. of patients censored (n, %) | 2 (33.3) | 6 (100.0) | 4 (66.7) | 5 (83.3) | 15 (83.3) |
| Grade III-IV acute GVHD-free survival relapse-free survival (days) | | | | | |
| Kaplan-Meier estimate [1] | | | | | |
| Median (95% CI) | 120.0 (46.0, NE) | NE | NE | NE | NE |
| Mean (SD) [2] | 120.8 (67.99) | 195.0 (0.00) | 158.3 (68.67) | 179.2 (38.78) | 177.5 (45.47) |
| Median [2] | 120.0 | 195.0 | 195.0 | 195.0 | 195.0 |
| Min, max [2] | 46, 195+ | 195+, 195+ | 24, 195+ | 100, 195+ | 24, 195+ |
| Treatment comparison: CD24Fc versus placebo [3] | | | | | |
| Hazard ratio (90% CI) | | | | | 0.2 (0.0, 0.6) |
| Rate (%) of being alive without Grade III-IV acute GVHD or relapse at Day 180 (95% CI) [4] | 33.3 (4.6, 67.6) | 100.0 (NE) | 66.7 (19.5, 90.4) | 83.3 (27.3, 97.5) | 83.3 (56.8, 94.3) |

Note:
Day 180 = Day 180 (+14 days) post-transplant (ie, Study Day 195).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate.
CI = confidence interval;
GVHD = graft-versus-host disease;
log = logarithm;
max = maximum;
min = minimum;
NE = not estimable;
No. = number;
SD = standard deviation.

Incidence of Relapse 1 Year Following Hematopoietic Stem Cell Transplantation

Table 15 summarizes the cumulative incidence of relapse 1 year post-HCT for the mITT Population. Overall, the cumulative incidence rate of relapse at 1 year post-HCT (with 95% CI) was 11.1% (1.7%, 30.4%) for the CD24Fc treatment group and 33.3% (2.9%, 71.1%) for the placebo group. The hazard ratio (with 90% CI) for CD24Fc versus placebo was 0.3 (0.1, 1.4). Patients who were alive and did not experience relapse at the end of the follow-up period (Day 365 [1 year]) were censored at the last date of evaluation. At least 50.0% of patients in each treatment group were censored.

TABLE 15

Cumulative Incidence of Relapse 1 Year Following Hematopoietic Stem Cell
Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with relapse by 1 year post-HCT (n, %) | 2 (33.3) | 0 (0.0) | 1 (16.7) | 1 (16.7) | 2 (11.1) |
| No. of patients who died without relapse by 1 year post-HCT (n, %) | 1 (16.7) | 1 (16.7) | 0 (0.0) | 0 (0.0) | 1 (5.6) |

TABLE 15-continued

Cumulative Incidence of Relapse 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients censored (n, %) | 3 (50.0) | 5 (83.3) | 5 (83.3) | 5 (83.3) | 15 (83.3) |
| Cumulative incidence (%) of relapse at 1 year post-HCT (95% CI) [1] | 33.3 (2.9, 71.1) | 0.0 (NE) | 16.7 (0.5, 54.9) | 16.7 (0.5, 54.9) | 11.1 (1.7, 30.4) |
| Treatment comparison: CD24Fc versus placebo [2] | | | | | |
| Hazard ratio (90% CI) | | | | | 0.3 (0.1, 1.4) |

Note:
One year = Day 365 (+14 days) post-transplant (ie, Study Day 380).
Percentage was calculated using the number of patients in the column heading as the denominator.
1. The cumulative incidence (%) of relapse 1 year post-HCT and the 95% CI were estimated using the cumulative incidence function with death without relapse as a competing risk. For Day 365, if the maximum observed time was <Study Day 380, the cumulative incidence at the maximum observed time is presented for a treatment group.
2. Hazard ratio and 90% CI were based on a Fine and Gray model with treatment as a covariate and death without relapse as a competing risk.
CI = confidence interval;
HCT = hematopoietic stem cell transplantation;
NE = not estimable;
No. = number.

Graft-Versus-Host Disease-Free Survival and Relapse-Free Survival (GRFS) 1 Year Following Hematopoietic Stem Cell Transplantation This GRFS through 1 year post-HCT is a composite endpoint in which events included Grade III to IV acute GVHD, chronic GVHD requiring systemic immunosuppressive therapy, relapse, or death from any cause. Table 16 summarizes Grade III to IV acute GRFS 1 year post-HCT for the mITT Population.

The Kaplan-Meier estimate of the median GRFS (with 95% CI) was 229.0 days (141.0, not estimable) for the overall CD24Fc treatment group: 247.0 days (129.0, not estimable) for the 240 mg CD24Fc single dose cohort, 287.0 (24.0, not estimable) for the 480 mg CD24Fc single dose cohort, and 193.5 (100.0, not estimable) for the 960 mg CD24Fc multiple dose cohort. The Kaplan-Meier estimate of the median GRFS (with 95% CI) was 120.0 days (46.0, not estimable) for the placebo group. Overall, the GRFS rate at 1 year post-HCT (with 95% CI) was 32.4% (12.7%, 54.0%) for the CD24Fc treatment group and 33.3% (4.6%, 67.6%) for the placebo group. The hazard ratio (with 90% CI) for CD24Fc versus placebo was 0.7 (0.3, 1.7). Patients who were alive and had no documented occurrence of Grade III to IV acute GVHD, chronic GVHD requiring systemic immunosuppressive therapy, or relapse at the data cutoff date were censored at the last assessment date.

TABLE 16

Graft-Versus-Host Disease-Free Survival and Relapse-Free Survival 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with events (n, %) | 4 (66.7) | 4 (66.7) | 4 (66.7) | 4 (66.7) | 12 (66.7) |
| Earliest contributing event | | | | | |
| Acute GVHD (Grade III-IV) | 1 (16.7) | 0 (0.0) | 1 (16.7) | 0 (0.0) | 1 (5.6) |
| Chronic GVHD requiring systemic immunosuppressive therapy | 0 (0.0) | 3 (50.0) | 2 (33.3) | 3 (50.0) | 8 (44.4) |
| Relapse | 2 (33.3) | 0 (0.0) | 1 (16.7) | 1 (16.7) | 2 (11.1) |
| Death | 1 (16.7) | 1 (16.7) | 0 (0.0) | 0 (0.0) | 1 (5.6) |
| No. of patients censored (n, %) | 2 (33.3) | 2 (33.3) | 2 (33.3) | 2 (33.3) | 6 (33.3) |
| GVHD-free survival and relapse-free survival (days) | | | | | |
| Kaplan-Meier estimate [1] | | | | | |
| Median (95% CI) | 120.0 (46.0, NE) | 247.0 (129.0, NE) | 287.0 (24.0, NE) | 193.5 (100.0, NE) | 229.0 (141.0, NE) |
| Mean (SD) [2] | 178.7 (151.48) | 260.5 (99.54) | 250.3 (149.68) | 227.2 (123.63) | 246.0 (119.19) |

TABLE 16-continued

Graft-Versus-Host Disease-Free Survival and Relapse-Free Survival 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Median [2] | 120.0 | 247.0 | 287.0 | 193.5 | 229.0 |
| Min, max [2] | 46, 371+ | 129, 378+ | 24, 380+ | 100, 376+ | 24, 380+ |
| Treatment comparison: CD24Fc versus placebo [3] | | | | | |
| Hazard ratio (90% CI) | | | | | 0.7 (0.3, 1.7) |
| Rate (%) of being alive without GVHD or relapse at 1 year post-HCT (95% CI) [4] | 33.3 (4.6, 67.6) | 33.3 (4.6, 67.6) | 33.3 (4.6, 67.6) | 33.3 (4.6, 67.6) | 32.4 (12.7, 54.0) |

Note:
One year = Day 365 (+14 days) post-transplant (ie, Study Day 380).
Percentage was calculated using the number of patients in the column heading as the denominator.
1. The 95% CI for median was computed using the Brookmeyer and Crowley method with log-log transformation.
2. Censoring was ignored in the calculation for mean (SD) and median. A "+" after the min or max indicates a censored observation.
3. Hazard ratio and 90% CI were based on a Cox proportional hazards model with treatment as a covariate.
4. Kaplan-Meier estimate.
CI = confidence interval;
GVHD = graft-versus-host disease;
HCT = hematopoietic stem cell transplantation;
log = logarithm;
max = maximum;
min = minimum;
NE = not estimable;
No. = number;
SD = standard deviation.

Incidence of Non-Relapse Mortality 1 Year Following Hematopoietic Stem Cell Transplantation Table 17 summarizes the cumulative incidence of NRM 1 year post-HCT for the mITT Population. Overall, the cumulative incidence rate of NRM at 1 year (with 95% CI) was 5.6% (0.3%, 23.1%) for the CD24Fc treatment group and 16.7% (0.5%, 54.9%) for the placebo group. The hazard ratio (with 90% CI) for CD24Fc versus placebo was 0.3 (0.0, 2.8). Patients who were alive at the end of the follow-up period (Day 365 [1 year]) without relapse were censored at the last date they were known to be alive. At least 50.0% of patients in each treatment group were censored. The cumulative incidence rate of NRM at Day 180 (with 95% CI) was 0.0% for the CD24Fc treatment group and 16.7% (0.5%, 54.9%) for the placebo group.

TABLE 17

Cumulative Incidence of Non-Relapse Mortality 1 Year Following Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients who died without relapse by 1 year post-HCT (n, %) | 1 (16.7) | 1 (16.7) | 0 (0.0) | 0 (0.0) | 1 (5.6) |
| No. of patients with relapse by 1 year post-HCT (n, %) | 2 (33.3) | 0 (0.0) | 1 (16.7) | 1 (16.7) | 2 (11.1) |
| No. of patients censored (n, %) | 3 (50.0) | 5 (83.3) | 5 (83.3) | 5 (83.3) | 15 (83.3) |

TABLE 17-continued

Cumulative Incidence of Non-Relapse Mortality 1 Year Following
Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| Cumulative incidence (%) of NRM at 1 year post-HCT (95% CI) [1] | 16.7 (0.5, 54.9) | 16.7 (0.5, 54.9) | 0.0 (NE) | 0.0 (NE) | 5.6 (0.3, 23.1) |
| Treatment comparison: CD24Fc versus placebo [2] | | | | | |
| Hazard ratio (90% CI) | | | | | 0.3 (0.0, 2.8) |

Note:
One year = Day 365 (+14 days) post-transplant (ie, Study Day 380).
Percentage was calculated using the number of patients in the column heading as the denominator.
1. The cumulative incidence (%) of NRM at 1 year post-HCT and the 95% CI were estimated using the cumulative incidence function with relapse as a competing risk. For Day 365, if the maximum observed time was <Study Day 380, the cumulative incidence at the maximum observed time is presented for a treatment group.
2. Hazard ratio and 90% CI were based on a Fine and Gray model with treatment as a covariate and relapse as a competing risk.
CI = confidence interval;
HCT = hematopoietic stem cell transplantation;
NE = not estimable;
No. = number;
NRM = non-relapse mortality.

Incidence of Chronic Graft-Versus-Host Disease 1 Year Following Hematopoietic Stem Cell Table 18 summarizes the cumulative incidence of chronic GVHD 1 year post-HCT for the mITT Population. Overall, the cumulative incidence rate of chronic GVHD at 1 year post-HCT (with 95% CI) was 63.3% (34.1%, 82.4%) for the CD24Fc treatment group and 33.3% (2.5%, 72.0%) for the placebo group. The hazard ratio (with 90% CI) for CD24Fc versus placebo was 2.1 (0.6, 7.4). There were 3 moderate chronic GVHD in the 240 mg CD24Fc single dose cohort, 3 mild and 1 moderate chronic GVHD in the 480 mg CD24Fc single dose cohort, and 2 mild and 3 moderate chronic GVHD in the 960 mg CD24Fc multiple doses cohort. Two patients had mild chronic GVHD in the placebo group. Overall, there were no instances of severe chronic GVHD. Patients who were alive and did not experience chronic GVHD at the end of the follow-up period (Day 365 [1 year]) were censored at the last date of evaluation.

TABLE 18

Cumulative Incidence of Chronic Graft-Versus-Host Disease 1 Year Following
Hematopoietic Stem Cell Transplantation - mITT Population

| Statistic | Placebo (N = 6) | CD24Fc 240 mg Single Dose (N = 6) | CD24Fc 480 mg Single Dose (N = 6) | CD24Fc 960 mg Multiple Doses (N = 6) | CD24Fc Total (N = 18) |
|---|---|---|---|---|---|
| No. of patients with chronic GVHD by 1 year post-HCT (n, %) | 2 (33.3) | 3 (50.0) | 3 (50.0) | 5 (83.3) | 11 (61.1) |
| No. of patients who died without chronic GVHD by 1 year post-HCT (n, %) | 3 (50.0) | 1 (16.7) | 1 (16.7) | 1 (16.7) | 3 (16.7) |
| No. of patients censored (n, %) | 1 (16.7) | 2 (33.3) | 2 (33.3) | 0 (0.0) | 4 (22.2) |
| Cumulative incidence (%) of chronic GVHD at 1 year post-HCT [1] | 33.3 | 50.0 | 50.0 | 83.3 | 63.3 |
| 95% CI | (2.5, 72.0) | (7.0, 83.5) | (6.9, 83.6) | (0.5, 99.4) | (34.1, 82.4) |
| Treatment comparison: CD24Fc versus placebo [2] | | | | | |
| Hazard ratio (90% CI) | | | | | 2.1 (0.6, 7.4) |

Note:
One year = Day 365 (+14 days) post-transplant (ie, Study Day 380).
Percentage was calculated using the number of patients in the column heading as the denominator.
1. The cumulative incidence (%) of chronic GVHD at 1 year post-HCT and the 95% CI were estimated using the cumulative incidence function with death without chronic GVHD as a competing risk. If the maximum observed time was <Study Day 380, the cumulative incidence at the maximum observed time is presented for a treatment group.
2. Hazard ratio and 90% CI were based on a Fine and Gray model with treatment as a covariate and death without chronic GVHD as a competing risk.
CI = confidence interval;
GVHD = graft-versus-host disease;
HCT = hematopoietic stem cell transplantation;
No. = number.

Rate of Infection at Day 100

As with the effect on GVL, therapeutic strategies designed to prevent GVHD through global immune suppression may result in an increase in infection rates, including bacterial infections and CMV reactivation.

Table 19 summarizes the incidence of infections through Day 100 for the mITT Population. In total, 13 (72.2%) patients who received CD24Fc (5 [83.3%] patients in the 240 mg CD24Fc single dose cohort, 2 [33.3%] patients in the 480 mg CD24Fc single dose cohort, and 6 [100.0%] patients in the 960 mg CD24Fc multiple dose cohort) and 2 (33.3%) patients who received placebo had an infection through Day 100.

Most infections were considered to be controlled and resolved. Patient 103-001 in the placebo group died from pneumonia. Patient 102-002 in the placebo group had conjunctivitis that was reported as recovering/resolving. Patient 101-010 in the 480 mg CD24Fc single dose cohort and Patient 101-011 in the 480 mg CD24Fc single dose cohort both had rash pustular that was reported as not recovered/not resolved. Patient 102-006 in the 960 mg CD24Fc multiple dose cohort had upper respiratory tract infection and *Clostridium difficile* colitis that were reported as intervention continued.

The majority of the infections were bacterial (9 [50.0%] patients who received CD24Fc and 2 [33.3%] patients who received placebo) or viral (7 [38.9%] patients who received CD24Fc and 1 [16.7%] patient who received placebo). The majority of infections occurred in the blood (8 [44.4%] patients who received CD24Fc and 1 [16.7%] patient who received placebo), urine (4 [22.2%] patients who received CD24Fc and no patients who received placebo), or feces (2 [11.1%] patients who received CD24Fc and 2 [33.3%] patients who received placebo). The majority of the bacteria recovered from blood culture were common skin inhabitants and low virulence pathogens (i.e., coagulase negative staphylococci).

As shown As shown in Table 20, there were 9 patients in the CD24Fc group that had high risk of CMV reactivation (Donor/Recipient CMV status before HCT: D+/R+, 5; D−/R+, 3; unknown D/R+, 1). One patient in the CD24Fc group with D+/R− had intermediate risk for CMV reactivation. Eight patients in the CD24Fc group had status of D−/R−, which was considered to be low risk. Two D−/R+ patients had CMV reactivation at Day 42 and Day 48, representing 22.2% cumulative incidence of CMV reactivation at Day 100 in the high risk group. Both patients had systemic steroid treatment prior to the detection of CMV reactivation. In comparison, 2 patients in the placebo group were high risk of CMV reactivation (D+/R+, 1; D−/R+, 1). One patient in the placebo group had CMV reactivation at Day 47 before systemic steroid treatment for acute GVHD (50.0% in high risk group).

TABLE 20

CMV infection rates in HCT patients stratified by donor and recipient CMV status before transplant.

| Cytomegalovirus status | CD24Fc Group | Placebo Group |
|---|---|---|
| D+, R+ | 5 | 1 |
| D+, R− | 1 | 0 |
| D−, R+ | 3 | 1 |
| D−, R− | 8 | 4 |
| DU, R+ | 1 | 0 |

D = donor,
R = recipient,
+ is positive,
− is negative,
U is unknown.

Overall, CD24Fc was well tolerated in the phase IIa study. There were no infusion-related toxicities. There was one possible drug related TEAE≥grade III in patients exposed to CD24Fc in the 480 mg group of hyperglycemia, which was managed with insulin. One dose-limiting toxicity (DLT) was

TABLE 19

Summary of Incidence of Infections Through Day 100 - mITT Population

| Statistic | Placebo (N = 6) n (%) | CD24Fc 240 mg Single Dose (N = 6) n (%) | CD24Fc 480 mg Single Dose (N = 6) n (%) | CD24Fc 960 mg Multiple Doses (N = 6) n (%) | CD24Fc Total (N = 18) n (%) |
|---|---|---|---|---|---|
| No. of patients with any infections through Day 100 | 2 (33.3) | 5 (83.3) | 2 (33.3) | 6 (100.0) | 13 (72.2) |
| Type of infection | | | | | |
| Bacterial | 2 (33.3) | 2 (33.3) | 2 (33.3) | 5 (83.3) | 9 (50.0) |
| Fungal | 0 (0.0) | 0 (0.0) | 2 (33.3) | 0 (0.0) | 2 (11.1) |
| Viral | 1 (16.7) | 3 (50.0) | 1 (16.7) | 3 (50.0) | 7 (38.9) |
| Site of infection | | | | | |
| Blood | 1 (16.7) | 2 (33.3) | 2 (33.3) | 4 (66.7) | 8 (44.4) |
| Disseminated (2 or more sites) | 0 (0.0) | 0 (0.0) | 0 (0.0) | 1 (16.7) | 1 (5.6) |
| Feces | 2 (33.3) | 1 (16.7) | 0 (0.0) | 1 (16.7) | 2 (11.1) |
| Gastrointestinal system | 0 (0.0) | 0 (0.0) | 0 (0.0) | 1 (16.7) | 1 (5.6) |
| Genitalia | 0 (0.0) | 0 (0.0) | 1 (16.7) | 0 (0.0) | 1 (5.6) |
| Lower respiratory system | 1 (16.7) | 0 (0.0) | 0 (0.0) | 0 (0.0) | 0 (0.0) |
| Skin | 0 (0.0) | 0 (0.0) | 1 (16.7) | 1 (16.7) | 2 (11.1) |
| Upper respiratory system | 0 (0.0) | 1 (16.7) | 0 (0.0) | 2 (33.3) | 3 (16.7) |
| Urine | 0 (0.0) | 1 (16.7) | 1 (16.7) | 2 (33.3) | 4 (22.2) |

Percentage was calculated using the number of patients in the column heading as the denominator.
No. = number.

observed in the placebo group, and no DLTs were observed in the CD24Fc groups. There were no adverse events leading to death in patients administered CD24Fc within the 180 days (at least 150 days after the last dosing of CD24Fc). There was one adverse event of pneumonia that led to the death of a subject at Day 48 in the placebo group. One patient in CD24Fc group died 7 months after HCT, though the death was determined to be unlikely related to study drug. Anti-drug antibodies (ADA) were not detected in any of the 24 patients at any point out to day 100 after HCT.

The most common TEAEs≥grade III (>10%) included a decrease in platelet counts (83.3% placebo and 94.4% CD24Fc), decrease in WBC counts (66.7% placebo and 88.9% CD24Fc), decrease in neutrophil counts (50% placebo and 83.3% CD24Fc), decrease in lymphocyte counts (50% placebo and 77.8% CD24Fc), anemia (50% placebo and 66.7% CD24Fc), stomatitis (83.3% placebo and 50% CD24Fc), and nausea (0% placebo and 11.1% CD24Fc). These SAEs are consistent with the known safety profile of myeloablative conditioning regimens used in HCT.

Myeloablative conditioning for HCT is often associated with severe regimen related toxicity including organ failure. Organ failure is the most frequent cause of early onset transplantation related mortality (TRM) or non-relapse mortality (NRM). In the CD24Fc group of 18 patients, none of the patients died within the first 100 days post HCT, while 1 out of 6 in the placebo group died on Day 48 due to respiratory failure.

Pharmacokinetic Results

Figure 22A:
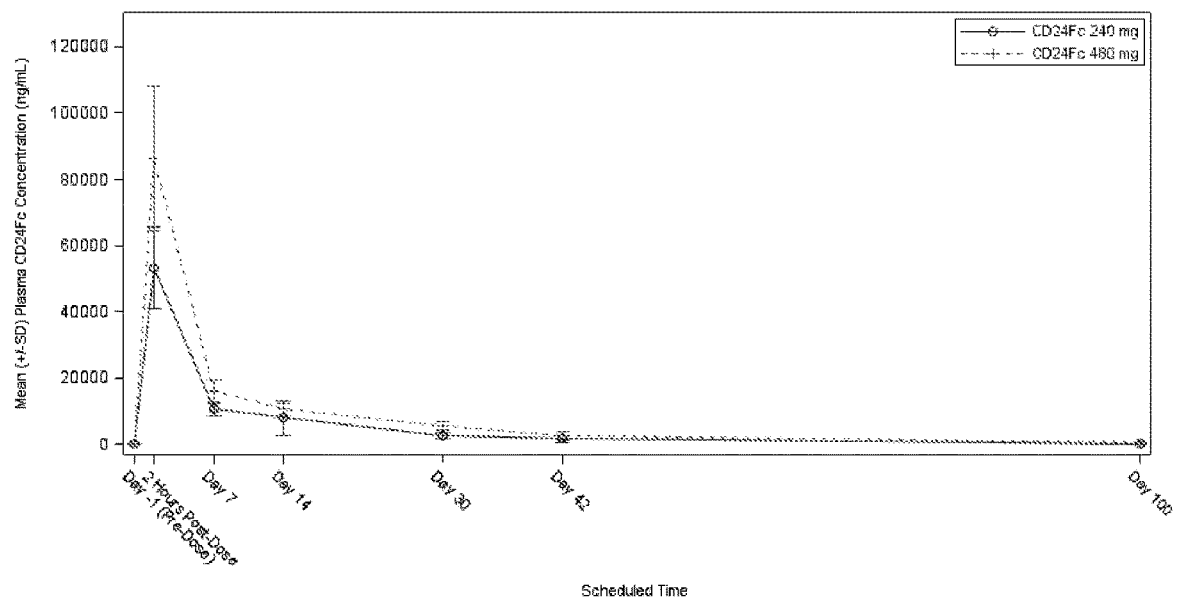
FIGS. 22A-B show the PK data from the 240 and 480 mg single dose cohorts.
Figure 22B:
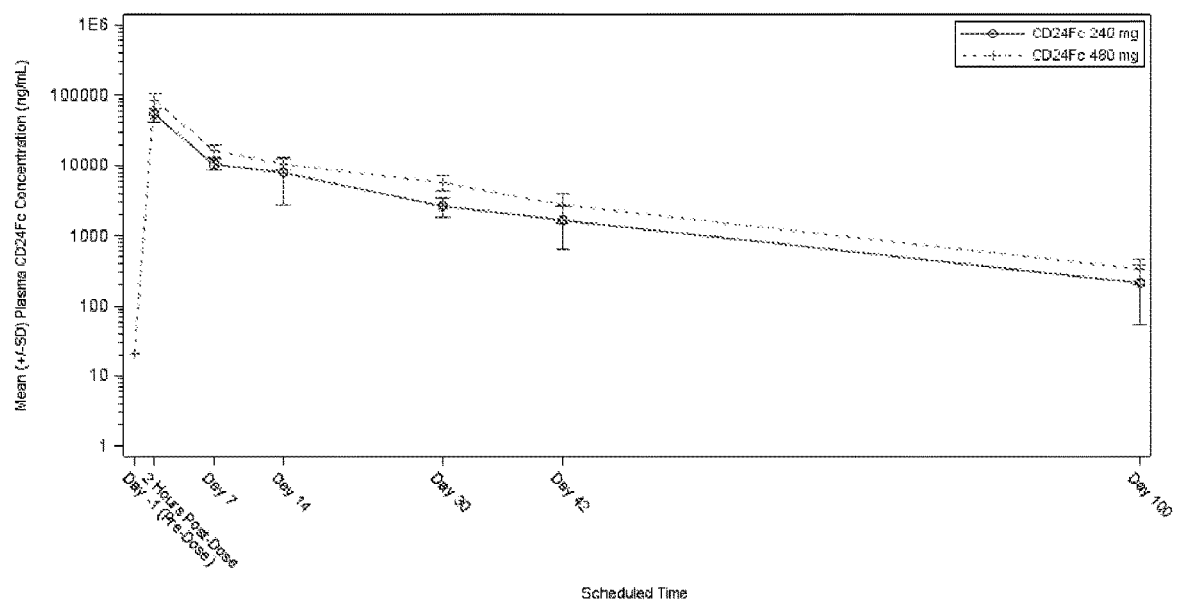
Figure 23A:
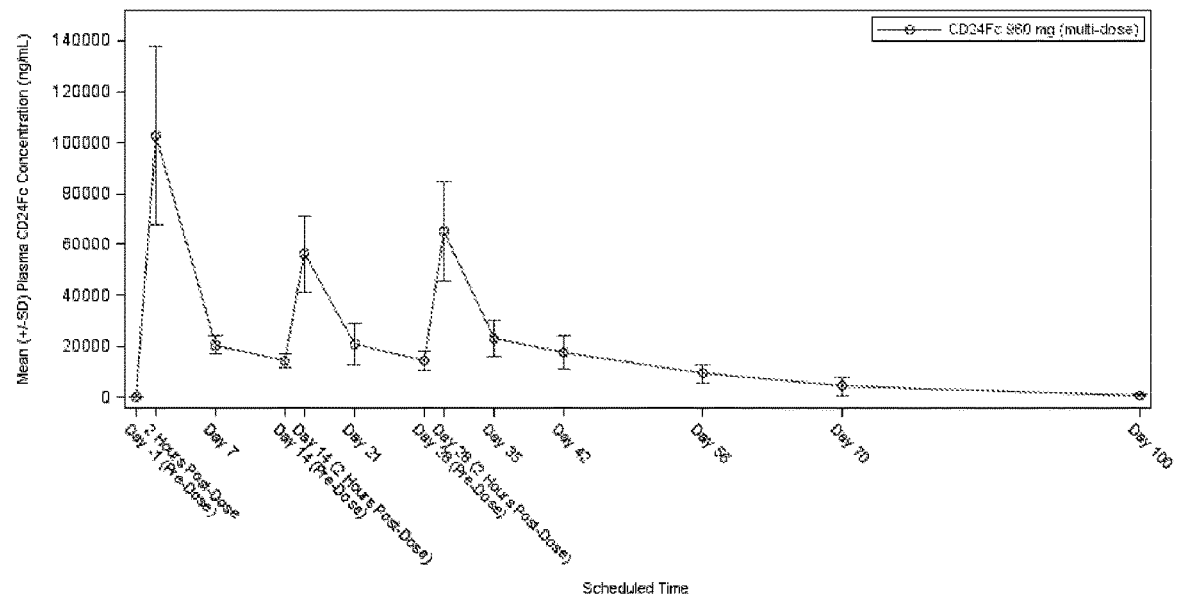
FIGS. 23A-B show the PK data from the multi-dose cohort.
Figure 23B:
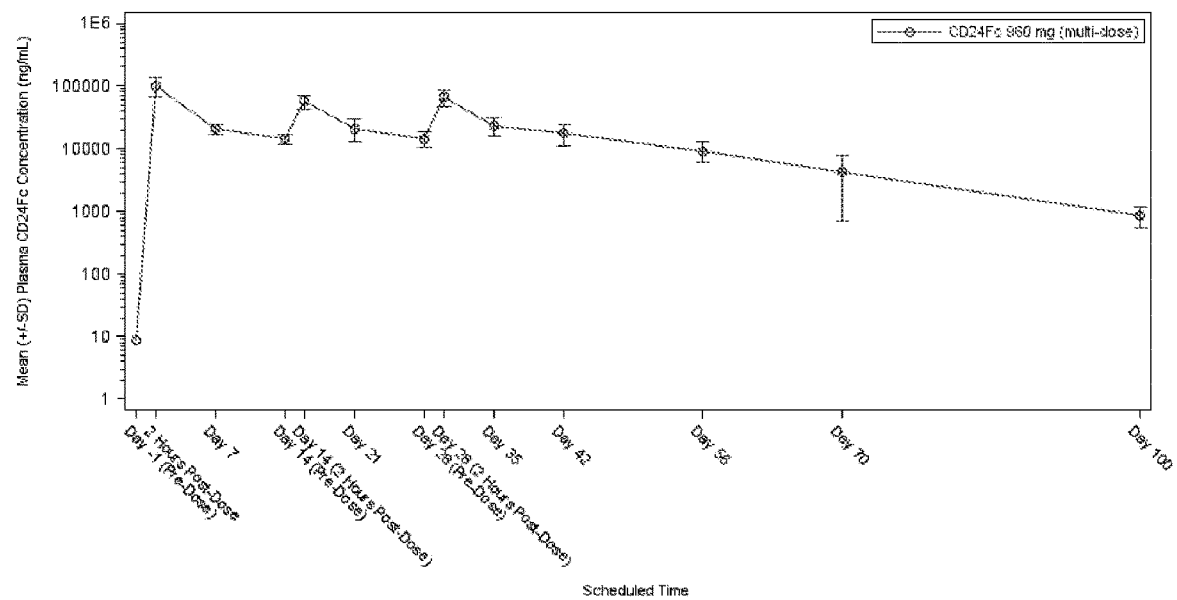

FIGS. 22-23 show the PK data from the three escalation cohorts from the Phase 2a trial. The half-life from the 240 and 480 mg single dose cohorts (FIG. 22) was around about 14 days, which is consistent with the data seen in healthy subjects. At 480 mg there was higher cmx but no real increase in exposure after 14 days, the time of peek GVHD incidence and engraftment. In the final multi-dose cohort there was increased exposure through day 60 as expected (FIG. 23), the period during which patients are most susceptible to develop GVHD.

Table 21 summarizes the plasma PK parameters of CD24Fc for the PK Population in the single dose cohorts. The geometric mean $C_{max,-1d}$ values were 52,145.41 and 84,155.08 ng/mL, the geometric mean $AUC_{0-last,-1d}$ values were 10,156,549.9 and 15,522,686.2 ng h/mL, the geometric mean $AUC_{0-42d}$ values were 9,275,562.3 and 13,903,718.4 ng h/mL, and the geometric mean $AUC_{0-inf}$ values were 10,383,503.9 and 15,716,616.4 ng h/mL for the 240 and 480 mg CD24Fc single dose cohorts, respectively. Median $t_{max, 1d}$ was 2.10 h for both the 240 and 480 mg CD24Fc single dose cohorts. The mean values of t½ were 414.739 and 406.648 h and the mean values of λz were 0.0018 and 0.0017 h−1 for the 240 and 480 mg CD24Fc single dose cohorts, respectively. The mean Vz values were 13.83 and 18.18 L, and the mean CL values were 0.024 and 0.031 L/h for the 240 and 480 mg CD24Fc single dose cohorts, respectively.

TABLE 20

Summary of Plasma Pharmacokinetic Parameters of CD24Fc - PK Population - Single Dose Cohorts

| PK Parameter (Unit) | N | CD24Fc 240 mg Single Dose Statistic | N | CD24Fc 480 mg Single Dose Statistic |
|---|---|---|---|---|
| $C_{max,-1d}$ (ng/mL) [1] | 6 | 52,145.41 (22.3) | 6 | 84,155.08 (24.6) |
| $t_{max,-1d}$ (h) [2] | 6 | 2.10 (2.1, 2.4) | 6 | 2.10 (2.0, 2.2) |
| $AUC_{0-42d}$ (ng · h/mL) [1] | 6 | 9,275,562.3 (23.2) | 6 | 13,903,718.4 (19.7) |
| $AUC_{0-last,-1d}$ (ng · h/mL) [1] | 6 | 10,156,549.9 (26.2) | 6 | 15,522,686.2 (21.3) |
| $AUC_{0-inf}$ (ng · h/mL) [1] | 6 | 10,383,503.9 (25.2) | 6 | 15,716,616.4 (21.5) |
| $AUC_{extrap}$ (%) [3] | 6 | 2.17 (1.669) | 6 | 1.23 (0.519) |
| $\lambda_z$ (h$^{-1}$) [3] | 6 | 0.0018 (0.0005) | 6 | 0.0017 (0.0002) |
| $t_{1/2}$ (h) [3] | 6 | 414.739 (110.4483) | 6 | 406.648 (62.3044) |
| $V_z$ (L) [3] | 6 | 13.83 (3.586) | 6 | 18.18 (4.529) |
| CL (L/h) [3] | 6 | 0.024 (0.0059) | 6 | 0.031 (0.0071) |

Geometric CV % = 100 * (exp(SD$^2$) − 1)$^{0.5}$, where SD is the standard deviation of the logarithm-transformed data.

1. Geometric mean (geometric CV %)

2. Median (minimum, maximum)

3. Mean (SD)

$\lambda_z$ = apparent terminal elimination rate constant;

$AUC_{0-42d}$ = the area under the plasma concentration versus time curve from time 0 to Day 42;

$AUC_{0-inf}$ = the area under the concentration versus time curve from time 0 extrapolated to infinity;

$AUC_{0-last,-1d}$ = the area under the plasma concentration versus time curve from time 0 to the last measurable plasma drug concentration for Day −1 dosing;

$AUC_{extrap}$ = percentage of $AUC_{0-inf}$ that was due to extrapolation from the last measurable plasma drug concentration to infinity;

CL = total body clearance after intravenous administration;

$C_{max,-1d}$ = maximum observed plasma concentration for Day −1 dosing;

CV % = coefficient of variation;

PK = pharmacokinetic;

SD = standard deviation;

$t_{1/2}$ = apparent terminal elimination half-life;

$t_{max,-1d}$ = the time of maximum observed plasma concentration for Day −1 dosing;

$V_z$ = volume of distribution based on the terminal elimination phase.

Table 22 summarizes the plasma PK parameters of CD24 Fc for the PK population in the multiple dose cohort on Day −1, Day 28, and Day −1 to Day 100. The geometric mean $C_{max,-1d}$ and $C_{max,28d}$ values were 96,942.71 ng/mL and 62,563.05 ng/mL, respectively, for the 960 mg CD24Fc multiple dose cohort. The geometric mean $AUC_{0-last,-1d}$, $AUC_{0-14d}$, $AUC_{0-100d}$, and $AUC_{0-last}$ overall values were 12,317,971.2 ng h/mL, 9,688,933.9 ng h/mL, 37,736,555.1 ng h/mL, and 37,363,953.5 ng h/mL, respectively, for the 960 mg CD24Fc multiple dose cohorts. The median $t_{max,-1d}$ and $t_{max,28d}$ were 2.13 h and 2.52 h, respectively, for the 960 mg CD24Fc multiple dose cohort.

TABLE 20

Summary of Plasma Pharmacokinetic Parameters of CD24Fc - PK
Population - Multiple Dose Cohort - Day −1, Day 28, and Day −1 to Day 100

| PK Parameter (Unit) | CD24Fc 960 mg Multiple Doses Day −1 | | CD24Fc 960 mg Multiple Doses Day 28 | | CD24Fc 960 mg Multiple Doses Day −1 to Day 100 | |
|---|---|---|---|---|---|---|
| | N | Statistic | N | Statistic | N | Statistic |
| $C_{max,-1d}$ (ng/ml) [1] | 6 | 96,942.71 (41.5) | — | — | — | — |
| $t_{max,-1d}$ (h) [2] | 6 | 2.13 (2.0, 3.2) | — | — | — | — |
| $AUC_{0-last,-1d}$ (ng · h/mL) [1] | 6 | 12,317,971.2 (24.9) | — | — | — | — |
| $C_{max,28d}$ (ng/ml) [1] | — | — | 6 | 62,563.05 (34.1) | — | — |
| $t_{max,28d}$ (h) [2] | — | — | 6 | 2.52 (2.0, 4.0) | — | — |
| $C_{min}$ (ng/ml) [1] | — | — | 6 | 13,233.79 (33.6) | — | — |
| $T_{min}$ (h) [2] | — | — | 6 | 0.00 (0.0, 308.2) | — | — |
| $AUC_{0-14d}$ (ng · h/mL) [1] | — | — | 6 | 9,688,933.9 (30.9) | — | — |
| $C_{avg}$ (ng/ml) [1] | — | — | 6 | 28,836.11 (30.9) | — | — |
| $Cl_{ss}$ (L/h) [3] | — | — | 6 | 0.026 (0.0078) | — | — |
| $AUC_{0-last,overall}$ (ng · h/mL) [1] | — | — | — | — | 6 | 37,363,953.5 (27.6) |
| $AUC_{0-100d}$ (ng · h/mL) [1] | — | — | — | — | 6 | 37,736,555.1 (29.3) |

Geometric CV % = 100 * (exp($SD^2$) − 1)$^{0.5}$, where SD is the standard deviation of the logarithm-transformed data.
1. Geometric mean (geometric CV %)
2. Median (minimum, maximum)
3. Mean (SD)
$AUC_{0-14d}$ = the area under the plasma concentration versus time curve from time 0 to Tau;
$AUC_{0-100d}$ = the area under the concentration versus time curve from time 0 on Day −1 to Day 100;
$AUC_{0-last,-1d}$ = the area under the plasma concentration versus time curve from time 0 to the last measurable plasma drug concentration for Day −1 dosing;
$AUC_{0-last,overall}$ = the area under the plasma concentration versus time curve from time 0 on Day −1 to the last measurable plasma drug concentration after the last dose on Day 28;
$C_{avg}$ = calculated as $AUC_{0-14d}$ divided by Tau;
$Cl_{ss}$ = calculated as Dose/$AUC_{0-14d}$;
$C_{max,-1d}$ = maximum observed plasma concentration for Day −1 dosing;
$C_{max,28d}$ = maximum observed plasma concentration between dose time and dose time + Tau for Day 28 dosing;
$C_{min}$ = minimum concentration between dose time and dose time + Tau (at the time of minimum concentration sampled during a dosing interval);
CV % = coefficient of variation;
PK = pharmacokinetic;
SD = standard deviation;
$t_{max,-1d}$ = the time of maximum observed plasma concentration for Day −1 dosing;
$t_{max,28d}$ = the time of maximum observed plasma concentration during a dosing interval for Day 28 dosing;
$T_{min}$ = time of minimum concentration sampled during a dosing interval.

The clinical evidence from the phase IIa study strongly suggests that CD24Fc, administered in combination with methotrexate and tacrolimus, greatly improves outcomes in leukemia patients undergoing myeloablative allo-HCT by reducing both the likelihood of severe aGVHD (grades III-IV) and the likelihood of leukemia relapse. As described above, the cumulative incidence of grade III-IV aGVHD is 5.6% in CD24Fc exposed patients as compared to 16.7% in the placebo cohort (saline plus methotrexate and tacrolimus) and 24% in the contemporary control cohort (methotrexate and tacrolimus alone). These data suggest that administration of CD24Fc in combination with methotrexate and tacrolimus as prophylaxis reduces the risk of grade III-IV aGVHD in HCT patients, the most serious grades of aGVHD which are associated with increased risk of non-relapse mortality. A trend of reduction is observed in the incidence of relapse in patients who received CD24Fc (11.1%) as compared to patients who did not, both as compared to the placebo arm (33.3%) and the contemporary control (23%), demonstrating that CD24Fc does not affect the GVT effects of the graft and may even reduce the risk of leukemia relapse. The benefit of including CD24Fc in standard GVHD prophylaxis regimens is further supported by the better NRM in CD24Fc exposed patients (5.6%) as compared to placebo (16.7%), better 1.5-year overall survival (89% versus 50%, CD24Fc versus placebo control), a statistically significant improvement in grade III-IV aGVHD RFS (83% versus 33%, CD24Fc versus placebo control, respectively), a dose-dependent reduction in severe mucositis, and a good safety profile with only one drug-related TEAE (grade III) observed in the study.

A prophylaxis agent that reduces the risk of both aGVHD and leukemia relapse would be novel and extremely beneficial to leukemia patients undergoing allo-HCT following myeloablative conditioning. As described above, the early clinical data in this application strongly suggests that administration of CD24Fc in combination with methotrexate and tacrolimus provides a substantial improvement over existing prophylaxis regimens on the clinically significant endpoints of grade III-IV aGVHD prevention and leukemia relapse, and thus should be eligible for Breakthrough Designation. The effects of CD24Fc observed in the phase IIa portion of the clinical study will be further investigated in the phase IIb portion, which has been designed to confirm the efficacy of prophylactic CD24Fc administration in reducing Grade III-IV aGVHD and leukemia relapse in leukemia patients undergoing allo-HCT following myeloablative conditioning.

Example 6

CD24 can be Used to Prevent Relapse

The phase IIA clinical trial data revealed that prophylaxis with CD24Fc in addition to standard of care results in 3-fold reduction leukemia relapse when compared to placebo control that received standard of care. These data suggest that, in addition to its ability to preserve graft vs leukemia effect, CD24Fc may directly reduce leukemia relapse in leukemia patients that have undertaken hematopoietic stem cell transplantation (HCT).

A potential mechanism of leukemia relapse is due to persistence of leukemia stem cells. John Dick and colleagues led the revival of the cancer stem cell (CSC) concept nearly 20 years ago using a leukemia model [1]. Leukemia CSC activity has been assayed by in vitro CFU and in vivo xenogeneic transplantation models [1]. Both models have also been used to test drugs for potential therapeutic development as leukemia drugs [2]. As the first-step to test if CD24Fc may affect leukemia stem cell activity, CFU assays were performed to evaluate potential effect of CD24Fc on leukemia stem cell activities, including self-renewal and production of leukemia cells.

Experimental Protocol

1. Thaw bottle of complete MethoCult medium at room temperature or overnight at 2-8° C.
2. Shake vigorously for 1 min and then let stand for at 5 min to allow bubbles to rise to the top before using.
3. Use a 3 mL syringe attached to a 18 gauge Blunt-End Needle to dispense MethoCult medium into sterile tubes. Dispense 4 mL per tube for triplicate cultures.
4. Prepare 12-well culture plates, add 3-4 ml of sterile water to the empty spaces between the wells.
5. Prepare Leukemia cell line samples, count viable cells using trypan blue dye.
6. Dilute the cells and CD24Fc/IgG Fc with 2% FBS IMDM to 20× the final concentration required for plating.
   Example: For THP-1 cell, final plating concentration is 500-1000 cells per well, prepare a cell suspension of $1 \times 10^4$-$2 \times 10^4$ cells per mL.
7. For each well, add 50 µl of diluted cells and 50 µl diluted CD24Fc or IgG Fc control to 1 mL MethoCult medium. For a triplicate assay, add 0.2 mL of diluted cells and 0.2 ml CD24Fc or IgG Fc to a pre-aliquoted 4 mL MethoCult medium tube.
   Note: This 1:10 (v/v) ratio of cells: medium gives the correct viscosity to ensure optimal CFU growth and morphology.
8. Vortex the tube for 10 seconds to mix the contents thoroughly.
9. Let stand for 5 minutes to allow the bubbles to rise to the top.
10. Attach a sterile 18 gauge Blunt-End Needle to a sterile 3 mL syringe. Dispense the MethoCult mixture containing cells into culture plate, 1.1 ml per well.
11. Distribute the medium evenly across the surface by gently tilting and rotating the plate to allow the medium to attach to the wall of the dish on all sides.
12. Incubate at 37° C., in 5% CO2 with ≥95% humidity for 7-14 days.
13. Count the colonies using a high-quality inverted microscope.

For replating:

1. After counting the colonies, dilute the medium containing colonies by adding 4 ml 2% FBS IMDM to each well.
2. For each well, transfer the total 5 ml cell suspension to a 15 ml tube. Centrifuge at 500 g for 5 minutes at 4° C.
3. Carefully remove the supernatant, add 1 ml 2% FBS IMDM to resuspend the cells.
4. Perform a cell count using trypan blue dye for each tube.
5. Setup CFU assays following the same steps above (steps 6-13) in CFU assay.

Data Analysis and Statistics

The CFU activities of 5 leukemia cells lines were expressed as number of colonies generated from 500-100 cells per well. Data presented are means+/−standard errors (SEM).

The self-renewal of CFU activities was assayed by serial replating. Cumulative CFUs in each round were calculated based on the cumulative numbers of leukemia progeny cells in the previous rounds and the number of CFU per 500 cells, as determined based on the following formulae.

Cumulative CFU=(Cumulative number of leukemia cells/500)×CFU per 500 cells in which the cumulative number of leukemia cells is determined by Cumulative leukemia cell number=(number of leukemia cells in previous round/500)×number of leukemia cells in the current round.

Statistical significance (P values) were determined by two-tailed unpaired student t tests. *P<0.05, P<0.01, *P<0.001.

Results

1. CD24Fc Reduces CFU Activity of Multiple Leukemia Cell Lines

To determine the effect of CD24Fc on leukemia stem cell ability in vitro, the number of CFU of five leukemia cell lines were evaluated when they had been cultured in the presence of CD24Fc or control IgG Fc. As shown in Table 12, the cell lines included a diverse group of leukemia.

TABLE 12

| Leukemia cell lines | | |
|---|---|---|
| Name | Disease | Reference |
| THP-1 | acute monocytic leukemia | [3] |
| K562 | chronic myelogenous leukemia | [4] |
| Kasumi-1 | acute myeloblastic leukemia | [5] |
| NB4 | acute promyelocytic leukemia | [6] |
| U937 | histiocytic lymphoma | [7] |

Figure 24:
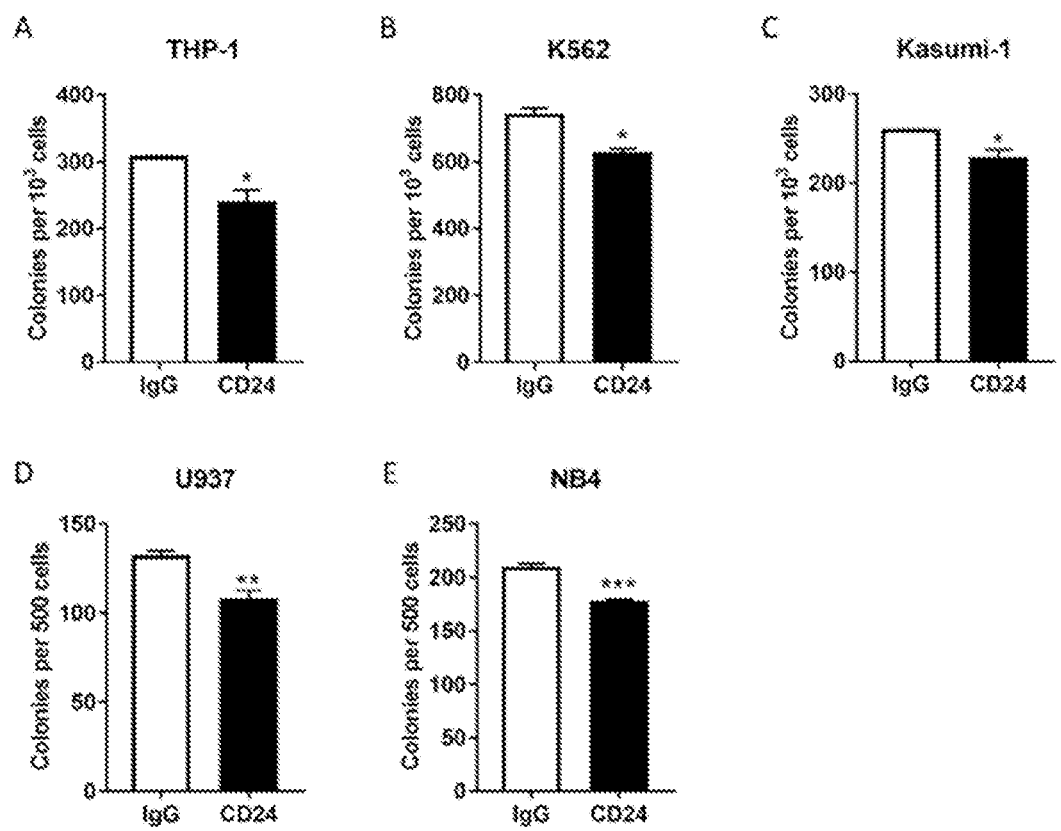
FIGS. 24A-E show CD24Fc broadly suppresses leukemia CFU activity. Colony formation assays were carried out by plating 500-1000 cells of different cell lines in methylcellulose medium with CD24Fc or IgG (100 μg/ml). The colony numbers were scored 7-14 days later. Data represent are means±SEM.

The means and standard error of CFU numbers observed after one round of CD24Fc or IgG Fc treatment is shown in Table 13 and FIG. 24. These data demonstrate that when compared with IgG Fc, CD24Fc significantly reduced the CFU number of all five cell lines tested.

TABLE 13

| CD24Fc broadly suppresses leukemia CFU activities in vitro. | | | |
|---|---|---|---|
| Leukemia cell lines | IgG group | CD24Fc group | P value |
| | Colonies per $10^3$ cells | Colonies per $10^3$ cells | |
| THP-1 | 306 ± 2.5 | 238 ± 19.4 | 0.0254 |
| K562 | 739 ± 21.5 | 623.3 ± 16 | 0.0125 |
| Kasumi-1 | 258.8 ± 1.4 | 227 ± 10.5 | 0.0239 |
| | Colonies per 500 cells | Colonies per 500 cells | |
| NB4 | 208 ± 5.2 | 176.4 ± 3.1 | 0.0009 |
| U937 | 131.4 ± 3.5 | 107.2 ± 5.6 | 0.0064 |

2. CD24Fc Progressively Reduces Self-Renewal of Leukemia CFU Activities

To detect the effect of CD24 on leukemia CSC self-renewal, serial replating of THP-1 cells was performed. Briefly, THP-1 cells were isolated from colonies from either CD24Fc or IgG Fc-treated plates. Five hundred THP1 cells were cultured again in methylcellulose medium in the presence of the same drug for a total of 4 rounds. The number of CFU yielded from the first 500 THP-1 cells are actual number of THP-1 CFU from 500 cells, while those for subsequent rounds were calculated based on the number of leukemia cells from previous round times the CFU per 500 cells. These data, presented in Table 14 and in FIG. 25A, demonstrated that THP-1 cells treated with CD24Fc leads to progressively greater decrease in the CFU numbers. By the 4th round, the cumulative number of CFU in CD24Fc-treated group have 11.6-fold less CFU than the IgG Fc-treated group. These data suggest that CD24Fc progressively reduces self-renewal of leukemia stem cell activity. In addition, as shown in FIG. 25B, the colonies in CD24Fc-treated groups were considerably smaller.

TABLE 14

Cumulative effect of CD24Fc on CFU number of THP-1 cells in serial replating.

| THP-1 | IgG group Total colonies | CD24Fc group Total colonies | P value |
|---|---|---|---|
| 1st round | 178.5 ± 3.3 | 163.3 ± 4.2 | 0.0283 |
| 2nd round | 1.73E+05 ± 1.06E+04 | 1.15E+05 ± 9.39E+03 | 0.0067 |
| 3rd round | 1.10E+08 ± 1.85E+07 | 2.83E+07 ± 5.66E+06 | 0.0057 |
| 4th round | 9.00E+10 ± 2.59E+10 | 7.76E+09 ± 2.12E+09 | 0.0193 |

3. CD24Fc Progressively Reduces the Number of Leukemia Progeny Cells During Serial Replating To investigate the effect of CD24Fc on the number of leukemia cells in the colonies, the number of leukemia cells per well were counted at each round of the CFU assay and the cumulative yield based on the cell numbers in the previous rounds was calculated, as detailed in the method section. The data are shown in Table 15 and FIG. 26. Corresponding to reduction of colony sizes and numbers (FIG. 25), CD24Fc significantly decreased the cell number of THP-1 cells in four serial replatings. By the fourth round, the cumulative yield in CD24Fc-treated group was 22-fold less than that of the IgG Fc-treated group.

TABLE 15

Cumulative effect of CD24Fc on THP-1 cell numbers during serial replating

| THP-1 | IgG group Total cell number | CD24Fc group Total cell number | P value |
|---|---|---|---|
| 1st round | 7.18E+05 ± 2.86E+04 | 5.81E+05 ± 2.61E+04 | 0.0125 |
| 2nd round | 4.05E+08 ± 6.26E+07 | 1.26E+08 ± 2.08E+07 | 0.0055 |
| 3rd round | 3.50E+11 ± 1.02E+11 | 5.25E+10 ± 1.29E+10 | 0.0279 |
| 4th round | 2.49E+14 ± 8.75E+13 | 1.15E+13 ± 4.01E+12 | 0.0351 |

CONCLUSIONS

Since leukemia relapse has been attributed to leukemia stem cell activity, the effect of CD4Fc on colony forming unit (CFU) activity, a surrogate assay for leukemia stem cell activity, was evaluated for five leukemia cell lines. The data demonstrate that CD24Fc broadly inhibited CFU activity of all cell lines tested. To evaluate if CD24Fc affect self-renewal of leukemia stem cells, 4-rounds of serial replating of one of the leukemia cell lines, THP-1, were performed. The data demonstrate that over 4 rounds, CD24Fc reduced cumulative CFU numbers by nearly 12-fold. In addition, the size of colonies in CD24Fc-treated group was considerably smaller. Correspondingly, the cumulative yield of leukemia cells was reduced even more than that of the CFU numbers. The cumulative number of leukemia cell yield was reduced by CD24Fc by nearly 22-fold after 4 rounds of replating. Together, the data demonstrate that CD24Fc can suppress leukemia stem cell activity and provide a plausible explanation for reduced leukemia relapse observed in phase IIA clinical trials of leukemia HCT patients.

REFERENCES

1. Lapidot T, Sirard C, Vormoor J et al. A cell initiating human acute myeloid leukaemia after transplantation into SCID mice. Nature. 1994. 367: 645-648.
2. Jin L, Hope K J, Thai Q et al. Targeting of CD44 eradicates human acute myeloid leukemic stem cells. Nat Med. 2006. 12: 1167-1174.
3. Tsuchiya S, Yamabe M, Yamaguchi Y et al. Establishment and characterization of a human acute monocytic leukemia cell line (THP-1). Int J Cancer. 1980. 26: 171-176.
4. Lozzio B B, Lozzio C B. Properties and usefulness of the original K-562 human myelogenous leukemia cell line. Leuk Res. 1979. 3: 363-370.
5. Asou H, Tashiro S, Hamamoto K et al. Establishment of a human acute myeloid leukemia cell line (Kasumi-1) with 8; 21 chromosome translocation. Blood. 1991. 77: 2031-2036.
6. Lanotte M, Martin-Thouvenin V, Najman S et al. NB4, a maturation inducible cell line with t(15;17) marker isolated from a human acute promyelocytic leukemia (M3). Blood. 1991. 77: 1080-1086.
7. Sundstrom C, Nilsson K. Establishment and characterization of a human histiocytic lymphoma cell line (U-937). Int J Cancer. 1976. 17: 565-577

CD24 reduces leukemia stem cell activity

This example further demonstrates that C24 reduces leukemia stem cell activity. Allogeneic hematopoietic stem cell transplantation (HSCT) is a curative option for hematopoietic malignancies. However, approximately 25-30% of HSCT patients relapse within one year. Data from phase II clinical trials revealed that prophylaxis with CD24Fc in addition to standard of care results in 3-fold reduction leukemia relapse when compared to placebo control that received standard of care. These data suggest that, in addition to its ability to preserve graft vs. leukemia effect, CD24Fc may directly reduce leukemia relapse. In particular, it was found that none of the 12 cases of AML and MDS patients relapsed over the entire observation period of 8-22 months.

A potential mechanism of leukemia relapse is due to persistence of leukemia stem cells. John Dick and colleagues led the revival of the cancer stem cell (CSC) concept nearly 20 years ago using leukemia model. Leukemia CSC activity has been assayed by in vitro CFU and in vivo xenogeneic transplantation models. Both models have also been used to test drugs for potential therapeutic development as leukemia drugs. As the first-step to test if CD24Fc may affect leukemia stem cell activity, CFU assays were performed to evaluate the potential effect of CD24Fc on leukemia stem cell activities, including self-renewal and production of leukemia cells.

CD24Fc Reduces CFU Activity of Multiple Leukemia Cell Lines.

To determine the effect of CD24Fc on leukemia stem cell ability in vitro, the number of CFU of five leukemia cell lines was evaluated when the cells had been cultured in the presence of CD24Fc or control IgG Fc. The cell lines included a diverse group of leukemia, including 4 AML cell lines, THP1, K562, Kasumi-1, NB4 and histiocytic lymphoma cell line U937. The means and standard error of CFU numbers observed after one round of CD24Fc or IgG Fc treatment is shown in FIG. 24. These data demonstrate that when compared with IgG Fc, CD24Fc significantly reduced the CFU number of all five cell lines tested.

CD24Fc Progressively Reduces Self-Renewal of Leukemia CFU Activities

Figure 28:
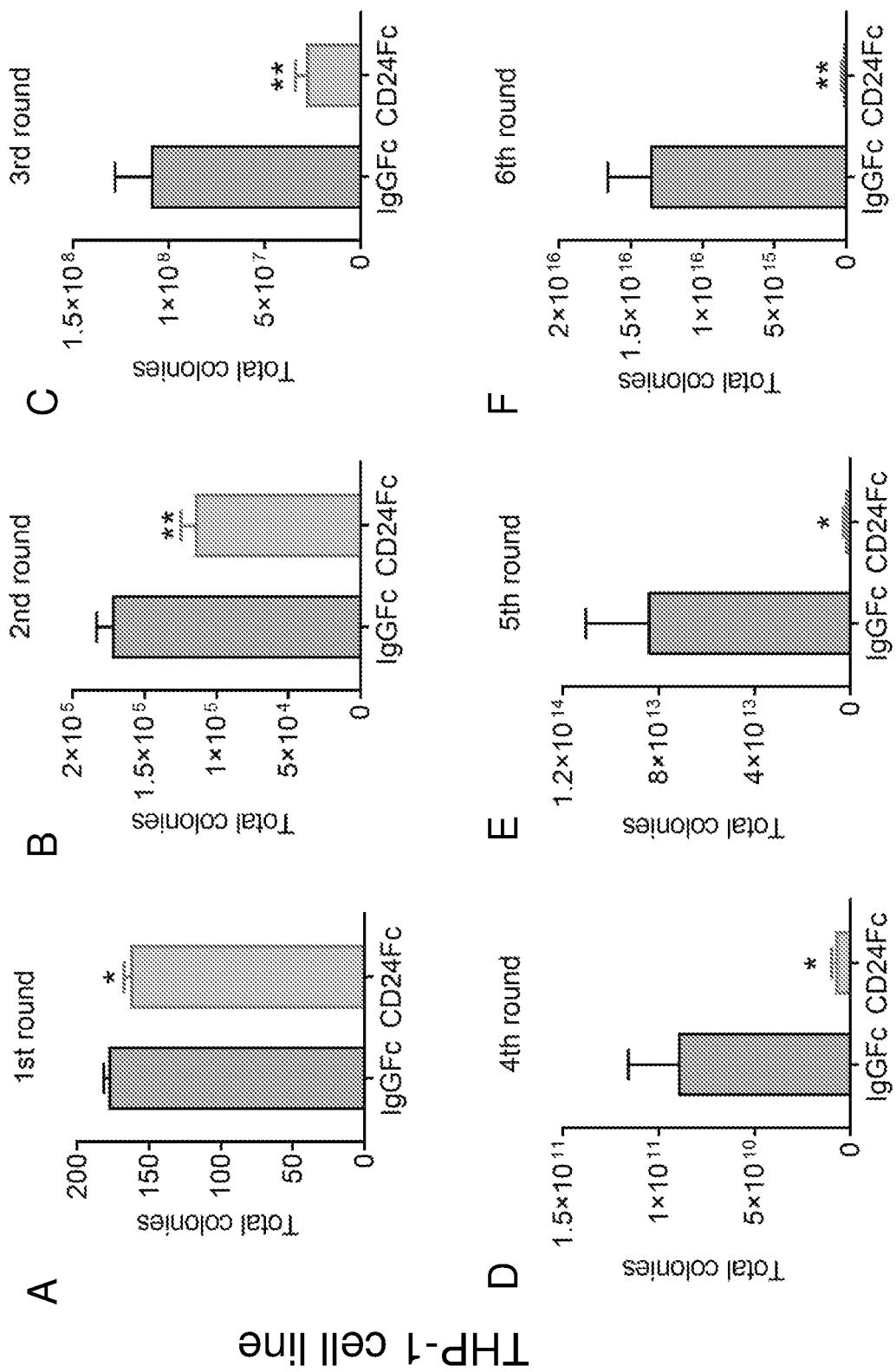
FIGS. 28A-F demonstrate that CD24Fc progressively reduces AML CFU activity in serial replating. Experiments were performed on THP-1 cells. THP1 cells (500 cells/well), either from bulk culture (first round) or from previous colony forming assay plates (second and third round), were plated in methylcellulose medium with CD24Fc or IgG (100 μgimp. The colony numbers were scored 7 days later. Data represented are means±SEM.

To evaluate the effect of CD24 on leukemia CSC self-renewal, serial replating of THP-1 cells was performed. Briefly, THP-1 cells were isolated from colonies from either CD24Fc or IgG Fc-treated plates. Five hundred THP1 cells were cultured again in methylcellulose medium in the presence of the same drug for a total of 4 rounds. The number of CFU yielded from the first 500 THP-1 cells are actual number of THP-1 CFU from 500 cells, while those for subsequent rounds were calculated based on the number of leukemia cells from previous round times the CFU per 500 cells. These data, presented in in FIG. 25A, demonstrated that THP-1 cells treated with CD24Fc leads to progressively greater decrease in the CFU numbers. By the 4th round, the cumulative number of CFU in CD24Fc-treated group have 11.6-fold less CFU than the IgG Fc-treated group. These data suggest that CD24Fc progressively reduces self-renewal of leukemia stem cell activity. In addition, as shown in FIG. 25B, the colonies in CD24Fc-treated groups were considerably smaller. Further studies showed that the effect of CD24 persisted over 6 rounds of plating (FIG. 28).

CD24Fc Progressively Reduces the Number of Leukemia Progeny Cells During Serial Replating To investigate the effect of CD24Fc on the number of leukemia cells in the colonies, the number of leukemia cells per well was counted at each round of the CFU assay, and the cumulative yield was calculated based on the cell numbers in the previous rounds, as detailed in the method section. The data are shown in FIG. 26. Corresponding to reduction of colony sizes and numbers (FIG. 25), CD24Fc significantly decreased the cell number of THP-1 cells in four serial replatings. By the fourth round, the cumulative yield in CD24Fc-treated group was 22-fold less than that of the IgG Fc-treated group.

Taken together, these data demonstrated that CD24Fc broadly reduces CFU activity of multiple leukemia cell lines, that CD24Fc reduces self-renewal of THP-1 leukemia CFU activity, and that CD24Fc reduces the cumulative number of THP-1 during serial replating. These data prompt testing of the hypothesis that CD24Fc can directly affect the leukemia stem cell activity, as detailed below.

Reduction of CFU Activity of Primary Leukemia Cells by CD24Fc

Figure 25:
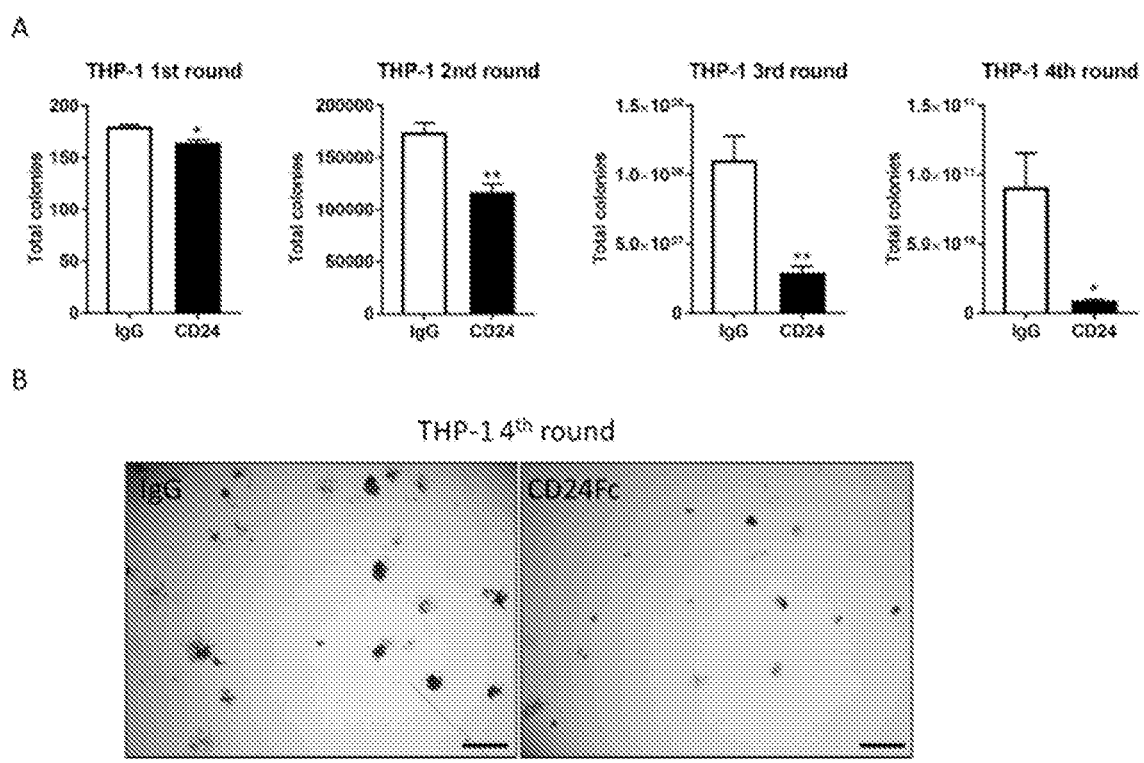
FIGS. 25A-B show cumulative effect of CD24Fc on THP-1 CFU activity in serial replating. The THP-1 cells (500 per well) were serially replated four rounds in methylcellulose medium with CD24Fc or IgG Fc (100 μg/ml). The colony numbers were scored 7 days after plating under a microscope.
Figure 26:
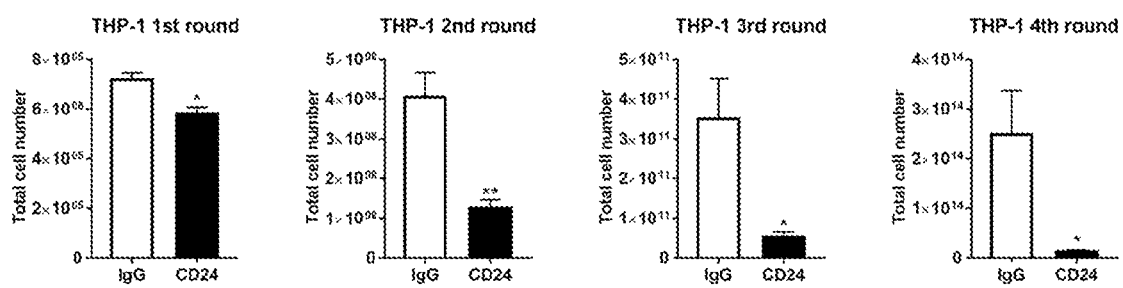
FIG. 26 shows CD24Fc decreases cumulative leukemia cell number during serial replating. The THP-1 cells (500 per well) were serially replated four rounds in methylcellulose medium with CD24Fc or IgG (100 μg/ml). The cell numbers were counted 7 days after plating. The total cell numbers were calculated based on the cells in the previous rounds and the yield in the current round, as detailed in the method section.

To substantiate the data with established AML and other leukemia cell lines in FIG. 24-26, the effect of CD24Fc on the primary leukemia isolates from clinics was tested. Clinical isolates of 5 AML and 5 CML patients were tested at University of Maryland Medical Center. The samples in CFU assays were evaluated as demonstrated in preliminary studies. As shown in FIG. 27, all showed reduced CFU activity.

CD33 is Responsible for CD24Fc-Mediated Reduction of CFU in THP1 Cells

Figure 29:
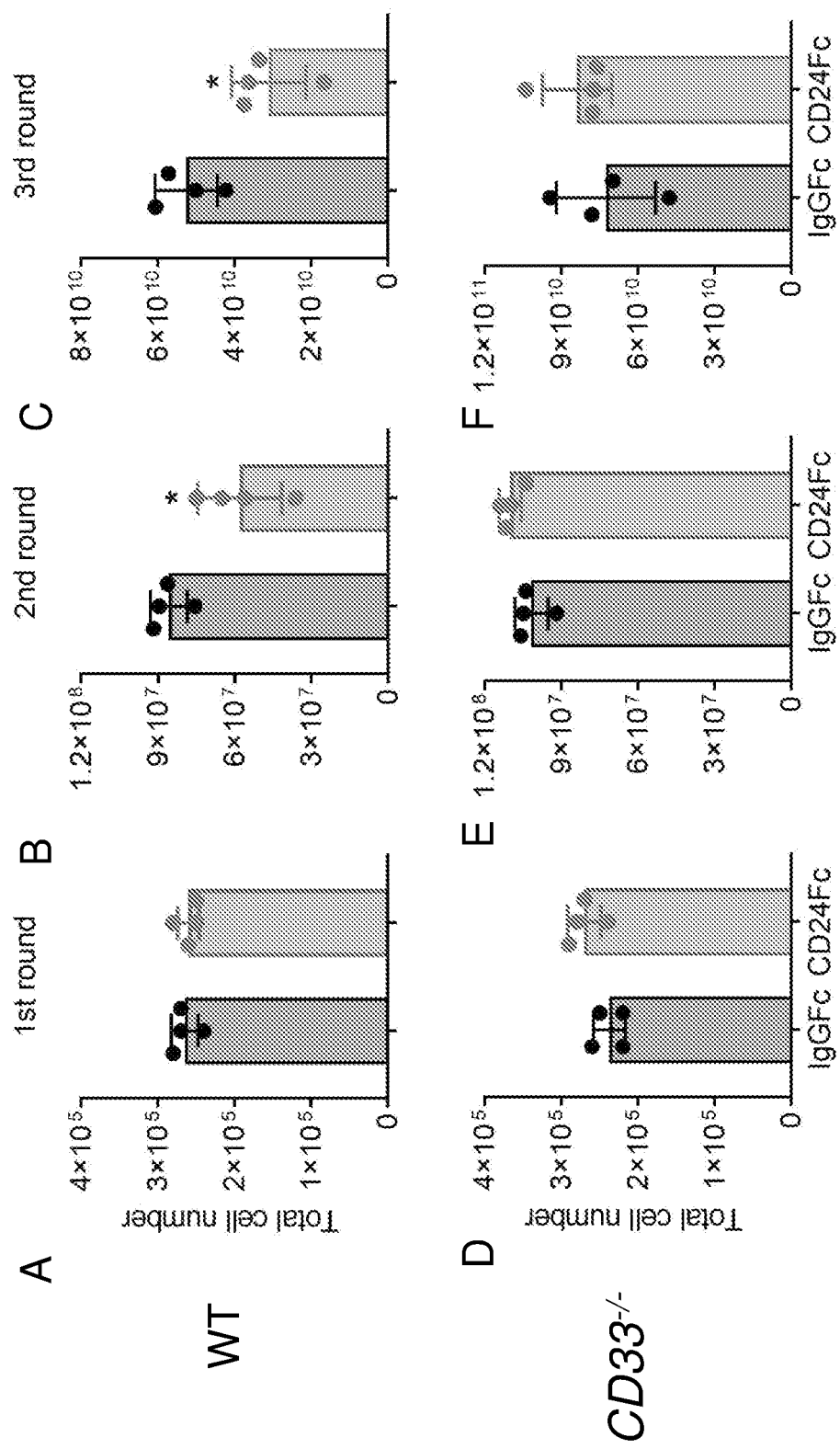
FIGS. 29A-F show that CD24Fc progressively reduces leukemia CFU activity through human CD33. Experiments were performed on wild-type (FIGS. 29A-C) and CD33$^{-/-}$ THP-1 (FIGS. 29D-F) cells. WT or CD33$^{-/-}$ THP1 cells (500 cells/well), either from bulk culture (first round) or from previous colony forming assay plates (second and third round), were plated in methylcellulose medium with CD24Fc or IgG (100 μg/ml). The colony numbers were scored 7 (WT) 14 (CD33$^{-/-}$) days later. Data represented are means±SEM.

The major Siglec on THP1 cells is CD33. To test relevance of CD33 for CD24Fc-mediated suppression of leukemia stem cell activity, CD33$^{-/-}$ THP1 cells were generated using the Crispr-Cas9 method, and WT and CD33$^{-/-}$ THP1 cells were compared for response to CD24Fc. Since WT THP1 cells form CFU within 7 days, while CD33$^{-/-}$ CFU is visible in 14 days, their CFU were counted at different time points. As shown in FIG. 29, CD24Fc progressively reduced CFU activity of WT but not CD33$^{-/-}$ THP1 cells, which demonstrate that CD33 plays a critical role in stem cell activity, as analyzed by CFU assay.

The invention claimed is:

1. A method of treating relapse of a cancer in a subject in need thereof, comprising administering a pharmaceutically acceptable amount of a CD24 protein fused to a Fc region of a mammalian Ig protein (CD24Fc) to the subject,
    wherein the cancer is Acute Myeloid Leukemia (AML), Acute Lymphoblastic Leukemia (ALL), Chronic Myelogenous Leukemia (CML), Myelodysplastic syndrome (MDS), or Chronic Myelomonocytic Leukemia (CMML),
    wherein the subject will undergo or has undergone a hematopoietic stem cell transplantation (HCT), wherein the CD24Fc protein is administered in a first dose of 240 mg or 480 mg on day −4 to day 0, wherein the day of stem cell transplant is day 0, wherein the CD24Fc protein is administered in a second dose of 240 mg or 480 mg on day+9 to day+19, wherein the CD24Fc protein is administered in a third dose of 240 mg or 480 mg on day+18 to day+38,
    wherein treating the relapse of the cancer suppresses or represses the relapse.

2. The method of claim 1, wherein the first dose of CD24Fc protein is 480 mg, the second dose is 240 mg, and the third dose is 240 mg.

3. The method of claim 1, wherein the first dose of CD24Fc protein is administered one day before the HCT.

4. The method of claim 1, wherein the CD24Fc protein is soluble.

5. The method of claim 1, wherein the CD24Fc protein is glycosylated.

6. The method of claim 1, wherein the CD24Fc protein is prepared using a eukaryotic expression system.

7. The method of claim 6, wherein the eukaryotic expression system comprises expression from a vector in mammalian cells.

8. The method of claim 7, wherein the mammalian cells are Chinese Hamster Ovary cells.

9. The method of claim 1, wherein the first dose of CD24Fc protein is administered on the day before the HCT, the second dose is administered on day 14 after the HCT, and the third dose is administered on day 28 after the HCT.

10. The method of claim 9, wherein the doses of the CD24Fc protein are 480 mg, 240 mg, and 240 mg, respectively.

11. The method of claim 1, wherein the CD24Fc protein comprises a mature human CD24 polypeptide fused at its N-terminus or C-terminus to a Fc region of a mammalian immunoglobulin (Ig) protein.

12. The method of claim 11, wherein the mature human CD24 polypeptide comprises SEQ ID NO: 1 or 2.

13. The method of claim 12, wherein the Ig protein is human, and wherein the Fc region comprises a hinge region and CH2, CH3 and CH4 domains of IgM.

14. The method of claim 12, wherein the Ig protein is human, and wherein the Fc region comprises a hinge region and CH2 and CH3 domains of IgG1, IgG2, IgG3, IgG4, or IgA.

15. The method of claim 14, wherein the CD24Fc protein comprises SEQ ID NO: 6, 11, or 12.

16. The method of claim 15, wherein the amino acid sequence of the CD24Fc protein consists of SEQ ID NO: 6, 11, or 12.

* * * * *